US007129065B2

(12) United States Patent
Ohe

(10) Patent No.: US 7,129,065 B2
(45) Date of Patent: Oct. 31, 2006

(54) BHLH-PAS PROTEINS, GENES THEREOF AND UTILIZATION OF THE SAME

(75) Inventor: Norihisa Ohe, Nara (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 10/465,920

(22) PCT Filed: Dec. 17, 2001

(86) PCT No.: PCT/JP01/11064

§ 371 (c)(1),
(2), (4) Date: Jun. 27, 2003

(87) PCT Pub. No.: WO02/053729

PCT Pub. Date: Jul. 11, 2002

(65) Prior Publication Data
US 2004/0248247 A1 Dec. 9, 2004

(30) Foreign Application Priority Data
Dec. 27, 2000 (JP) ............................. 2000-398548
Mar. 19, 2001 (JP) ............................. 2001-077740

(51) Int. Cl.
*C12P 21/02* (2006.01)
*C07K 14/00* (2006.01)
*C07H 17/00* (2006.01)
(52) U.S. Cl. ............... 435/69.1; 435/320.1; 435/252.3; 435/325; 435/7.1; 435/6; 536/23.1; 530/350
(58) Field of Classification Search ............... 536/23.1; 435/69.1, 320.1, 252.3, 325, 6, 7.1; 530/350
See application file for complete search history.

(56) References Cited
U.S. PATENT DOCUMENTS
2003/0190653 A1* 10/2003 Shamloo et al. ............... 435/6

FOREIGN PATENT DOCUMENTS
WO  WO 98/31804 A  7/1998
WO  WO 99/28464 A2  6/1999

OTHER PUBLICATIONS
Adams et al. 1995; Nature 377: 3-174.*
Bonaldo et al. 1996; Genome Research 6(9): 791-806.*
Carninci et al. Oct. 2000; Genome Research 10: 1617-1630.*
Ooe et al. 2004; Molecular and Cellular Biology 24(2): 608-616.*
Database EMBL Online!, NCI CGAP; Feb. 1, 2000, retrieved from EBI Database accession No. AW340980, XP002302819.

Brunskill Eric W et al: "Characterization of Npas3, a novel basic helix-loop-helix PAS gene expressed in the developing mouse nervous system", Mechanisms of Development, vol. 88, No. 2, Nov. 1999, pp. 237-241, XP002302785, ISSN: 0925-4773.
Chrast R et al: "Cloning of Two Human Homologs of the Drosophila single-minded Gene SIM1 on Chromosome 6Q and SIM2 on 21q Within the Down Syndrome Chromosomal Region", Genome Research, Cold Spring Harbor Laboratory Press, US, vol. 7, 1997, pp. 615-624, XP002905945.
Ikeda et al: "cDNA Cloning and Tissue-Specific Expression of a Novel Basic Helix-Loop-Helix/PAS Protein (BMAL1) and Identification of Alternatively Spliced Variants with Alternative Translation Initiation Site Usage", Biochemical and Biophysical Research Communications, Academic Press Inc., Orlando, FL. US, vol. 233, No. 1, Apr. 1997, pp. 258-264, XP002100827, ISSN: 0006-291X.
Garcia Joseph A. et al.: "Impaired Cued and Contextual Memory in NPAS2-Deficient Mice", www.sciencemag.org, vol. 288, Jun. 2000, pp. 2226-2230, XP-02303045.
Gerlai Rober: "Eph receptors and neural plasticity", Nature Reviews, Neuroscience, vol. 2, No. 3, Mar. 2001, pp. 205-209.
Hatanpaa K. et al: "Loss of Proteins Regulating Synaptic Plasticity in Normal Aging of the Human Brain and in Alzheimer Disease", J. Neuropathology and Experimental Neurology, vol. 58, No. 6, Jun. 1999, pp. 637-643.
Harigaya Y. et al.: "Disappearance of Actin-Binding Protein, Drebrin, From hippocampal Synapses in Alzheimer's Disease", Journal of Neuroscience Research, Wiley-Liss,Inc., vol. 43, 1996, pp. 87-92.
Hosoya T. et al.: "Defective development of secretory neurons in the hypothalamus of Arnt2-knockout mice", Genes to Cells, Blackwell Science Limited, vol. 6, 2001, pp. 361-374.
Yu-Dong Zhou et al., Molecular characterization of two mammalian bHLH-PAS domain proteins selectively expressed in the central nervous system., *Proc. Nat'l Acad. Sci.*, USA, Jan. 1997, vol. 94, pp. 713-718.
Gu Yi-Zhong, et al: "The PAS Superfamily: Sensors of Environmental and Development Signal", Annu. Rev. Pharmacol. Toxicol, (2000), vol. 40, pp. 519-561.

* cited by examiner

*Primary Examiner*—Karen Cochrane Carlson
(74) *Attorney, Agent, or Firm*—Sughrue Mion, PLLC

(57) ABSTRACT

The present invention relates to proteins, including a protein represented by any of SEQ ID NOs: 1 to 3; a protein exhibiting an amino acid identity of 90% or more to the amino acid sequence represented by any of SEQ ID NOs: 1 to 3 and also having a transcription regulation ability; or a protein having a transcription regulation ability and containing an amino acid sequence encoded by a DNA which hybridizes under a stringent condition with a DNA consisting of the nucleotide sequence represented by the nucleotide numbers 102 to 2507 in the nucleotide sequence represented by SEQ ID NO: 4, 51 to 2456 in the nucleotide sequence represented by SEQ ID NO: 5, or 35 to 2440 in the nucleotide sequence represented by SEQ ID NO: 6, or a DNA encoding the same.

21 Claims, 2 Drawing Sheets

SEQUENCE LISTING

<160> NUMBER OF SEQ ID NOS: 64

<210> SEQ ID NO 1
<211> LENGTH: 802
<212> TYPE: PRT
<213> ORGANISM: Homo sapiens

<400> SEQUENCE: 1

```
Met Tyr Arg Ser Thr Lys Gly Ala Ser Lys Ala Arg Arg Asp Gln Ile
  1               5                  10                  15

Asn Ala Glu Ile Arg Asn Leu Lys Glu Leu Leu Pro Leu Ala Glu Ala
                 20                  25                  30

Asp Lys Val Arg Leu Ser Tyr Leu His Ile Met Ser Leu Ala Cys Ile
             35                  40                  45

Tyr Thr Arg Lys Gly Val Phe Phe Ala Gly Gly Thr Pro Leu Ala Gly
         50                  55                  60

Pro Thr Gly Leu Leu Ser Ala Gln Glu Leu Glu Asp Ile Val Ala Ala
 65                  70                  75                  80

Leu Pro Gly Phe Leu Leu Val Phe Thr Ala Glu Gly Lys Leu Leu Tyr
                 85                  90                  95

Leu Ser Glu Ser Val Ser Glu His Leu Gly His Ser Met Val Asp Leu
            100                 105                 110

Val Ala Gln Gly Asp Ser Ile Tyr Asp Ile Ile Asp Pro Ala Asp His
            115                 120                 125

Leu Thr Val Arg Gln Gln Leu Thr Leu Pro Ser Ala Leu Asp Thr Asp
        130                 135                 140

Arg Leu Phe Arg Cys Arg Phe Asn Thr Ser Lys Ser Leu Arg Arg Gln
145                 150                 155                 160

Ser Ala Gly Asn Lys Leu Val Leu Ile Arg Gly Arg Phe His Ala His
                165                 170                 175

Pro Pro Gly Ala Tyr Trp Ala Gly Asn Pro Val Phe Thr Ala Phe Cys
            180                 185                 190

Ala Pro Leu Glu Pro Arg Pro Arg Pro Gly Pro Gly Pro Gly Pro Gly
        195                 200                 205

Pro Ala Ser Leu Phe Leu Ala Met Phe Gln Ser Arg His Ala Lys Asp
    210                 215                 220

Leu Ala Leu Leu Asp Ile Ser Glu Ser Val Leu Ile Tyr Leu Gly Phe
225                 230                 235                 240

Glu Arg Ser Glu Leu Leu Cys Lys Ser Trp Tyr Gly Leu Leu His Pro
                245                 250                 255

Glu Asp Leu Ala His Ala Ser Ala Gln His Tyr Arg Leu Leu Ala Glu
            260                 265                 270

Ser Gly Asp Ile Gln Ala Glu Met Val Val Arg Leu Gln Ala Lys Thr
        275                 280                 285

Gly Gly Trp Ala Trp Ile Tyr Cys Leu Leu Tyr Ser Glu Gly Pro Glu
    290                 295                 300

Gly Pro Ile Thr Ala Asn Asn Tyr Pro Ile Ser Asp Met Glu Ala Trp
305                 310                 315                 320

Ser Leu Arg Gln Gln Leu Asn Ser Glu Asp Thr Gln Ala Ala Tyr Val
                325                 330                 335

Leu Gly Thr Pro Thr Met Leu Pro Ser Phe Pro Glu Asn Ile Leu Ser
            340                 345                 350

Gln Glu Glu Cys Ser Ser Thr Asn Pro Leu Phe Thr Ala Ala Leu Gly
```

-continued

```
            355                 360                 365
Ala Pro Arg Ser Thr Ser Phe Pro Ser Ala Pro Glu Leu Ser Val Val
    370                 375                 380

Ser Ala Ser Glu Glu Leu Pro Arg Pro Ser Lys Glu Leu Asp Phe Ser
385                 390                 395                 400

Tyr Leu Thr Phe Pro Ser Gly Pro Glu Pro Ser Leu Gln Ala Glu Leu
                405                 410                 415

Ser Lys Asp Leu Val Cys Thr Pro Pro Tyr Thr Pro His Gln Pro Gly
            420                 425                 430

Gly Cys Ala Phe Leu Phe Ser Leu His Glu Pro Phe Gln Thr His Leu
                435                 440                 445

Pro Thr Pro Ser Ser Thr Leu Gln Glu Gln Leu Thr Pro Ser Thr Ala
            450                 455                 460

Thr Phe Ser Asp Gln Leu Thr Pro Ser Ser Ala Thr Phe Pro Asp Pro
465                 470                 475                 480

Leu Thr Ser Pro Leu Gln Gly Gln Leu Thr Glu Thr Ser Val Arg Ser
                485                 490                 495

Tyr Glu Asp Gln Leu Thr Pro Cys Thr Ser Thr Phe Pro Asp Gln Leu
            500                 505                 510

Leu Pro Ser Thr Ala Thr Phe Pro Glu Pro Leu Gly Ser Pro Ala His
            515                 520                 525

Glu Gln Leu Thr Pro Pro Ser Thr Ala Phe Gln Ala His Leu Asp Ser
            530                 535                 540

Pro Ser Gln Thr Phe Pro Glu Gln Leu Ser Pro Asn Pro Thr Lys Thr
545                 550                 555                 560

Tyr Phe Ala Gln Glu Gly Cys Ser Phe Leu Tyr Glu Lys Leu Pro Pro
                565                 570                 575

Ser Pro Ser Ser Pro Gly Asn Gly Asp Cys Thr Leu Leu Ala Leu Ala
            580                 585                 590

Gln Leu Arg Gly Pro Leu Ser Val Asp Val Pro Leu Val Pro Glu Gly
            595                 600                 605

Leu Leu Thr Pro Glu Ala Ser Pro Val Lys Gln Ser Phe Phe His Tyr
    610                 615                 620

Ser Glu Lys Glu Gln Asn Glu Ile Asp Arg Leu Ile Gln Gln Ile Ser
625                 630                 635                 640

Gln Leu Ala Gln Gly Met Asp Arg Pro Phe Ser Ala Glu Ala Gly Thr
                645                 650                 655

Gly Gly Leu Glu Pro Leu Gly Gly Leu Glu Pro Leu Asp Ser Asn Leu
            660                 665                 670

Ser Leu Ser Gly Ala Gly Pro Pro Val Leu Ser Leu Asp Leu Lys Pro
            675                 680                 685

Trp Lys Cys Gln Glu Leu Asp Phe Leu Ala Asp Pro Asp Asn Met Phe
    690                 695                 700

Leu Glu Glu Thr Pro Val Glu Asp Ile Phe Met Asp Leu Ser Thr Pro
705                 710                 715                 720

Asp Pro Ser Glu Glu Trp Gly Ser Gly Asp Pro Glu Ala Glu Gly Pro
                725                 730                 735

Gly Gly Ala Pro Ser Pro Cys Asn Asn Leu Ser Pro Glu Asp His Ser
            740                 745                 750

Phe Leu Glu Asp Leu Ala Thr Tyr Glu Thr Ala Phe Glu Thr Gly Val
            755                 760                 765

Ser Ala Phe Pro Tyr Asp Gly Phe Thr Asp Glu Leu His Gln Leu Gln
770                 775                 780
```

-continued

Ser Gln Val Gln Asp Ser Phe His Glu Asp Gly Ser Gly Gly Glu Pro
785                 790                 795                 800

Thr Phe
    802

<210> SEQ ID NO 2
<211> LENGTH: 802
<212> TYPE: PRT
<213> ORGANISM: Mus musculus

<400> SEQUENCE: 2

Met Tyr Arg Ser Thr Lys Gly Ala Ser Lys Ala Arg Arg Asp Gln Ile
  1               5                  10                  15

Asn Ala Glu Ile Arg Asn Leu Lys Glu Leu Leu Pro Leu Ala Glu Ala
                 20                  25                  30

Asp Lys Val Arg Leu Ser Tyr Leu His Ile Met Ser Leu Ala Cys Ile
             35                  40                  45

Tyr Thr Arg Lys Gly Val Phe Phe Ala Gly Gly Thr Pro Leu Ala Gly
 50                  55                  60

Pro Thr Gly Leu Leu Ser Ala Gln Glu Leu Glu Asp Ile Val Ala Ala
 65                  70                  75                  80

Leu Pro Gly Phe Leu Leu Val Phe Thr Ala Glu Gly Lys Leu Leu Tyr
                 85                  90                  95

Leu Ser Glu Ser Val Ser Glu His Leu Gly His Ser Met Val Asp Leu
                100                 105                 110

Val Ala Gln Gly Asp Ser Ile Tyr Asp Ile Ile Asp Pro Ala Asp His
            115                 120                 125

Leu Thr Val Arg Gln Gln Leu Thr Met Pro Ser Ala Leu Asp Ala Asp
130                 135                 140

Arg Leu Phe Arg Cys Arg Phe Asn Thr Ser Lys Ser Leu Arg Arg Gln
145                 150                 155                 160

Ser Ser Gly Asn Lys Leu Val Leu Ile Arg Gly Arg Phe His Ala His
                165                 170                 175

Pro Pro Gly Ala Tyr Trp Ala Gly Asn Pro Val Phe Thr Ala Phe Cys
            180                 185                 190

Ala Pro Leu Glu Pro Arg Pro Arg Pro Gly Pro Gly Pro Gly Pro Gly
        195                 200                 205

Pro Gly Pro Ala Ser Leu Phe Leu Ala Met Phe Gln Ser Arg His Ala
210                 215                 220

Lys Asp Leu Ala Leu Leu Asp Val Ser Glu Ser Val Leu Ile Tyr Leu
225                 230                 235                 240

Gly Phe Glu Arg Ser Glu Leu Leu Cys Lys Ser Trp Tyr Gly Leu Leu
                245                 250                 255

His Pro Glu Asp Leu Ala Gln Ala Ser Ser Gln His Tyr Arg Leu Leu
            260                 265                 270

Ala Glu Ser Gly Asp Ile Gln Ala Glu Met Val Val Arg Leu Gln Ala
        275                 280                 285

Lys His Gly Gly Trp Thr Trp Ile Tyr Cys Met Leu Tyr Ser Glu Gly
    290                 295                 300

Pro Glu Gly Pro Phe Thr Ala Asn Asn Tyr Pro Ile Ser Asp Thr Glu
305                 310                 315                 320

Ala Trp Ser Leu Arg Gln Gln Leu Asn Ser Glu Asp Thr Gln Ala Ala
                325                 330                 335

Tyr Val Leu Gly Thr Pro Ala Val Leu Pro Ser Phe Ser Glu Asn Val

-continued

```
                 340                 345                 350
Phe Ser Gln Glu Gln Cys Ser Asn Pro Leu Phe Thr Pro Ser Leu Gly
            355                 360                 365

Thr Pro Arg Ser Ala Ser Phe Pro Arg Ala Pro Glu Leu Gly Val Ile
        370                 375                 380

Ser Thr Pro Glu Glu Leu Pro Gln Pro Ser Lys Glu Leu Asp Phe Ser
385                 390                 395                 400

Tyr Leu Pro Phe Pro Ala Arg Pro Glu Pro Ser Leu Gln Ala Asp Leu
                405                 410                 415

Ser Lys Asp Leu Val Cys Thr Pro Tyr Thr Pro His Gln Pro Gly
            420                 425                 430

Gly Cys Ala Phe Leu Phe Ser Leu His Glu Pro Phe Gln Thr His Leu
        435                 440                 445

Pro Pro Pro Ser Ser Ser Leu Gln Glu Gln Leu Thr Pro Ser Thr Val
    450                 455                 460

Thr Phe Ser Glu Gln Leu Thr Pro Ser Ser Ala Thr Phe Pro Asp Pro
465                 470                 475                 480

Leu Thr Ser Ser Leu Gln Gly Gln Leu Thr Glu Ser Ser Ala Arg Ser
                485                 490                 495

Phe Glu Asp Gln Leu Thr Pro Cys Thr Ser Ser Phe Pro Asp Gln Leu
            500                 505                 510

Leu Pro Ser Thr Ala Thr Phe Pro Glu Pro Leu Gly Ser Pro Ala His
        515                 520                 525

Glu Gln Leu Thr Pro Ser Thr Ala Phe Gln Ala His Leu Asn Ser
    530                 535                 540

Pro Ser Gln Thr Phe Pro Glu Gln Leu Ser Pro Asn Pro Thr Lys Thr
545                 550                 555                 560

Tyr Phe Ala Gln Glu Gly Cys Ser Phe Leu Tyr Glu Lys Leu Pro Pro
                565                 570                 575

Ser Pro Ser Ser Pro Gly Asn Gly Asp Cys Thr Leu Leu Ala Leu Ala
            580                 585                 590

Gln Leu Arg Gly Pro Leu Ser Val Asp Val Pro Leu Val Pro Glu Gly
        595                 600                 605

Leu Leu Thr Pro Glu Ala Ser Pro Val Lys Gln Ser Phe Phe His Tyr
    610                 615                 620

Thr Glu Lys Glu Gln Asn Glu Ile Asp Arg Leu Ile Gln Gln Ile Ser
625                 630                 635                 640

Gln Leu Ala Gln Gly Val Asp Arg Pro Phe Ser Ala Glu Ala Gly Thr
                645                 650                 655

Gly Gly Leu Glu Pro Leu Gly Gly Leu Glu Pro Leu Asn Pro Asn Leu
            660                 665                 670

Ser Leu Ser Gly Ala Gly Pro Pro Val Leu Ser Leu Asp Leu Lys Pro
        675                 680                 685

Trp Lys Cys Gln Glu Leu Asp Phe Leu Val Asp Pro Asp Asn Leu Phe
    690                 695                 700

Leu Glu Glu Thr Pro Val Glu Asp Ile Phe Met Asp Leu Ser Thr Pro
705                 710                 715                 720

Asp Pro Asn Gly Glu Trp Gly Ser Gly Asp Pro Glu Ala Glu Val Pro
                725                 730                 735

Gly Gly Thr Leu Ser Pro Cys Asn Asn Leu Ser Pro Glu Asp His Ser
            740                 745                 750

Phe Leu Glu Asp Leu Ala Thr Tyr Glu Thr Ala Phe Glu Thr Gly Val
        755                 760                 765
```

-continued

Ser Thr Phe Pro Tyr Glu Gly Phe Ala Asp Glu Leu His Gln Leu Gln
    770                 775                 780

Ser Gln Val Gln Asp Ser Phe His Glu Asp Gly Ser Gly Glu Pro
785                 790                 795                 800

Thr Phe
    802

<210> SEQ ID NO 3
<211> LENGTH: 802
<212> TYPE: PRT
<213> ORGANISM: Rattus norvegicus

<400> SEQUENCE: 3

Met Tyr Arg Ser Thr Lys Gly Ala Ser Lys Ala Arg Arg Asp Gln Ile
  1               5                  10                  15

Asn Ala Glu Ile Arg Asn Leu Lys Glu Leu Leu Pro Leu Ala Glu Ala
                 20                  25                  30

Asp Lys Val Arg Leu Ser Tyr Leu His Ile Met Ser Leu Ala Cys Ile
             35                  40                  45

Tyr Thr Arg Lys Gly Val Phe Phe Ala Gly Gly Thr Pro Leu Ala Gly
 50                  55                  60

Pro Thr Gly Leu Leu Ser Ala Gln Glu Leu Glu Asp Ile Val Ala Ala
 65                  70                  75                  80

Leu Pro Gly Phe Leu Val Phe Thr Ala Glu Gly Lys Leu Leu Tyr
                 85                  90                  95

Leu Ser Glu Ser Val Ser Glu His Leu Gly His Ser Met Val Asp Leu
                100                 105                 110

Val Ala Gln Gly Asp Ser Ile Tyr Asp Ile Ile Asp Pro Ala Asp His
            115                 120                 125

Leu Thr Val Arg Gln Gln Leu Thr Met Pro Ser Ala Leu Asp Ala Asp
130                 135                 140

Arg Leu Phe Arg Cys Arg Phe Asn Thr Ser Lys Ser Leu Arg Arg Gln
145                 150                 155                 160

Ser Ala Gly Asn Lys Leu Val Leu Ile Arg Gly Arg Phe His Ala His
                165                 170                 175

Pro Pro Gly Ala Tyr Trp Ala Gly Asn Pro Val Phe Thr Ala Phe Cys
            180                 185                 190

Ala Pro Leu Glu Pro Arg Pro Arg Pro Gly Pro Gly Pro Gly Pro Gly
        195                 200                 205

Pro Gly Pro Ala Ser Leu Phe Leu Ala Met Phe Gln Ser Arg His Ala
    210                 215                 220

Lys Asp Leu Ala Leu Leu Asp Ile Ser Glu Ser Val Leu Ile Tyr Leu
225                 230                 235                 240

Gly Phe Glu Arg Ser Glu Leu Leu Cys Lys Ser Trp Tyr Gly Leu Leu
                245                 250                 255

His Pro Glu Asp Leu Ala His Ala Ser Ser Gln His Tyr Arg Leu Leu
            260                 265                 270

Ala Glu Asn Gly Asp Ile Gln Ala Glu Met Val Val Arg Leu Gln Ala
        275                 280                 285

Lys His Gly Gly Trp Thr Trp Ile Tyr Cys Met Leu Tyr Ser Asp Gly
    290                 295                 300

Pro Glu Gly Pro Ile Thr Ala Asn Asn Tyr Pro Ile Ser Asp Thr Glu
305                 310                 315                 320

Ala Trp Ser Leu Arg Gln Gln Leu Asn Ser Glu Asn Thr Gln Ala Ala

```
                   325                 330                 335
Tyr Val Leu Gly Thr Pro Ala Val Leu Pro Ser Phe Ser Glu Asn Val
                340                 345                 350
Phe Ser Gln Glu His Cys Ser Asn Pro Leu Phe Thr Pro Ala Leu Gly
                355                 360                 365
Thr Pro Arg Ser Ala Ser Phe Pro Arg Ala Pro Glu Leu Gly Val Ile
            370                 375                 380
Ser Thr Ser Glu Glu Leu Ala Gln Pro Ser Lys Glu Leu Asp Phe Ser
385                 390                 395                 400
Tyr Leu Pro Phe Pro Ala Arg Pro Glu Pro Ser Leu Gln Ala Asp Leu
                405                 410                 415
Ser Lys Asp Leu Val Cys Thr Pro Pro Tyr Thr Pro His Gln Pro Gly
                420                 425                 430
Gly Cys Ala Phe Leu Phe Ser Leu His Glu Pro Phe Gln Thr His Leu
                435                 440                 445
Pro Pro Pro Ser Ser Ser Leu Gln Glu Gln Leu Thr Pro Ser Thr Val
                450                 455                 460
Thr Phe Ser Glu Gln Leu Thr Pro Ser Ser Ala Thr Phe Pro Asp Pro
465                 470                 475                 480
Leu Thr Ser Ser Leu Gln Gly Gln Leu Thr Glu Ser Ser Ala Arg Ser
                485                 490                 495
Phe Glu Glu Gln Leu Thr Pro Cys Thr Ser Thr Phe Pro Asp Gln Leu
                500                 505                 510
Leu Pro Ser Thr Ala Thr Phe Pro Glu Pro Leu Gly Ser Pro Thr His
                515                 520                 525
Glu Gln Leu Thr Pro Pro Ser Thr Ala Phe Gln Ala His Leu Asn Ser
                530                 535                 540
Pro Ser Gln Thr Phe Pro Glu Gln Leu Ser Pro Asn Pro Thr Lys Thr
545                 550                 555                 560
Tyr Phe Ala Gln Glu Gly Cys Ser Phe Leu Tyr Glu Lys Leu Pro Pro
                565                 570                 575
Ser Pro Ser Ser Pro Gly Asn Gly Asp Cys Thr Leu Leu Ala Leu Ala
                580                 585                 590
Gln Leu Arg Gly Pro Leu Ser Val Asp Val Pro Leu Val Pro Glu Gly
                595                 600                 605
Leu Leu Thr Pro Glu Ala Ser Pro Val Lys Gln Ser Phe Phe His Tyr
                610                 615                 620
Thr Glu Lys Glu Gln Asn Glu Ile Asp Arg Leu Ile Gln Gln Ile Ser
625                 630                 635                 640
Gln Leu Ala Gln Gly Met Asp Arg Pro Phe Ser Ala Glu Ala Gly Thr
                645                 650                 655
Gly Gly Leu Glu Pro Leu Gly Leu Glu Pro Leu Asn Pro Asn Leu
                660                 665                 670
Ser Leu Ser Gly Ala Gly Pro Pro Val Leu Ser Leu Asp Leu Lys Pro
            675                 680                 685
Trp Lys Cys Gln Glu Leu Asp Phe Leu Val Asp Pro Asp Asn Leu Phe
            690                 695                 700
Leu Glu Glu Thr Pro Val Glu Asp Ile Phe Met Asp Leu Ser Thr Pro
705                 710                 715                 720
Asp Pro Asn Gly Glu Trp Gly Ser Gly Asp Pro Glu Ala Glu Val Pro
                725                 730                 735
Gly Gly Thr Leu Ser Pro Cys Asn Asn Leu Ser Pro Glu Asp His Ser
                740                 745                 750
```

```
Phe Leu Glu Asp Leu Ala Thr Tyr Glu Thr Ala Phe Glu Thr Gly Val
        755                 760                 765

Ser Thr Phe Pro Tyr Glu Gly Phe Ala Asp Glu Leu His Gln Leu Gln
        770                 775                 780

Ser Gln Val Gln Asp Ser Phe His Glu Asp Gly Ser Gly Gly Glu Pro
785                 790                 795                 800

Thr Phe
    802

<210> SEQ ID NO 4
<211> LENGTH: 3252
<212> TYPE: DNA
<213> ORGANISM: Homo sapiens
<220> FEATURE:
<221> NAME/KEY: CDS
<222> LOCATION: (102)..(2510)

<400> SEQUENCE: 4
tgagcgagag acggggaagc acggaggagg aagccgccgg tgcgtcggga cgggagcgca       60
ggtgctcggg cacccgagct ggagctccgc agccgccggt c atg tac cgc tcc acc      116
                                             Met Tyr Arg Ser Thr
                                               1               5 aag ggc gcc tcc aag gcg cgc cgg gac cag atc aac gcc gag atc cgg        164
Lys Gly Ala Ser Lys Ala Arg Arg Asp Gln Ile Asn Ala Glu Ile Arg
         10                  15                  20 aac ctc aag gag ctg ctg ccg ctg gcc gaa gcg gac aag gtc cgg ctg        212
Asn Leu Lys Glu Leu Leu Pro Leu Ala Glu Ala Asp Lys Val Arg Leu
             25                  30                  35 tcc tac ctg cac atc atg agc ctc gcc tgc atc tac act cgc aag ggc        260
Ser Tyr Leu His Ile Met Ser Leu Ala Cys Ile Tyr Thr Arg Lys Gly
         40                  45                  50 gtc ttc ttc gct ggt ggc act cct ctg gcg ggc ccc acg ggg ctt ctc        308
Val Phe Phe Ala Gly Gly Thr Pro Leu Ala Gly Pro Thr Gly Leu Leu
     55                  60                  65 tca gct caa gag ctt gag gac atc gta gcg gca cta ccc ggc ttt ctg        356
Ser Ala Gln Glu Leu Glu Asp Ile Val Ala Ala Leu Pro Gly Phe Leu
 70                  75                  80                  85 ctt gtg ttc aca gcc gag ggg aaa ttg ctc tac ctg tct gag agt gtg        404
Leu Val Phe Thr Ala Glu Gly Lys Leu Leu Tyr Leu Ser Glu Ser Val
                 90                  95                 100 agc gag cat ctg ggc cac tcc atg gtg gac ctg gtt gcc cag ggt gac        452
Ser Glu His Leu Gly His Ser Met Val Asp Leu Val Ala Gln Gly Asp
             105                 110                 115 agc atc tac gac atc att gac cca gct gac cac ctc act gtg cgc cag        500
Ser Ile Tyr Asp Ile Ile Asp Pro Ala Asp His Leu Thr Val Arg Gln
         120                 125                 130 caa ctc acc ctg ccc tct gcc ctg gac act gat cgc ctc ttc cgc tgc        548
Gln Leu Thr Leu Pro Ser Ala Leu Asp Thr Asp Arg Leu Phe Arg Cys
     135                 140                 145 cgc ttc aac acc tcc aag tcc ctc agg cgc cag agt gca ggc aac aaa        596
Arg Phe Asn Thr Ser Lys Ser Leu Arg Arg Gln Ser Ala Gly Asn Lys
150                 155                 160                 165 ctc gtg ctt att cga ggc cga ttc cat gct cac cca cct gga gcc tac        644
Leu Val Leu Ile Arg Gly Arg Phe His Ala His Pro Pro Gly Ala Tyr
                 170                 175                 180 tgg gca gga aat ccc gtg ttc aca gct ttc tgt gcc cct ctg gag ccg        692
Trp Ala Gly Asn Pro Val Phe Thr Ala Phe Cys Ala Pro Leu Glu Pro
             185                 190                 195 aga ccc cgc cca ggt cct ggc cct ggc cct ggc cct gcc tcg ctc ttc        740
```

-continued

| | | |
|---|---|---|
| Arg Pro Arg Pro Gly Pro Gly Pro Gly Pro Ala Ser Leu Phe<br>200 205 210 | | |
| ctg gcc atg ttc cag agc cgc cat gct aaa gac ctg gct cta ctg gac<br>Leu Ala Met Phe Gln Ser Arg His Ala Lys Asp Leu Ala Leu Leu Asp<br>215 220 225 | 788 | |
| atc tcc gag agt gtc cta atc tac ctg ggc ttt gag cgc agt gaa ctg<br>Ile Ser Glu Ser Val Leu Ile Tyr Leu Gly Phe Glu Arg Ser Glu Leu<br>230 235 240 245 | 836 | |
| ctt tgt aaa tca tgg tat gga ctg ctg cac ccc gag gac ctg gcc cac<br>Leu Cys Lys Ser Trp Tyr Gly Leu Leu His Pro Glu Asp Leu Ala His<br>250 255 260 | 884 | |
| gct tct gct caa cac tac cgc ctg ttg gct gag agt gga gat att cag<br>Ala Ser Ala Gln His Tyr Arg Leu Leu Ala Glu Ser Gly Asp Ile Gln<br>265 270 275 | 932 | |
| gca gag atg gtg gtg agg cta cag gcc aag act gga ggc tgg gca tgg<br>Ala Glu Met Val Val Arg Leu Gln Ala Lys Thr Gly Gly Trp Ala Trp<br>280 285 290 | 980 | |
| att tac tgc ctg tta tac tca gaa ggt cca gag gga ccc att act gcc<br>Ile Tyr Cys Leu Leu Tyr Ser Glu Gly Pro Glu Gly Pro Ile Thr Ala<br>295 300 305 | 1028 | |
| aat aac tac cca atc agt gac atg gaa gcc tgg agc ctc cgc cag cag<br>Asn Asn Tyr Pro Ile Ser Asp Met Glu Ala Trp Ser Leu Arg Gln Gln<br>310 315 320 325 | 1076 | |
| ttg aac tct gaa gac acc cag gca gct tat gtc ctg ggc act ccg acc<br>Leu Asn Ser Glu Asp Thr Gln Ala Ala Tyr Val Leu Gly Thr Pro Thr<br>330 335 340 | 1124 | |
| atg ctg ccc tca ttc cct gaa aac att ctt tcc cag gaa gag tgc tcc<br>Met Leu Pro Ser Phe Pro Glu Asn Ile Leu Ser Gln Glu Glu Cys Ser<br>345 350 355 | 1172 | |
| agc act aac cca ctc ttc acc gca gca ctg ggg gct ccc aga agc acc<br>Ser Thr Asn Pro Leu Phe Thr Ala Ala Leu Gly Ala Pro Arg Ser Thr<br>360 365 370 | 1220 | |
| agc ttc ccc agt gct cct gaa ctg agt gtt gtc tct gca tca gaa gag<br>Ser Phe Pro Ser Ala Pro Glu Leu Ser Val Val Ser Ala Ser Glu Glu<br>375 380 385 | 1268 | |
| ctt ccc cga ccc tcc aaa gaa ctg gac ttc agt tac ctg aca ttc cct<br>Leu Pro Arg Pro Ser Lys Glu Leu Asp Phe Ser Tyr Leu Thr Phe Pro<br>390 395 400 405 | 1316 | |
| tct ggg cct gag cct tct ctc caa gca gaa cta agc aag gat ctt gtg<br>Ser Gly Pro Glu Pro Ser Leu Gln Ala Glu Leu Ser Lys Asp Leu Val<br>410 415 420 | 1364 | |
| tgc act cca cct tac acg ccc cat cag cca gga ggc tgt gcc ttc ctc<br>Cys Thr Pro Pro Tyr Thr Pro His Gln Pro Gly Gly Cys Ala Phe Leu<br>425 430 435 | 1412 | |
| ttc agc ctc cat gag ccc ttc cag acc cat ttg ccc acc cca tcc agc<br>Phe Ser Leu His Glu Pro Phe Gln Thr His Leu Pro Thr Pro Ser Ser<br>440 445 450 | 1460 | |
| act ctt caa gaa cag ctg act cca agc act gcg acc ttc tct gat cag<br>Thr Leu Gln Glu Gln Leu Thr Pro Ser Thr Ala Thr Phe Ser Asp Gln<br>455 460 465 | 1508 | |
| ttg acg ccc agc agt gca acc ttc cca gat cca cta act agc cca ctg<br>Leu Thr Pro Ser Ser Ala Thr Phe Pro Asp Pro Leu Thr Ser Pro Leu<br>470 475 480 485 | 1556 | |
| caa ggc cag ttg act gaa acc tcg gtc aga agc tat gaa gac cag ttg<br>Gln Gly Gln Leu Thr Glu Thr Ser Val Arg Ser Tyr Glu Asp Gln Leu<br>490 495 500 | 1604 | |
| act ccc tgc acc tcc acc ttc cca gac cag ctg ctt ccc agc aca gcc<br>Thr Pro Cys Thr Ser Thr Phe Pro Asp Gln Leu Leu Pro Ser Thr Ala<br>505 510 515 | 1652 | |

```
acc ttc cca gag cct ctg ggc agc cct gcc cat gaa cag ctg act cct      1700
Thr Phe Pro Glu Pro Leu Gly Ser Pro Ala His Glu Gln Leu Thr Pro
        520                 525                 530 ccc agc aca gca ttc caa gca cac ctg gac agc ccc agc caa acc ttc      1748
Pro Ser Thr Ala Phe Gln Ala His Leu Asp Ser Pro Ser Gln Thr Phe
535                 540                 545 cca gag caa ctg agc ccc aac cct acc aag act tac ttt gcc cag gag      1796
Pro Glu Gln Leu Ser Pro Asn Pro Thr Lys Thr Tyr Phe Ala Gln Glu
550                 555                 560                 565 gga tgc agt ttt ctc tat gag aag ttg ccc cca agt cct agc agc cct      1844
Gly Cys Ser Phe Leu Tyr Glu Lys Leu Pro Pro Ser Pro Ser Ser Pro
                570                 575                 580 ggt aat ggg gac tgc acg ctc ttg gcc cta gcc cag ctc cgg ggc ccc      1892
Gly Asn Gly Asp Cys Thr Leu Leu Ala Leu Ala Gln Leu Arg Gly Pro
            585                 590                 595 ctc tct gtg gat gtc ccc ctg gtg ccc gaa ggc ctg ctc aca cct gag      1940
Leu Ser Val Asp Val Pro Leu Val Pro Glu Gly Leu Leu Thr Pro Glu
        600                 605                 610 gcc tct cca gtc aag cag agt ttc ttc cac tac tct gaa aag gag cag      1988
Ala Ser Pro Val Lys Gln Ser Phe Phe His Tyr Ser Glu Lys Glu Gln
615                 620                 625 aat gag ata gac cgt ctc atc cag cag att agc caa ttg gct cag ggc      2036
Asn Glu Ile Asp Arg Leu Ile Gln Gln Ile Ser Gln Leu Ala Gln Gly
630                 635                 640                 645 atg gac aga ccc ttc tca gct gag gct ggc act ggc gga cta gag cca      2084
Met Asp Arg Pro Phe Ser Ala Glu Ala Gly Thr Gly Gly Leu Glu Pro
                650                 655                 660 ctt gga gga ctg gag ccc ctg gac tcc aac ctg tcc ctg tca ggg gca      2132
Leu Gly Gly Leu Glu Pro Leu Asp Ser Asn Leu Ser Leu Ser Gly Ala
            665                 670                 675 ggc ccc cct gtg ctc agc ctg gac ctg aaa ccc tgg aaa tgc agg gag      2180
Gly Pro Pro Val Leu Ser Leu Asp Leu Lys Pro Trp Lys Cys Gln Glu
        680                 685                 690 ctg gac ttc ctg gct gac cct gat aac atg ttc ctg gaa gag acg ccc      2228
Leu Asp Phe Leu Ala Asp Pro Asp Asn Met Phe Leu Glu Glu Thr Pro
695                 700                 705 gtg gaa gac atc ttc atg gat ctc tct acc cca gat ccc agt gag gaa      2276
Val Glu Asp Ile Phe Met Asp Leu Ser Thr Pro Asp Pro Ser Glu Glu
710                 715                 720                 725 tgg ggc tca ggg gat cct gag gca gag ggc cca gga ggg gcc cca tcg      2324
Trp Gly Ser Gly Asp Pro Glu Ala Glu Gly Pro Gly Gly Ala Pro Ser
                730                 735                 740 cct tgc aac aac ctg tcc cca gaa gac cac agc ttc ctg gag gac ctg      2372
Pro Cys Asn Asn Leu Ser Pro Glu Asp His Ser Phe Leu Glu Asp Leu
            745                 750                 755 gcc aca tat gaa acc gcc ttt gag aca ggt gtc tca gca ttc ccc tat      2420
Ala Thr Tyr Glu Thr Ala Phe Glu Thr Gly Val Ser Ala Phe Pro Tyr
        760                 765                 770 gat ggg ttt act gat gag ttg cat caa ctc cag agc caa gtt caa gac      2468
Asp Gly Phe Thr Asp Glu Leu His Gln Leu Gln Ser Gln Val Gln Asp
775                 780                 785 agc ttc cat gaa gat gga agt gga ggg gaa cca acg ttt tga              2510
Ser Phe His Glu Asp Gly Ser Gly Gly Glu Pro Thr Phe
790                 795                 800 ataagtctgt gacttaacgt cgtcaagtat ggcatattgt catcaagacg tggagccgct    2570
ctccaccccc ccgggactgt gggggggatt ctgagggcca gaggggata tatatgattc     2630 cccaggccct gcaggatttt ggggggggggg agtgggagg gcaagggagg ggagcttctt    2690
tttaaaatca agagacttcg agcgatccca gtttccattt caatctgtat tcactcgtag   2750
```

-continued

```
tgagtttcct tgaatgggat ttcaagcgga gaatggggga gtctcacttc cccgccgcct      2810
tgccccattg gcctgggcca gttctccact cctagggggcc aagccacccc tagccttggt     2870 ggggaaagg cagggcccac ccgggccagc cgtgccctg aggggctctt gacacccacg        2930
tagaattctc tacacaccag taacgggatt tcaattccga tggactctgc cgccctggcg      2990
gcccttcctg tgacttttgc gccccgcgcc tggggtgggg ggtgcgaaaa aacgctacgt      3050
tcctttccga tggaggaagg cagacctgcc gtcacacgtg tgcttgcacg agtgcgtgta     3110
cctggtgcgg gactcacccg gccgccagac tgcctgggcc tgcccaaatg gccacctcgg     3170
tggtgctgcg gtgactttgt agccaacttt ataataaagt ccagtttgcc ttttggtaa      3230 aaaaaaaaaa aaaaaaaaa aa                                               3252
```

<210> SEQ ID NO 5
<211> LENGTH: 3087
<212> TYPE: DNA
<213> ORGANISM: Mus musculus
<220> FEATURE:
<221> NAME/KEY: CDS
<222> LOCATION: (51)...(2459)

<400> SEQUENCE: 5

```
aggatcgcag gtgctcggga gccggagctg gagctccaca gccggcagtc atg tac         56
                                                      Met Tyr
                                                        1 cga tcc acc aag ggc gcc tcc aag gcg cgc cgc gac cag atc aac gcc       104
Arg Ser Thr Lys Gly Ala Ser Lys Ala Arg Arg Asp Gln Ile Asn Ala
         5                  10                  15 gag att cgg aac ctc aag gag ctg ctg ccg ttg gct gaa gcg gac aag       152
Glu Ile Arg Asn Leu Lys Glu Leu Leu Pro Leu Ala Glu Ala Asp Lys
     20                  25                  30 gtc cgg ctg tcc tac ctg cac atc atg agt ctt gcc tgc atc tac act       200
Val Arg Leu Ser Tyr Leu His Ile Met Ser Leu Ala Cys Ile Tyr Thr
 35                  40                  45                  50 cgc aag ggt gtc ttc ttt gct gga ggc act cct ttg gct ggc ccc acc       248
Arg Lys Gly Val Phe Phe Ala Gly Gly Thr Pro Leu Ala Gly Pro Thr
                 55                  60                  65 ggg ctt ctc tct gct caa gag ctt gaa gac att gtg gca gca cta cct       296
Gly Leu Leu Ser Ala Gln Glu Leu Glu Asp Ile Val Ala Ala Leu Pro
             70                  75                  80 gga ttt ctc ctt gta ttc aca gct gag ggg aag ttg cta tac ctg tcg      344
Gly Phe Leu Leu Val Phe Thr Ala Glu Gly Lys Leu Leu Tyr Leu Ser
         85                  90                  95 gag agt gtg agc gag cat ctg ggc cac tct atg gtg gac ctg gtt gcc      392
Glu Ser Val Ser Glu His Leu Gly His Ser Met Val Asp Leu Val Ala
    100                 105                 110 cag ggc gac agt atc tac gat atc att gac cct gct gac cat ctc act      440
Gln Gly Asp Ser Ile Tyr Asp Ile Ile Asp Pro Ala Asp His Leu Thr
115                 120                 125                 130 gtg cgc cag cag ctc acc atg ccc tct gct ctg gat gct gat cgc ctt      488
Val Arg Gln Gln Leu Thr Met Pro Ser Ala Leu Asp Ala Asp Arg Leu
                135                 140                 145 ttc cgt tgt cga ttc aac acc tcc aag tcc ctc cgg cgc cag agt tca      536
Phe Arg Cys Arg Phe Asn Thr Ser Lys Ser Leu Arg Arg Gln Ser Ser
            150                 155                 160 gga aac aaa ctg gtg ctt att cga ggt cga ttc cat gct cac cca cct      584
Gly Asn Lys Leu Val Leu Ile Arg Gly Arg Phe His Ala His Pro Pro
        165                 170                 175 ggg gcc tac tgg gca gga aac cct gtg ttc acc gct ttc tgc gcc cca      632
```

```
                Gly Ala Tyr Trp Ala Gly Asn Pro Val Phe Thr Ala Phe Cys Ala Pro
                    180                 185                 190 ctg gag cca aga ccc cgc cct ggc ccc ggc cct ggc cct ggt              680
Leu Glu Pro Arg Pro Arg Pro Gly Pro Gly Pro Gly Pro Gly
195                 200                 205                 210 cct gct tct ctc ttc ctg gcc atg ttc cag agc cgg cat gct aag gac      728
Pro Ala Ser Leu Phe Leu Ala Met Phe Gln Ser Arg His Ala Lys Asp
                    215                 220                 225 cta gcc cta ctg gac gtt tct gaa agt gtc cta atc tac ctg ggc ttt      776
Leu Ala Leu Leu Asp Val Ser Glu Ser Val Leu Ile Tyr Leu Gly Phe
                230                 235                 240 gag cgc agc gaa ctg ctc tgt aaa tca tgg tat gga ctg cta cac ccc      824
Glu Arg Ser Glu Leu Leu Cys Lys Ser Trp Tyr Gly Leu Leu His Pro
            245                 250                 255 gag gac ctg gcc caa gct tct tct caa cac tac cgc ctg ttg gct gaa      872
Glu Asp Leu Ala Gln Ala Ser Ser Gln His Tyr Arg Leu Leu Ala Glu
        260                 265                 270 agt gga gat att cag gct gaa atg gtg gtg aga ctt caa gcc aag cat      920
Ser Gly Asp Ile Gln Ala Glu Met Val Val Arg Leu Gln Ala Lys His
275                 280                 285                 290 gga ggc tgg aca tgg att tac tgc atg cta tac tca gaa ggt cca gaa      968
Gly Gly Trp Thr Trp Ile Tyr Cys Met Leu Tyr Ser Glu Gly Pro Glu
                295                 300                 305 ggc cct ttt act gcc aat aac tac cct atc agt gac acg gaa gcc tgg     1016
Gly Pro Phe Thr Ala Asn Asn Tyr Pro Ile Ser Asp Thr Glu Ala Trp
                    310                 315                 320 agc ctc cgc cag cag cta aac tct gaa gac acc cag gca gcc tat gtc     1064
Ser Leu Arg Gln Gln Leu Asn Ser Glu Asp Thr Gln Ala Ala Tyr Val
                325                 330                 335 cta gga acc cca gct gtg cta ccc tca ttc tct gag aat gtc ttc tcc     1112
Leu Gly Thr Pro Ala Val Leu Pro Ser Phe Ser Glu Asn Val Phe Ser
            340                 345                 350 cag gag caa tgc tct aat cca ctc ttt aca cca tcc ctg ggg act cct     1160
Gln Glu Gln Cys Ser Asn Pro Leu Phe Thr Pro Ser Leu Gly Thr Pro
355                 360                 365                 370 aga agt gcc agc ttc ccc agg gct cct gaa cta ggt gtg atc tca aca     1208
Arg Ser Ala Ser Phe Pro Arg Ala Pro Glu Leu Gly Val Ile Ser Thr
                375                 380                 385 cca gaa gag ctt ccc caa ccc tcc aaa gag ctg gac ttc agt tac ctg     1256
Pro Glu Glu Leu Pro Gln Pro Ser Lys Glu Leu Asp Phe Ser Tyr Leu
                    390                 395                 400 cca ttc cct gct agg cct gag cct tcc ctc caa gca gac ctg agc aag     1304
Pro Phe Pro Ala Arg Pro Glu Pro Ser Leu Gln Ala Asp Leu Ser Lys
                405                 410                 415 gat ttg gtg tgt act cca cct tac aca ccc cac cag cca gga ggc tgt     1352
Asp Leu Val Cys Thr Pro Pro Tyr Thr Pro His Gln Pro Gly Gly Cys
420                 425                 430 gcc ttc ctc ttc agc ctc cat gaa ccc ttc cag act cac ttg ccc cct     1400
Ala Phe Leu Phe Ser Leu His Glu Pro Phe Gln Thr His Leu Pro Pro
435                 440                 445                 450 ccg tcc agc tct ctc caa gaa cag ctg aca cca agt aca gtg act ttc     1448
Pro Ser Ser Ser Leu Gln Glu Gln Leu Thr Pro Ser Thr Val Thr Phe
                455                 460                 465 tct gaa cag ttg aca ccc agc agt gct acc ttc cca gac cca cta acc     1496
Ser Glu Gln Leu Thr Pro Ser Ser Ala Thr Phe Pro Asp Pro Leu Thr
                470                 475                 480 agt tca cta caa gga cag ttg aca gaa agc tca gcc aga agc ttt gaa     1544
Ser Ser Leu Gln Gly Gln Leu Thr Glu Ser Ser Ala Arg Ser Phe Glu
            485                 490                 495
```

```
gac cag ttg act cca tgc acc tct tcc ttc cct gac cag cta ctt ccc        1592
Asp Gln Leu Thr Pro Cys Thr Ser Ser Phe Pro Asp Gln Leu Leu Pro
500                 505                 510 agc act gcc aca ttc cca gag cct ctg ggc agc ccc gcc cat gag cag        1640
Ser Thr Ala Thr Phe Pro Glu Pro Leu Gly Ser Pro Ala His Glu Gln
515                 520                 525                 530 ctg act cct ccc agc aca gca ttc cag gct cat ctg aac agc ccc agc        1688
Leu Thr Pro Pro Ser Thr Ala Phe Gln Ala His Leu Asn Ser Pro Ser
                535                 540                 545 caa acc ttc cca gag caa ctg agc ccc aat cct acc aag act tac ttc        1736
Gln Thr Phe Pro Glu Gln Leu Ser Pro Asn Pro Thr Lys Thr Tyr Phe
    550                 555                 560 gcc cag gag gga tgc agt ttt ctc tat gag aag ttg ccc cca agt cct        1784
Ala Gln Glu Gly Cys Ser Phe Leu Tyr Glu Lys Leu Pro Pro Ser Pro
565                 570                 575 agc agc cct ggt aat ggg gac tgt aca ctc ctg gcc cta gct cag ctc        1832
Ser Ser Pro Gly Asn Gly Asp Cys Thr Leu Leu Ala Leu Ala Gln Leu
        580                 585                 590 cgg ggc ccc ctc tct gtg gat gtc ccc ctg gtg ccc gaa ggc ctg ctc        1880
Arg Gly Pro Leu Ser Val Asp Val Pro Leu Val Pro Glu Gly Leu Leu
595                 600                 605                 610 aca cct gag gcc tct cca gtc aag caa agt ttc ttc cac tac aca gag        1928
Thr Pro Glu Ala Ser Pro Val Lys Gln Ser Phe Phe His Tyr Thr Glu
                615                 620                 625 aaa gag caa aat gag ata gat cgt ctc att cag cag atc agc cag ttg        1976
Lys Glu Gln Asn Glu Ile Asp Arg Leu Ile Gln Gln Ile Ser Gln Leu
    630                 635                 640 gct cag ggc gtg gac agg ccc ttc tca gct gag gct ggc act ggg ggg        2024
Ala Gln Gly Val Asp Arg Pro Phe Ser Ala Glu Ala Gly Thr Gly Gly
645                 650                 655 ctg gag cca ctt gga ggg ctg gag ccc ctg aac cct aac ctg tcc ctg        2072
Leu Glu Pro Leu Gly Gly Leu Glu Pro Leu Asn Pro Asn Leu Ser Leu
        660                 665                 670 tca ggg gct gga ccc cct gtg ctt agc ctg gat ctt aaa ccc tgg aaa        2120
Ser Gly Ala Gly Pro Pro Val Leu Ser Leu Asp Leu Lys Pro Trp Lys
675                 680                 685                 690 tgc cag gag ctg gac ttc ctg gtt gac cct gat aat tta ttc ctg gaa        2168
Cys Gln Glu Leu Asp Phe Leu Val Asp Pro Asp Asn Leu Phe Leu Glu
                695                 700                 705 gag acg cca gtg gaa gac atc ttc atg gat ctt tct act cca gac ccc        2216
Glu Thr Pro Val Glu Asp Ile Phe Met Asp Leu Ser Thr Pro Asp Pro
    710                 715                 720 aat ggg gaa tgg ggt tca ggg gat cct gag gca gag gtc cca gga ggg        2264
Asn Gly Glu Trp Gly Ser Gly Asp Pro Glu Ala Glu Val Pro Gly Gly
725                 730                 735 acc ctg tca cct tgc aac aac ctg tcc cca gaa gat cac agc ttc ctg        2312
Thr Leu Ser Pro Cys Asn Asn Leu Ser Pro Glu Asp His Ser Phe Leu
        740                 745                 750 gag gac ttg gcc acc tat gaa acc gcc ttt gag aca ggt gtc tca aca        2360
Glu Asp Leu Ala Thr Tyr Glu Thr Ala Phe Glu Thr Gly Val Ser Thr
755                 760                 765                 770 ttc ccc tac gaa ggg ttt gct gat gag ttg cat caa ctc cag agc caa        2408
Phe Pro Tyr Glu Gly Phe Ala Asp Glu Leu His Gln Leu Gln Ser Gln
                775                 780                 785 gtt caa gac agc ttc cat gaa gat gga agt gga ggg gaa cca acg ttt        2456
Val Gln Asp Ser Phe His Glu Asp Gly Ser Gly Gly Glu Pro Thr Phe
    790                 795                 800 tga ataagtctgt gacttaacgt cttcaagtat ggcatattgt catcaagacg tggagc      2515 cgctctccac cccccgggac tgttgggggg gattctgggg gccagagggg gatatatctg      2575
```

-continued

```
attctccagg ccctgaagga tttagggggg aggtgggagg gtaagggagg ggagcaactt      2635
tttaaaatca agagacttcg agcgatccca gtttccattt caatctgtat tcactcgtag      2695
tgagtttcct tgaatggatt tcaagcggag aatgggggag tctcacttcc tcaccgcgct      2755
gccccatggg cctgggccag ttctccactc ctaggggcaa agccacccct gggctttggt      2815
gggggaaagg catggcccac ctggggctag cctgtgcccc gagggctct tgacacccac       2875 gtagaattct ctacaaacca gtaacgggat ttcaattccg acggactctg ccgccctggc      2935
ggctcttcct gtgactttg cgccccgcgc ctggggtggg gggcgcgaag agacgctaca       2995
ttcctttccg atggaggaag gcagatctgc cgtcacacgt gtgcttgcac gagtgcgtgt      3055
acctggtgcg ggactcaccc ggccgccaga cc                                    3087
```

<210> SEQ ID NO 6
<211> LENGTH: 2459
<212> TYPE: DNA
<213> ORGANISM: Rattus norvegicus
<220> FEATURE:
<221> NAME/KEY: CDS
<222> LOCATION: (35)...(2443)

<400> SEQUENCE: 6

```
gggagccgga gctggagctc cacggccggc agtc atg tac cga tcc acc aag ggc        55
                                    Met Tyr Arg Ser Thr Lys Gly
                                      1               5 gcc tcc aag gcg cgc cgc gac cag atc aac gcc gag att cgg aac ctc         103
Ala Ser Lys Ala Arg Arg Asp Gln Ile Asn Ala Glu Ile Arg Asn Leu
         10                  15                  20 aag gaa ctg ctg ccg ttg gct gaa gcg gac aag gtc cgg ctg tcc tac         151
Lys Glu Leu Leu Pro Leu Ala Glu Ala Asp Lys Val Arg Leu Ser Tyr
 25                  30                  35 ctg cac atc atg agt ctt gcc tgc atc tac act cgc aag ggt gtc ttc         199
Leu His Ile Met Ser Leu Ala Cys Ile Tyr Thr Arg Lys Gly Val Phe
 40                  45                  50                  55 ttt gct gga ggc act cct ttg gct ggc ccc acg ggg ctt ctc tct gct         247
Phe Ala Gly Gly Thr Pro Leu Ala Gly Pro Thr Gly Leu Leu Ser Ala
                 60                  65                  70 caa gag ctt gaa gac ata gtg gca gca cta cct gga ttt cta ctt gtg         295
Gln Glu Leu Glu Asp Ile Val Ala Ala Leu Pro Gly Phe Leu Leu Val
         75                  80                  85 ttc aca gct gag ggg aag ttg cta tac ctg tcg gag agt gtg agc gag         343
Phe Thr Ala Glu Gly Lys Leu Leu Tyr Leu Ser Glu Ser Val Ser Glu
 90                  95                 100 cat ctg ggc cat tct atg gtg gat ctg gtt gcc cag ggt gac agt att         391
His Leu Gly His Ser Met Val Asp Leu Val Ala Gln Gly Asp Ser Ile
105                 110                 115 tac gac atc att gac cct gct gac cat ctc act gtg cgc cag cag ctc         439
Tyr Asp Ile Ile Asp Pro Ala Asp His Leu Thr Val Arg Gln Gln Leu
120                 125                 130                 135 acc atg ccc tct gct ctg gat gct gat cgc ctt ttc cgt tgt cga ttt         487
Thr Met Pro Ser Ala Leu Asp Ala Asp Arg Leu Phe Arg Cys Arg Phe
                140                 145                 150 aac aca tcc aag tcc ctc cgg cgc cag agt gca ggc aac aaa ctg gtg         535
Asn Thr Ser Lys Ser Leu Arg Arg Gln Ser Ala Gly Asn Lys Leu Val
        155                 160                 165 ctt att cga ggt cga ttc cat gct cac cca cct ggg gcc tac tgg gca         583
Leu Ile Arg Gly Arg Phe His Ala His Pro Pro Gly Ala Tyr Trp Ala
170                 175                 180 gga aac ccc gtg ttc aca gct ttc tgt gcc cca ctg gag cca aga ccc         631
```

```
                Gly Asn Pro Val Phe Thr Ala Phe Cys Ala Pro Leu Glu Pro Arg Pro
                            185                 190                 195 cgt ccc ggc cct ggc cct ggc cct ggt cct gcc tct ctc ttc                     679
Arg Pro Gly Pro Gly Pro Gly Pro Gly Pro Ala Ser Leu Phe
200                 205                 210                 215 ctg gcc atg ttc cag agc cgg cat gct aag gac cta gcc cta ctg gac             727
Leu Ala Met Phe Gln Ser Arg His Ala Lys Asp Leu Ala Leu Leu Asp
                    220                 225                 230 att tct gaa agt gtc cta atc tac ctg ggc ttt gag cgc agc gaa ctg             775
Ile Ser Glu Ser Val Leu Ile Tyr Leu Gly Phe Glu Arg Ser Glu Leu
            235                 240                 245 ctc tgt aaa tca tgg tat gga ctg cta cac ccc gag gac ctg gcc cac             823
Leu Cys Lys Ser Trp Tyr Gly Leu Leu His Pro Glu Asp Leu Ala His
        250                 255                 260 gct tct tct caa cac tac cgc ctg ttg gct gaa aat gga gat att cag             871
Ala Ser Ser Gln His Tyr Arg Leu Leu Ala Glu Asn Gly Asp Ile Gln
    265                 270                 275 gct gaa atg gtg gtg aga ctt caa gcc aag cat gga ggc tgg aca tgg             919
Ala Glu Met Val Val Arg Leu Gln Ala Lys His Gly Gly Trp Thr Trp
280                 285                 290                 295 att tac tgc atg cta tac tcg gat ggt cca gaa ggc cct att act gcc             967
Ile Tyr Cys Met Leu Tyr Ser Asp Gly Pro Glu Gly Pro Ile Thr Ala
                    300                 305                 310 aat aac tac cct atc agt gac acg gaa gcc tgg agt ctt cgc cag cag            1015
Asn Asn Tyr Pro Ile Ser Asp Thr Glu Ala Trp Ser Leu Arg Gln Gln
            315                 320                 325 cta aac tct gaa aac acc cag gca gcc tat gtc cta gga acc cca gct            1063
Leu Asn Ser Glu Asn Thr Gln Ala Ala Tyr Val Leu Gly Thr Pro Ala
        330                 335                 340 gtg cta ccc tca ttc tct gag aat gtc ttc tcc cag gag cac tgc tct            1111
Val Leu Pro Ser Phe Ser Glu Asn Val Phe Ser Gln Glu His Cys Ser
    345                 350                 355 aat cca ctc ttt aca cca gcc ctg ggg act cct aga agt gcc agc ttc            1159
Asn Pro Leu Phe Thr Pro Ala Leu Gly Thr Pro Arg Ser Ala Ser Phe
360                 365                 370                 375 ccc agg gcc cct gaa cta ggt gtg atc tca aca tca gaa gag ctt gcc            1207
Pro Arg Ala Pro Glu Leu Gly Val Ile Ser Thr Ser Glu Glu Leu Ala
                    380                 385                 390 caa ccc tcc aaa gaa ctg gac ttc agt tac ctg cca ttc cct gca agg            1255
Gln Pro Ser Lys Glu Leu Asp Phe Ser Tyr Leu Pro Phe Pro Ala Arg
            395                 400                 405 cct gag cct tcc ctc caa gca gac ttg agc aag gat ttg gtg tgt act            1303
Pro Glu Pro Ser Leu Gln Ala Asp Leu Ser Lys Asp Leu Val Cys Thr
        410                 415                 420 cca cct tac aca ccc cac cag cca gga ggc tgc gcc ttc ctc ttc agc            1351
Pro Pro Tyr Thr Pro His Gln Pro Gly Gly Cys Ala Phe Leu Phe Ser
    425                 430                 435 ctc cat gaa ccc ttc cag act cac ttg ccc cct cca tcc agc tct ctc            1399
Leu His Glu Pro Phe Gln Thr His Leu Pro Pro Pro Ser Ser Ser Leu
440                 445                 450                 455 caa gaa cag ctg acg cca agc acg gtg act ttc tct gaa cag ttg aca            1447
Gln Glu Gln Leu Thr Pro Ser Thr Val Thr Phe Ser Glu Gln Leu Thr
                    460                 465                 470 cca agc agt gca acc ttc cca gat cca cta acc agt cta caa gga                1495
Pro Ser Ser Ala Thr Phe Pro Asp Pro Leu Thr Ser Leu Gln Gly
            475                 480                 485 cag ttg act gaa agc tca gcc aga agc ttt gaa gaa caa ttg act ccg            1543
Gln Leu Thr Glu Ser Ser Ala Arg Ser Phe Glu Glu Gln Leu Thr Pro
        490                 495                 500
```

-continued

```
tgc acc tct acc ttc cct gac cag ctg ctt ccc agc act gcc acg ttc      1591
Cys Thr Ser Thr Phe Pro Asp Gln Leu Leu Pro Ser Thr Ala Thr Phe
505                 510                 515 cca gaa cct ctg ggt agc ccc acc cat gag cag ctg act cct ccc agc      1639
Pro Glu Pro Leu Gly Ser Pro Thr His Glu Gln Leu Thr Pro Pro Ser
520                 525                 530                 535 aca gca ttc caa gca cat ctg aac agt cct agc caa acc ttc cca gag      1687
Thr Ala Phe Gln Ala His Leu Asn Ser Pro Ser Gln Thr Phe Pro Glu
                540                 545                 550 caa ctg agc cct aat cct acc aag act tac ttc gcc cag gag gga tgc      1735
Gln Leu Ser Pro Asn Pro Thr Lys Thr Tyr Phe Ala Gln Glu Gly Cys
        555                 560                 565 agt ttt ctc tat gag aag ttg ccc cca agt cct agc agc cct ggt aat      1783
Ser Phe Leu Tyr Glu Lys Leu Pro Pro Ser Pro Ser Ser Pro Gly Asn
    570                 575                 580 ggg gac tgt aca ctc ttg gcc cta gct caa ctc cgg ggt ccc ctc tct      1831
Gly Asp Cys Thr Leu Leu Ala Leu Ala Gln Leu Arg Gly Pro Leu Ser
585                 590                 595 gtg gac gtc ccc ctg gtg cct gaa ggc ctg ctc aca cct gag gcc tct      1879
Val Asp Val Pro Leu Val Pro Glu Gly Leu Leu Thr Pro Glu Ala Ser
600                 605                 610                 615 cca gtc aag caa agt ttc ttc cac tat aca gag aaa gag cag aat gag      1927
Pro Val Lys Gln Ser Phe Phe His Tyr Thr Glu Lys Glu Gln Asn Glu
                620                 625                 630 ata gat cgt ctc atc cag cag atc agc cag ttg gct cag ggc atg gac      1975
Ile Asp Arg Leu Ile Gln Gln Ile Ser Gln Leu Ala Gln Gly Met Asp
        635                 640                 645 agg ccc ttc tca gct gag gct ggc act ggg ggg ctg gag cca ctt gga      2023
Arg Pro Phe Ser Ala Glu Ala Gly Thr Gly Gly Leu Glu Pro Leu Gly
    650                 655                 660 ggg ctg gag ccc ctg aac ccc aac ctg tcc ctg tca ggg gct gga ccc      2071
Gly Leu Glu Pro Leu Asn Pro Asn Leu Ser Leu Ser Gly Ala Gly Pro
665                 670                 675 cct gtg ctt agc ctg gat ctt aaa ccc tgg aaa tgc cag gag ctg gac      2119
Pro Val Leu Ser Leu Asp Leu Lys Pro Trp Lys Cys Gln Glu Leu Asp
680                 685                 690                 695 ttc ttg gtt gac cct gat aat tta ttc ctg gaa gag acg cca gtg gaa      2167
Phe Leu Val Asp Pro Asp Asn Leu Phe Leu Glu Glu Thr Pro Val Glu
                700                 705                 710 gac atc ttc atg gat ctt tct act cca gac ccc aat ggg gaa tgg ggt      2215
Asp Ile Phe Met Asp Leu Ser Thr Pro Asp Pro Asn Gly Glu Trp Gly
        715                 720                 725 tca ggg gat cct gag gca gag gtc cca gga ggg acc ctg tca cct tgc      2263
Ser Gly Asp Pro Glu Ala Glu Val Pro Gly Gly Thr Leu Ser Pro Cys
    730                 735                 740 aac aac ctg tcc cca gaa gat cac agc ttc ctg gag gac ttg gcc acc      2311
Asn Asn Leu Ser Pro Glu Asp His Ser Phe Leu Glu Asp Leu Ala Thr
745                 750                 755 tat gaa acc gcc ttt gag aca ggt gtc tca aca ttc ccc tat gaa ggg      2359
Tyr Glu Thr Ala Phe Glu Thr Gly Val Ser Thr Phe Pro Tyr Glu Gly
760                 765                 770                 775 ttt gct gat gag ttg cat caa ctc cag agc caa gtt caa gac agc ttc      2407
Phe Ala Asp Glu Leu His Gln Leu Gln Ser Gln Val Gln Asp Ser Phe
                780                 785                 790 cat gaa gat gga agt gga ggg gaa cca acg ttt tga ataagtctgt gactta    2459
His Glu Asp Gly Ser Gly Gly Glu Pro Thr Phe
        795                 800
```

<210> SEQ ID NO 7
<211> LENGTH: 35

```
<212> TYPE: DNA
<213> ORGANISM: Artificial Sequence
<220> FEATURE:
<223> OTHER INFORMATION: Designed oligonucleotide primer for PCR

<400> SEQUENCE: 7
aagcacggag gaggaagccg ccggtgcgtc gggac                              35

<210> SEQ ID NO 8
<211> LENGTH: 35
<212> TYPE: DNA
<213> ORGANISM: Artificial Sequence
<220> FEATURE:
<223> OTHER INFORMATION: Designed oligonucleotide primer for PCR

<400> SEQUENCE: 8
acgggagcgc aggtgctcgg gcacccgagc tggag                              35

<210> SEQ ID NO 9
<211> LENGTH: 35
<212> TYPE: DNA
<213> ORGANISM: Artificial Sequence
<220> FEATURE:
<223> OTHER INFORMATION: Designed oligonucleotide primer for PCR

<400> SEQUENCE: 9
ggagagcggc tccacgtctt gatgacaata tgcca                              35

<210> SEQ ID NO 10
<211> LENGTH: 35
<212> TYPE: DNA
<213> ORGANISM: Artificial Sequence
<220> FEATURE:
<223> OTHER INFORMATION: Designed oligonucleotide primer for PCR

<400> SEQUENCE: 10
ccacgtcttg atgacaatat gccatacttg acgac                              35

<210> SEQ ID NO 11
<211> LENGTH: 35
<212> TYPE: DNA
<213> ORGANISM: Artificial Sequence
<220> FEATURE:
<223> OTHER INFORMATION: Designed oligonucleotide primer for PCR

<400> SEQUENCE: 11
gcctggcagg agctatataa ggcggcgtga ggcag                              35

<210> SEQ ID NO 12
<211> LENGTH: 35
<212> TYPE: DNA
<213> ORGANISM: Artificial Sequence
<220> FEATURE:
<223> OTHER INFORMATION: Designed oligonucleotide primer for PCR

<400> SEQUENCE: 12
ccaggagagc agagagcgag cctgagcgag agacg                              35

<210> SEQ ID NO 13
<211> LENGTH: 35
<212> TYPE: DNA
<213> ORGANISM: Artificial Sequence
<220> FEATURE:
<223> OTHER INFORMATION: Designed oligonucleotide primer for PCR

<400> SEQUENCE: 13
```

-continued gtagaaagtc ccgaatctcc cgagtcccga atctc     35

<210> SEQ ID NO 14
<211> LENGTH: 35
<212> TYPE: DNA
<213> ORGANISM: Artificial Sequence
<220> FEATURE:
<223> OTHER INFORMATION: Designed oligonucleotide primer for PCR

<400> SEQUENCE: 14
gaatctcccg agtcccgaat ctccccagct cgcca     35

<210> SEQ ID NO 15
<211> LENGTH: 35
<212> TYPE: DNA
<213> ORGANISM: Artificial Sequence
<220> FEATURE:
<223> OTHER INFORMATION: Designed oligonucleotide primer for PCR

<400> SEQUENCE: 15
atggagatac agcaacaggt tccctggcca agagc     35

<210> SEQ ID NO 16
<211> LENGTH: 35
<212> TYPE: DNA
<213> ORGANISM: Artificial Sequence
<220> FEATURE:
<223> OTHER INFORMATION: Designed oligonucleotide primer for PCR

<400> SEQUENCE: 16
aagagctgcg ggcacgggtt caacaggtgt ttgca     35

<210> SEQ ID NO 17
<211> LENGTH: 35
<212> TYPE: DNA
<213> ORGANISM: Artificial Sequence
<220> FEATURE:
<223> OTHER INFORMATION: Designed oligonucleotide primer for PCR

<400> SEQUENCE: 17
tcgtagatgc tgtcaccctg ggcaaccagg tccac     35

<210> SEQ ID NO 18
<211> LENGTH: 34
<212> TYPE: DNA
<213> ORGANISM: Artificial Sequence
<220> FEATURE:
<223> OTHER INFORMATION: Designed oligonucleotide primer for PCR

<400> SEQUENCE: 18
cctggaggga ggaaaagaag agatgaccat tagg     34

<210> SEQ ID NO 19
<211> LENGTH: 35
<212> TYPE: DNA
<213> ORGANISM: Artificial Sequence
<220> FEATURE:
<223> OTHER INFORMATION: Designed oligonucleotide primer for PCR

<400> SEQUENCE: 19
atctgggcca ctccatggtg agtgctaagg gtcct     35

<210> SEQ ID NO 20
<211> LENGTH: 35
<212> TYPE: DNA
<213> ORGANISM: Artificial Sequence

```
<220> FEATURE:
<223> OTHER INFORMATION: Designed oligonucleotide primer for PCR

<400> SEQUENCE: 20
ttcagctgag gctgggcatg gagtgggtgc cgtga                              35

<210> SEQ ID NO 21
<211> LENGTH: 35
<212> TYPE: DNA
<213> ORGANISM: Artificial Sequence
<220> FEATURE:
<223> OTHER INFORMATION: Designed oligonucleotide primer for PCR

<400> SEQUENCE: 21
cgcctgaggg acttggaggt gttgaagcgg cagcg                              35

<210> SEQ ID NO 22
<211> LENGTH: 35
<212> TYPE: DNA
<213> ORGANISM: Artificial Sequence
<220> FEATURE:
<223> OTHER INFORMATION: Designed oligonucleotide primer for PCR

<400> SEQUENCE: 22
cctgcactct ggcgcctgag ggacttggag gtgtt                              35

<210> SEQ ID NO 23
<211> LENGTH: 35
<212> TYPE: DNA
<213> ORGANISM: Artificial Sequence
<220> FEATURE:
<223> OTHER INFORMATION: Designed oligonucleotide primer for PCR

<400> SEQUENCE: 23
ccttctccct tcctcggtcc aatttcccac ctgct                              35

<210> SEQ ID NO 24
<211> LENGTH: 35
<212> TYPE: DNA
<213> ORGANISM: Artificial Sequence
<220> FEATURE:
<223> OTHER INFORMATION: Designed oligonucleotide primer for PCR

<400> SEQUENCE: 24
tcggtccaat ttcccacctg ctgcccttct cccca                              35

<210> SEQ ID NO 25
<211> LENGTH: 35
<212> TYPE: DNA
<213> ORGANISM: Artificial Sequence
<220> FEATURE:
<223> OTHER INFORMATION: Designed oligonucleotide primer for PCR

<400> SEQUENCE: 25
tgggaaggtg gaaagggtga ggtcagcttt ctgtt                              35

<210> SEQ ID NO 26
<211> LENGTH: 35
<212> TYPE: DNA
<213> ORGANISM: Artificial Sequence
<220> FEATURE:
<223> OTHER INFORMATION: Designed oligonucleotide primer for PCR

<400> SEQUENCE: 26
ttccttgctt gatacccatg catctcactc cctcc                              35
```

```
<210> SEQ ID NO 27
<211> LENGTH: 35
<212> TYPE: DNA
<213> ORGANISM: Artificial Sequence
<220> FEATURE:
<223> OTHER INFORMATION: Designed oligonucleotide primer for PCR

<400> SEQUENCE: 27
gagaaaggca ggccagagat gaagggaccc tagat                          35

<210> SEQ ID NO 28
<211> LENGTH: 34
<212> TYPE: DNA
<213> ORGANISM: Artificial Sequence
<220> FEATURE:
<223> OTHER INFORMATION: Designed oligonucleotide primer for PCR

<400> SEQUENCE: 28
accctagatt ctggagtcag gggcagggag gatg                           34

<210> SEQ ID NO 29
<211> LENGTH: 34
<212> TYPE: DNA
<213> ORGANISM: Artificial Sequence
<220> FEATURE:
<223> OTHER INFORMATION: Designed oligonucleotide primer for PCR

<400> SEQUENCE: 29
cagctctcta ccttgacctc accactcaga gtcc                           34

<210> SEQ ID NO 30
<211> LENGTH: 35
<212> TYPE: DNA
<213> ORGANISM: Artificial Sequence
<220> FEATURE:
<223> OTHER INFORMATION: Designed oligonucleotide primer for PCR

<400> SEQUENCE: 30
cgaaactgtt ggcctctgtt atctccccag catca                          35

<210> SEQ ID NO 31
<211> LENGTH: 35
<212> TYPE: DNA
<213> ORGANISM: Artificial Sequence
<220> FEATURE:
<223> OTHER INFORMATION: Designed oligonucleotide primer for PCR

<400> SEQUENCE: 31
agtggttcag gtgagggtag tcagaagaga ggatg                          35

<210> SEQ ID NO 32
<211> LENGTH: 35
<212> TYPE: DNA
<213> ORGANISM: Artificial Sequence
<220> FEATURE:
<223> OTHER INFORMATION: Designed oligonucleotide primer for PCR

<400> SEQUENCE: 32
gagggtagtc agaagagagg atgtcacggc tatct                          35

<210> SEQ ID NO 33
<211> LENGTH: 35
<212> TYPE: DNA
<213> ORGANISM: Artificial Sequence
<220> FEATURE:
<223> OTHER INFORMATION: Designed oligonucleotide primer for PCR
```

<400> SEQUENCE: 33
agaagaggca gctggtaagg gtccgacgtc catat     35

<210> SEQ ID NO 34
<211> LENGTH: 35
<212> TYPE: DNA
<213> ORGANISM: Artificial Sequence
<220> FEATURE:
<223> OTHER INFORMATION: Designed oligonucleotide primer for PCR

<400> SEQUENCE: 34
tccgacgtcc atatccagag cagttccctg atttg     35

<210> SEQ ID NO 35
<211> LENGTH: 35
<212> TYPE: DNA
<213> ORGANISM: Artificial Sequence
<220> FEATURE:
<223> OTHER INFORMATION: Designed oligonucleotide primer for PCR

<400> SEQUENCE: 35
aaatcaggga actgctctgg atatggacgt cggac     35

<210> SEQ ID NO 36
<211> LENGTH: 35
<212> TYPE: DNA
<213> ORGANISM: Artificial Sequence
<220> FEATURE:
<223> OTHER INFORMATION: Designed oligonucleotide primer for PCR

<400> SEQUENCE: 36
ctgccaataa ctacccaatc aggtaagcca caagc     35

<210> SEQ ID NO 37
<211> LENGTH: 35
<212> TYPE: DNA
<213> ORGANISM: Artificial Sequence
<220> FEATURE:
<223> OTHER INFORMATION: Designed oligonucleotide primer for PCR

<400> SEQUENCE: 37
gcctaaatct acccagcatt tcattggcag gacag     35

<210> SEQ ID NO 38
<211> LENGTH: 35
<212> TYPE: DNA
<213> ORGANISM: Artificial Sequence
<220> FEATURE:
<223> OTHER INFORMATION: Designed oligonucleotide primer for PCR

<400> SEQUENCE: 38
ctacccagca tttcattggc aggacaggga cttga     35

<210> SEQ ID NO 39
<211> LENGTH: 35
<212> TYPE: DNA
<213> ORGANISM: Artificial Sequence
<220> FEATURE:
<223> OTHER INFORMATION: Designed oligonucleotide primer for PCR

<400> SEQUENCE: 39
acagccacag tttcactccg tccatccaaa ttgcc     35

<210> SEQ ID NO 40

```
<211> LENGTH: 35
<212> TYPE: DNA
<213> ORGANISM: Artificial Sequence
<220> FEATURE:
<223> OTHER INFORMATION: Designed oligonucleotide primer for PCR

<400> SEQUENCE: 40
ttgcccccta atctactgag cctctggcca tcatt                               35

<210> SEQ ID NO 41
<211> LENGTH: 35
<212> TYPE: DNA
<213> ORGANISM: Artificial Sequence
<220> FEATURE:
<223> OTHER INFORMATION: Designed oligonucleotide primer for PCR

<400> SEQUENCE: 41
cagattgaaa tggaaactgg gatcgctcga agtct                               35

<210> SEQ ID NO 42
<211> LENGTH: 35
<212> TYPE: DNA
<213> ORGANISM: Artificial Sequence
<220> FEATURE:
<223> OTHER INFORMATION: Designed oligonucleotide primer for PCR

<400> SEQUENCE: 42
aaatggaaac tgggatcgct cgaagtctct tgatt                               35

<210> SEQ ID NO 43
<211> LENGTH: 1386
<212> TYPE: DNA
<213> ORGANISM: Homo sapiens

<400> SEQUENCE: 43
ggacagaaaa agaaacgaag gtggaaagtg gagagctgaa ggtggagagg cagagccagg      60
agccttagag gcgcaaatgt ggagagggt ggagggaacc tggcaaaaat acagggtccc     120
tggtaggtgc agggggtcatg gagggtccgg cgctgcccct tcgcttctca gctgctcccc    180
catcttgccc gcctaggcag ggcggggagc ctccggagcg gtgcggaggc agccaggccc    240
cgcccgccgc agccgcgcag ccgccggagg attcctgtcc taatatggag ctgggattcc    300
cccggccccg ccccgccccc cggcccgcgg ggagacagag gctggcagca gggcgggggg    360
aagcgctcgc ttgggggccg gcaacggggg gaagggatgc ctaagtgcag acccaggtcc    420
tcgccgtgcc cccacgtccc tgcctcagtt tccccttcag taaggttaat tagctgagag    480
ggaaaccacg aatcactgca gactacagcg ctgatgttgg tttctattct tggctgtggg    540
aaaacaggat caacgccaaa ttcagctggt ccctttccca ccggactccc tttccaccca    600
tcctcgggac ttagaccccc atgaacaccc cctgataagc cgccaaggcc cgatttggga    660 agcggggcg ggaatttgtt ctctaaaaat ggccaaggga atcccaggtt aaatagtccc     720
cagagaggaa ccccagcagt gacctgtccc acggaggcca aggaaagtcc tccttccctg    780
catgtgaacg tgaccttgtc tgtcaagtaa cgagggggat tgtagacaa ccctgttctt     840 ccccattccc tcaactcctc agaaaaatta gtgtcagtgc cggcccctct ctgccctctg    900
cggactcctg ccgcgggctt caggccgccc taaacctggc cctgtcgctt ccctcaactg    960
aacgcattca gacgccaggg tccccacact ccattcaagc tttcctaacg cagcgccttc   1020
ctctccgctc agctcccgcc aggcttggcc cctccgcag cctcctgctc ccccctcgcc    1080
cgcctccctc cctctctcat tctacgtcat gagatgacgt cggaagccgg gcgggaggag   1140
```

```
gagcccccct ccccagtcag cggtcacgct gcagcttgct tagcccagcc tcccgctctc    1200
gcgccccccc ggctctaaaa cgagcccccc acgcctggca ggagctatat aaggcggcgt    1260
gaggcaggcg aggggggcag cgcagccgag cggagcccag gagagcagag agcgagcctg    1320
agcgagagac ggggaagcac ggaggaggaa cgcgccggtg cgtcgcgacg ggagcgcagg    1380
tgtcga                                                              1386

<210> SEQ ID NO 44
<211> LENGTH: 764
<212> TYPE: DNA
<213> ORGANISM: Homo sapiens
<220> FEATURE:
<221> NAME/KEY: misc_feature
<222> LOCATION: (427)..(427)
<223> OTHER INFORMATION: n is a, c, g, or t

<400> SEQUENCE: 44
gtgagcatgc tggggctacc gcagatccga gctgccaggc gccggagacc ctggagctga     60
gggaacccgc tggggctgtc gcatgtctag ggcagcgtgc tggcgagctg gggagattcg    120
ggactcggga gattcgggac tttctacttt tcctcctgag ctccctccag acctcacctt    180
agttctgaat gagagttaga gagcctggac ggtgtcccta acaccagatt atgagaggat    240
aagagccagg acagagcggc ctcggtgccc gccagtgcag aagcgctccg ggagccgggg    300
agggaagccc gggaagttgc aggatggag ctgcctgagc ctaggggaac atagctactg    360
tccgcggtgc tgaaagggat ctcctgtcgc cttcggggcg ctgcccatgg tgctgacggc    420
tgcgggnccg tgtatggctc tgtccatggt tctgaaccca cagtcggctt cggagctctg    480
tccgcggttc tgaaattcag agccgctttg gagctctgtc cgcggttctg aaattaagag    540
ccgagaggag ccgaccccgc tttagaagtc gagggcttgt gggctatgga gatacagcaa    600
caggttccct ggccaagagc tgcgggcacg ggttcaacag gtgtttgcag aggcaggtcc    660
atgagaaatt cctctggatt ctctgaaact cagaccatgc cttcctcact tcttctctgc    720
ctcccagtct tactcctgac gcactacgtc ttctcgccct acag                    764

<210> SEQ ID NO 45
<211> LENGTH: 179
<212> TYPE: DNA
<213> ORGANISM: Homo sapiens

<400> SEQUENCE: 45
gtgagtgcta aggtcctttt cagctgaggc tgggcatgga gtgggtgccg tgagccttcc     60
actcctgagg aactgggaat tactatggag ggagaggtta taccctacaa gatactgtag    120
atcaaagatt ggctcctgct gttctcccta atggtcatct cttcttttcc tccctccag     179

<210> SEQ ID NO 46
<211> LENGTH: 120
<212> TYPE: DNA
<213> ORGANISM: Homo sapiens

<400> SEQUENCE: 46
gtaaggactc ccttctccct tcctcggtcc aatttcccac ctgctgccct tctccccacc     60
atccactgtc tctctctcag ccactcaccc tcttatctgt ttttctcttc atctatctag    120

<210> SEQ ID NO 47
<211> LENGTH: 181
<212> TYPE: DNA
```

<213> ORGANISM: Homo sapiens

<400> SEQUENCE: 47

| gtaagcctgg agtgttcaga ttccaagaga aaggcaggcc agagatgaag ggaccctaga | 60 |
| ttctggagtc aggggcaggg aggatggggt ttagggggc agaggatctg ggagggagtg | 120 |
| agatgcatgg gtatcaagca aggaaaacag aaagctgacc tcacccttc caccttccca | 180 |
| g | 181 |

<210> SEQ ID NO 48
<211> LENGTH: 345
<212> TYPE: DNA
<213> ORGANISM: Homo sapiens

<400> SEQUENCE: 48

| gtgagtgtcc agagaggctg gggacaagat agcaagctgg aaagggcat gggagaccag | 60 |
| acaaagaatg atctgtagtc aagagtgatg ctggggagat aacagaggcc aacagtttcg | 120 |
| gatgctatag ggtgaacatg aaggtgagga ttcaaggcaa taatcaaatc agaactgggg | 180 |
| gactctgagt ggtgaggtca aggtagagag ctgagtggtt caggtgaggg tagtcagaag | 240 |
| agaggatgtc acggctatct caattcagtg agaggtgac caagggtggg gagtaggtag | 300 |
| aattgcctgg tggacatcct aactctgcat cttctttctc cccag | 345 |

<210> SEQ ID NO 49
<211> LENGTH: 121
<212> TYPE: DNA
<213> ORGANISM: Homo sapiens

<400> SEQUENCE: 49

| gtaagccaca agccagggga ctaggggca gctgaggtcg tcatggagga gacacaaatc | 60 |
| agggaactgc tctggatatg gacgtcggac ccttaccagc tgcctcttct ctcctctcca | 120 |
| g | 121 |

<210> SEQ ID NO 50
<211> LENGTH: 690
<212> TYPE: DNA
<213> ORGANISM: Homo sapiens

<400> SEQUENCE: 50

| gtgagtcagc caaaaggtcc aagaactcaa gtccctgtcc tgccaatgaa atgctgggta | 60 |
| gatttaggca aatcaattcc ccctctctgt acattgattt tattaagggg atgacatccc | 120 |
| ctgctgaaga gagtagcagt ggagataaga aaaatgaaa gacttaatat gaaagtttga | 180 |
| acaagcagac ttggcagggg ttgggctgt gggatagagt gctagggaat tcttaagtaa | 240 |
| gggcttgtgc ttaactccat gagaggccta gatcagtctt cagcacccca ttttacagat | 300 |
| gaaaataatc aaggtcccag agttaaacag actttcctta gggtgcacaa caaactgatg | 360 |
| gaagagggac tagagctcta tcctagtatc ctagctccct gaaggggata cagagcaaga | 420 |
| atttatgcaa gttggtaaaa gaaagacgag gctcagcccc tgactccatt gaggtagctc | 480 |
| cctggttaca gccccatcct tcctaaacta cagccacagt ttcactccgt ccatccaaat | 540 |
| tgccccctaa tctactgagc ctctggccat catttcatca ttgagccaat atctttgaag | 600 |
| cctatactaa taccaacaca ttcagcccc caggatcctc tgtgctaatt ggtctaactg | 660 |
| attgtgttct ctctatctat ctctctgcag | 690 |

<210> SEQ ID NO 51
<211> LENGTH: 2465
<212> TYPE: DNA
<213> ORGANISM: Homo sapiens

<400> SEQUENCE: 51

| | | | | | | |
|---|---|---|---|---|---|---|
| ataagtctgt | gacttaacgt | cgtcaagtat | ggcatattgt | catcaagacg | tggagccgct | 60 |
| ctccaccccc | ccgggactgt | tgggggatt | ctgagggcca | gagggggata | tatatgattc | 120 |
| cccaggccct | gcaggatttt | ggggggggg | aggtgggagg | gcaagggagg | ggagcttctt | 180 |
| tttaaaatca | agagacttcg | agcgatccca | gtttccattt | caatctgtat | tcactcgtag | 240 |
| tgagtttcct | tgaatgggat | ttcaagcgga | gaatggggga | gtctcacttc | cccgccgcct | 300 |
| tgccccattg | gcctgggcca | gttctccact | cctaggggcc | aagccacccc | tagccttggt | 360 |
| gggggaaagg | cagggcccac | ccgggccagc | ccgtgccctg | aggggctctt | gacacccacg | 420 |
| tagaattctc | tacacaccag | taacgggatt | tcaattccga | tggactctgc | cgcctggcgg | 480 |
| cccttcctgt | gacttttgcg | ccccgcgcct | ggggtggggg | gtgcgaagag | acgctacgtt | 540 |
| cctttccgat | ggaggaaggc | agacctgccg | tcacacgtgt | gcttgcacga | gtgcgtgtac | 600 |
| ctggtgcggg | actcacccgg | ccgccagact | gcctgggcct | gcccagatgg | ccacctcgtg | 660 |
| gtgctgcggt | gactttgtag | ccaactttat | aataaagtcc | agtttgcctt | tttggtacct | 720 |
| ctggtgtcat | gcgctgctgt | gtaaaaggaa | gggtggagga | taagtttggg | aggcttggat | 780 |
| gggagcctgg | gggccaggag | gtaaaagctg | gacctgttta | tggccccagc | atttcttcat | 840 |
| ccacttgtga | attcattcat | tcattcactc | attcattcat | tctttcactc | aacgtccaca | 900 |
| tgtacattgt | gtggcccata | ctgtgctaga | agctggaaag | tttagggctg | aaacagatgt | 960 |
| tatgtcttgc | cctcaaggtg | cttggcgtcc | agtactagaa | aatactggca | tctcctctct | 1020 |
| gcgccaggct | tgcagtgctc | gtggtgtggg | aggggacaga | gggcctagga | gtggacatga | 1080 |
| ggattcaatt | tgatgttggg | tctgggcatg | ggtttgaagc | ttctgctcac | aagttctttc | 1140 |
| ttcacctggt | ccttcaggga | agcaacttcc | ttgtgggcc | ctggatcgac | tcactggaaa | 1200 |
| ttataaccac | gtctgttatc | cttgcacagg | gctttcagct | gacacacact | tttacctctc | 1260 |
| ttatttgctg | caacaattct | tctgggcagg | catattagcc | catctcactg | atgaagaaac | 1320 |
| tgaggaccac | aggtaaaaag | ttatttgttc | ccacaattga | tgacaggcat | gggtggatgg | 1380 |
| gcaacatacc | cagagcatct | gcatcccagc | cctgggctgt | tttctctgct | ggcagagcca | 1440 |
| gtgaatcacc | acccatccca | aatcatctca | tcccagatta | ctcaagaagg | gcaaatgtgg | 1500 |
| gctggagcag | ggtcctctct | cccaagtgtg | gggtgagaaa | ccccttcttt | ttgctctcca | 1560 |
| ggtctgtaaa | gtagagctga | gcagaatata | actcagtaag | tcaagagaaa | aaagtttcca | 1620 |
| aaaatgctgt | tttcctccaa | gcttgaagcc | caaacagcca | caaggtaggg | tgaggggcaa | 1680 |
| atgaaaatga | ggagatgggc | tgggcacagt | gggtcatgcc | tgtaatccca | gcaccttggg | 1740 |
| aggacaaggc | aggaggattg | cttgagccca | ggagtttgag | atcagcctgg | gaaacatggt | 1800 |
| gaaatcccat | ctttacaaaa | aatacaaaaa | ttatctgggt | gtggtgcaca | cttgtagtcc | 1860 |
| cagctacatg | agagcctgag | gctggagaat | ctcttgagcc | tgggaggtgg | aggttgcagt | 1920 |
| gagccaagac | tgcaccactg | tactccagcc | taggcgacag | agcgaaccct | ggattcaaat | 1980 |
| ctcatctcca | ccaattattt | gccaaatggg | acttgaggct | cagtttctcc | acaagtgaag | 2040 |
| cagggctgac | aaacatggta | cttatctccc | aaagatgctg | ttagaacttg | atagtgtcca | 2100 |
| tttataagca | gagaagcaca | gaattgactt | aagttattca | attgaattag | aaggcaacgg | 2160 |

```
tgacctcaaa ggcttcccca gtgaagtaca gaggctgggt tccaggaact gagggcacaa      2220
cctgagaaag cccctaagcc tccttttatt ccaaatcctc cagctctggg gccatgccct      2280
tcagacagtc ccatgggaag gaagacactc ctagggacct gtcactattt ttccaacttg      2340
gatgggtcct tgggtggaaa aggagggtgg agttttgccc tctgccttcc ttgtgcatct      2400
gttctccaac ttggacaaaa taactggatt gtcagcccca ggaggaccct ggcatggagc      2460
acagg                                                                  2465

<210> SEQ ID NO 52
<211> LENGTH: 35
<212> TYPE: DNA
<213> ORGANISM: Artificial Sequence
<220> FEATURE:
<223> OTHER INFORMATION: Designed oligonucleotide primer for PCR

<400> SEQUENCE: 52
ggtcatgtac cgctccacca aggcgctcca aggcg                                 35

<210> SEQ ID NO 53
<211> LENGTH: 35
<212> TYPE: DNA
<213> ORGANISM: Artificial Sequence
<220> FEATURE:
<223> OTHER INFORMATION: Designed oligonucleotide primer for PCR

<400> SEQUENCE: 53
cccaatatca cgggcacagc agactgccag catct                                 35

<210> SEQ ID NO 54
<211> LENGTH: 7408
<212> TYPE: DNA
<213> ORGANISM: Mus musculus
<220> FEATURE:
<221> NAME/KEY: Intron
<222> LOCATION: (1594)..(2347)
<220> FEATURE:
<221> NAME/KEY: Intron
<222> LOCATION: (2500)..(2673)
<220> FEATURE:
<221> NAME/KEY: Intron
<222> LOCATION: (2777)..(2886)
<220> FEATURE:
<221> NAME/KEY: Intron
<222> LOCATION: (3161)..(3347)
<220> FEATURE:
<221> NAME/KEY: Intron
<222> LOCATION: (3458)..(3784)
<220> FEATURE:
<221> NAME/KEY: Intron
<222> LOCATION: (3921)..(4050)
<220> FEATURE:
<221> NAME/KEY: Intron
<222> LOCATION: (5481)..(6138)

<400> SEQUENCE: 54
aaggaaaaaa aaaaaagaa aggtgtatgt tgtgcgctca ctcagtgaca agtgcacagg        60
cagaacgagg agccctggag ctaaagatgg agcaagaatt gaagggagat ggggagggga      120
ctctggcaga attaaagggt cttgggtagg tgcagcagcc actgagggca cagcagaccc      180
tggctacttg gcagcctccc cctcttcccg gctgaagcag tggggagagc tttctagagc      240
tgtgcggagg ccggtaggcc ccgcccgccg ctgccgccgc cgcagccgcc ggaggattcc      300
tgtcctaata tggagctggg attccccccg ccccgccccc gccccccagc ccgccggaga      360
gactggggct cgcaagaggg cggggggaaca gctcgtcttg ggggctgaca agcgggaggg      420
```

```
gatcgtggga gaggttcaaa cacacatcca gatcctcacc aggccctggg tctttgcctc      480
agtttccccg acaggtggct aagatgaact aatagaggaa aaaggaatcc ctgcagatca      540
cagtggagat gtttgtgttc ctatggtgct aaggaaatat gatcaagacc gaattcaagt      600
ggtctcttct ccacaggacc accattccac cctatcctgg agatttagac cctcaggtca      660
gggcatggag gcgaagaagg aattatttat ttgaaactgg ctaagggact ttcagattga      720
atagacccca gaaaagaccc ccagttgtga cctagcccct ccccaaaagc caaggaaagt      780
ccctcatgta atttcgaccc ctgcctggca gatggcggca aattggcaga ggaccaagcc      840
ccttctcatc ctttgcctcc ttagaaaaat ctatgttgat agcagcctcg ctttgccttc      900
tacaaactct cttgttaagg gcttcagacc accctaatcc atgtactgtt cctcctccta      960
atagaatgta atggaaaacc tgggtccctg caccccattc ctggctctgc acagctcttg     1020
ccagccggcc ccctctgcac cctcccttct cccccttccc ccgcccccctc cctctcccgt     1080 tcgacgtcac gggatgacgt cggaagtctg ggagggagga ggagcacccc ccctccccag     1140
ccagtggctc cctctgcagc ttgctttagc ccagcctccc gcctcccgct gccccccccg     1200
tctctaaaaa cgagccccccc acgcctgtca ggagctatat aaggcggatc gaggcaggcg     1260
aggggggcag cgctgccgag cggagcccag gagtggagcg agagcgagca agagcctgag     1320
cgaaaagacc gggaagcaag gaagaggaag cctccggtgc atcgggaaag gatcgcaggt     1380
gctcgggagc cggagctgga gctccacagc cggcagtcat gtaccgatcc accaagggcg     1440
cctccaaggc gcgccgcgac cagatcaacg ccgagattcg gaacctcaag gagctgctgc     1500
cgttggctga agcggacaag gtccggctgt cctacctgca catcatgagt cttgcctgca     1560
tctacactcg caagggtgtc ttctttgctg gaggtgagca gcttgggcta ccggagacca     1620
gagctgacgg ggaccaggga tggaggagct gagggaatgt gctaaaactg ccgcttgtct     1680
agcacagcgt gctggaagcc tgtggagaga agggacttga ggggaccctg gacttcctac     1740
tttttcttct gagctccatc tagactagcc taaacgatag tcctagcact ggatttgtgt     1800
gagatagagc gctaaaacag aatggtccag gctcccattg cctcagaggc actccaggaa     1860
tccggggagg gtacggaagg aagcctggca agctacaggg aaagcctgca aaggcaaagt     1920
atgaggaaga gtagcttgtg ctagaaaatg ctgagagggt cttctatgc gctctggagc      1980 tgttcgacgt cctgaagcca tcacccttc tggcgctgcc cgcggtgctg aaatggccat      2040 agccccttt cgcaggagct gtccgcggtg ctgaatccca gtcctttcgg gagagctctg      2100
tccacagtgc tgacagcaga gggctgctga ggttccggcc aggcttggaa gtccaggggc      2160
tccctggcta gatagtttta gcaacaggtc tcctggccaa gatccacaag cataggtca       2220 acaggtgttg gcagaaatag gtctatggga atttcctgtg tcttctccaa gactcaaaag     2280
atgttctctt tatttctgtg ttgtccctga ttcttatcct gactcaccac atcttctcac     2340
cctacaggca ctcctttggc tggccccacc gggcttctct ctgctcaaga gcttgaagac     2400
attgtggcag cactacctgg atttctcctt gtattcacag ctgagggaa gttgctatac      2460 ctgtcggaga gtgtgagcga gcatctgggc cactctatgg tgagtactaa aagtccttgc     2520
atctcaagtt ggggtatatg tgagataaaa tgagcctctc actactgaaa acagagttat     2580
tagaggcgag tgtgggggag tcttccctaa gaaaaatcat tggttgcaga taggctcttg     2640
ctgccttcac taatgatcac ttctcctttc taggtggacc tggttgccca gggcgacagt     2700
atctacgata tcattgaccc tgctgaccat ctcactgtgc gccagcagct caccatgccc     2760
tctgctctgg atgctggtaa gaacctcctc tcggttcttc agtttactcc tctgctgccc     2820
```

```
tgccctaact atctactctc ctccaatgcc caccctctta gtcagttttt ccttttgctc    2880
acctagatcg ccttttccgt tgtcgattca acacctccaa gtccctccgg cgccagagtt    2940
caggaaacaa actggtgctt attcgaggtc gattccatgc tcacccacct ggggcctact    3000 ggcaggaaa ccctgtgttc accgctttct gcgccccact ggagccaaga ccccgccctg    3060
gccccggccc tggccctggc cctggtcctg cttctctctt cctggccatg ttccagagcc    3120
ggcatgctaa ggacctagcc ctactggacg tttctgaaag gtaagcccaa agtgttcaaa    3180
ctccagtaag aagggaggcc agaaagaagg aactttagag ttcgtgatct tagattcagg    3240
gcagggagga tgggcttaa gtgggcagag agcatgggag ggagtgaagt gcatgcattt    3300
tgagtaaggt aaacagaaag ctgacctcat catttccacc ttcccagtgt cctaatctac    3360
ctgggctttg agcgcagcga actgctctgt aaatcatggt atggactgct acaccccgag    3420
gacctggccc aagcttcttc tcaacactac cgcctgtgtg agtgtcctga gaggccgtgc    3480
ataacacagg aagctgggag aaagcatggg agacaggcca gggactggct gtggtccaaa    3540
ctgatgttaa ggagtttcgg aggctacaga gtgagcttga ggatgagaag tcaaggcaag    3600
aataggacag agttagaaaa cactgtgtga taaggtcaag tggggagcct agaggtacag    3660
gttagggtag ttagaagaga atatgtcatg gctccctcaa ttcagtgtag aggtaagaaa    3720
ggtgggtgtg taggtggtgt tgattgatgg accttctaat ccggtattcc ttttttctcc    3780
ccagtggctg aaagtggaga tattcaggct gaaatggtgg tgagacttca agccaagcat    3840
ggaggctgga catggattta ctgcatgcta tactcagaag gtccagaagg ccctttttact    3900 gccaataact accctatcag gtaagctgta agatacaaga tggcggagag gggaggggag    3960
ctgaggtcag catagaagaa atgcaacgaa gaaaactact ctggtaatgg acagcagacc    4020
cttacaagct gccacctctt ccctttccag tgacacggaa gcctggagcc tccgccagca    4080
gctaaactct gaagacaccc aggcagccta tgtcctagga accccagctg tgctaccctc    4140
attctctgag aatgtcttct cccaggagca atgctctaat ccactcttta caccatccct    4200
ggggactcct agaagtgcca gcttccccag ggctcctgaa ctaggtgtga tctcaacacc    4260
agaagagctt ccccaaccct ccaaagagct ggacttcagt tacctgccat tccctgctag    4320
gcctgagcct tccctccaag cagacctgag caaggatttg gtgtgtactc cccttacac    4380 accccaccag ccaggaggct gtgccttcct cttcagcctc catgaaccct tccagactca    4440 cttgcccect ccgtccagct ctctccaaga acagctgaca ccaagtacag tgactttctc    4500
tgaacagttg acacccagca gtgctacctt cccagaccca ctaaccagtt cactacaagg    4560
acagttgaca gaaagctcag ccagaagctt tgaagaccag ttgactccat gcacctcttc    4620
cttccctgac cagctacttc ccagcactgc cacattccca gagcctctgg gcagccccgc    4680
ccatgagcag ctgactcctc ccagcacagc attccaggct catctgaaca gcccccagcca    4740 aaccttccca gagcaactga gccccaatcc taccaagact tacttcgccc aggagggatg    4800
cagttttctc tatgagaagt tgcccccaag tcctagcagc cctggtaatg gggactgtac    4860
actcctggcc ctagctcagc tccggggccc cctctctgtg gatgtccccc tggtgcccga    4920
aggcctgctc acacctgagg cctctccagt caagcaaagt ttcttccact acacagagaa    4980
agagcaaaat gagatagatc gtctcattca gcagatcagc cagttggctc agggcgtgga    5040
caggcccttc tcagctgagg ctggcactgg ggggctggag ccacttggag ggctggagcc    5100
cctgaaccct aacctgtccc tgtcaggggc tggaccccct gtgcttagcc tggatcttaa    5160
```

```
acctggaaa tgccaggagc tggacttcct ggttgaccct gataatttat tcctggaaga    5220
gacgccagtg gaagacatct tcatggatct ttctactcca gaccccaatg gggaatgggg   5280
ttcaggggat cctgaggcag aggtcccagg agggaccctg tcaccttgca acaacctgtc   5340
cccagaagat cacagcttcc tggaggactt ggccaccat gaaaccgcct ttgagacagg    5400
tgtctcaaca ttcccctacg aagggtttgc tgatgagttg catcaactcc agagccaagt   5460
tcaagacagc ttccatgaag gtaagtctag cctgaatgtc caagagccct gcccttctaa   5520
tcagacattg catagattgg gtgaatcagt ccccaactct gaaactctgt tttattaaga   5580
gaacaatatt acctcctact aagaagagta gtgaggtagg aataatacaa agctttgtgt   5640
gaaagatgag tagacctggt gggcggggga ggtgagctag aaaaacgcga tagacaatcc   5700
ctaggcaaaa gcttgaaagc ttctgagaga cctagaccag acaacaccgt catttatag    5760
acaaaaataa tcaaggcccc agagttaaag aaactttaag tggcacaaaa attgatagaa   5820
gttgatgctt ccccctgaag gggacccaga gcaacaactg gttaaaatta ggagacagaa   5880
agaacaatgc caagccccta gctccaatct ggcggccttg tgctgtttgt ccaaagctgt   5940
ggccacagtt tccctccata tttgcatatt gcctcttatc tgctgacacc ctggggatca   6000
gttcatttgg ctaacacatt tgacgtccat agactatagc aatattgtac cactgcctga   6060
gcccaatgac gcttttactg aataagcttg actaacatac gcactttctc tcttctctct   6120
ctctctcttt ccccacagat ggaagtggag gggaaccaac gttttgaata agtctgtgac   6180
ttaacgtctt caagtatggc atattgtcat caagacgtgg agccgctctc cacccccccg   6240
ggactgttgg ggggattctg ggggccagag ggggatatat ctgattctcc aggccctgaa   6300
ggatttaggg gggaggtggg agggtaaggg aggggagcaa cttttttaaaa tcaagagact   6360
tcgagcgatc ccagtttcca tttcaatctg tattcactcg tagtgagttt ccttgaatgg   6420
atttcaagcg gagaatgggg gagtctcact tcctcaccgc gctgccccat gggcctgggc   6480
cagttctcca ctcctagggg caaagccacc cctgggcttt ggtgggggaa aggcatggcc   6540
cacctggggc tagcctgtgc cccgaggggc tcttgacacc cacgtagaat tctctacaaa   6600
ccagtaacgg gatttcaatt ccgacggact ctgccgccct ggcggctctt cctgtgactt   6660
ttgcgccccg cgcctggggt ggggggcgcg aagagacgct acattccttt ccgatggagg   6720
aaggcagatc tgccgtcaca cgtgtgcttg cacgagtgcg tgtacctggt gcgggactca   6780
cccgccgccc agaccgccta ggcttgccca ggtggccacc tcgtggtgct gcggtgactt   6840
tgtagccaac tttataataa agtccagttt gccttttttgg tatctctggt gtcatgcgct   6900
attgtgaaaa gggaagggag gggaaggag agattgagga gcccagatag gaggctgggg    6960
caggagtcac aggttagacc tcctctcagc cctggtatct ctaagtgagt ttgttcatat   7020
ctccatttga ctctgcttgg tccacactgt gctagaagac taagtacttg tcagaagcag   7080
acattgcacc aaagacactg gagtcttctc tctgccctgg gttatggtg tgatggggag    7140
gaaagagcct ggggctgagc aagtttgtca ctggtcttgg atatgggttt aaagtttctg   7200
gtcatttcct gcctggtctt tcaggatatt gatttcctca tggagcctta gattttaaaa   7260
atcagaagct gaaacctgtt acgcttgcgt agggctgttc agttagcaaa tacccaatcc   7320
actgcaataa atttccactt cattgggaaa gcaacccgat aacgggtgtt cctccagtta   7380
caggtgagaa acacatcaac ccctcccc                                     7408
```

<210> SEQ ID NO 55
<211> LENGTH: 20775

-continued

```
<212> TYPE: DNA
<213> ORGANISM: Mus musculus
<220> FEATURE:
<221> NAME/KEY: Intron
<222> LOCATION: (9769)..(10522)
<220> FEATURE:
<221> NAME/KEY: Intron
<222> LOCATION: (10675)..(10848)
<220> FEATURE:
<221> NAME/KEY: Intron
<222> LOCATION: (10952)..(11061)
<220> FEATURE:
<221> NAME/KEY: Intron
<222> LOCATION: (11336)..(11522)
<220> FEATURE:
<221> NAME/KEY: Intron
<222> LOCATION: (11633)..(11959)
<220> FEATURE:
<221> NAME/KEY: Intron
<222> LOCATION: (12096)..(12225)
<220> FEATURE:
<221> NAME/KEY: Intron
<222> LOCATION: (13656)..(14313)

<400> SEQUENCE: 55
tctcctgatt tttaaagccc ctctgtcttt cctggccccg cttggcctcc ctgaagatgc      60
cctgccctct gcatacctag ggccaatagg agtgatgagc ccatgtcatg tctgctctgg     120
gattctaatg acccaatccc tacaccagac acacaaggca tggacatctg ctcacctgta     180
ggctccatgt cactgggtac acgcaggtga tattacagac aagtgtaaag cttcggtctg     240
tggtggcctg caggtttgtg tgtacctagg tagaagagga agtgaggagg caccagtcag     300
aagcaactct gagaaacagg agccagaatt taagctgggt aagaacatga agatggcca     360
aggattgcaa ttgttggccc ctggagaaca cactgggact ggtcttggat gttctgttct     420
gtactggagg gatatgggat gcctgctgac acacaggaag ggtctgaacc cagaccctca     480
gggtcactag gtatgcgtac ctcagttttcc taaggctcat tgacttcttt gttcgtttat     540
tcggagaaca gcacctattc tggccacctc cataaggagg gtttcaggaa gcacccaggg     600
ctatgaaccc atcgagccac ttctgtctga ctgcattcaa acgatagtt tccttaagac      660
aatggccact ccccgtgcat tctccaacac ttactccgtt ccttccgtgc ctatggcttt     720
gttctgagtg ttttgacaaa ttagttcacc tggctcttgt gtcagagctc taacacaaat     780
tgtattctcc tcttcacaac tctatttaat acactggtaa actgaggcat gagaggctgc     840
agtccttacc tcagcagtgt cacagtctgt aacagaggca agacctccct ccaggcccca     900
ccctcttgcc tacctgcct tggctctctt ccggtctcta tgcgaagatc ctatgtattc      960
agacccttct tttaatttt taatggcttt tttattttact ctgtgtgcat gcatgtgagt    1020
gagtgtgtgc cgtggtttat gtgtggcagt cagaggacat ctttcggctc tccttccacc    1080
atggaggtcc tggggattga agttaggctg tcaggcttgg cagcaagtgc ctttacctga    1140
ttaaccttgc tgcccacccc taaccccttc ttgctggctc ttccattcgg aataaggcaa    1200
accatgccct ttcagccttc ttttcaccga gaagaattat cttccttctt ttcatcttct    1260
caattttttcc tacaaatata cctggaatgc ttcgatcaga gctgatggca gacaaaggtg    1320
acagctccta cccagggggtc tccaatacaa gccagagaag acagcagctc attaatgaaa    1380
cgaagtgtaa aactgtcacc atcacaactg gcaacagaag cacagggaac cctgggacct    1440
acagctgggg atttgacccg atagagaaga ttttctggag tgatatttga gccaagctat    1500
tgtgaaaaat gaggatcagg tgcaaggaga ggcaaggggc gtgcatgtgt gcacggagct    1560
gcagaaccac aatggaagag ctgcctgtgg ctagaagaga gggacgggga ggaaggaggc    1620
```

```
agggtcgggg gttgggggga agatcaccag agtgcagcct gggagaaggc ttagggtggc   1680
tcctcacagt tcttgacatc cttgatgatg aagctaagc  ctggccactt cacctcatag   1740
gacagctcct gcagccatac ctgctgcgta aagaagcctc agctcccttc ccccacagca   1800
ccacctcatt cccatctaat taattgtttg cttttacctt ggctactgct actcaccaca   1860
ccttataaag ccatgagacc acgtcttgc  taatctcatc ctccccaccc acccagcaca   1920
gccacgttgg tcagttggcc acttgactcc caagcaacgt ggcgcaaaca cacctcccta   1980
ggaaccccac tgccatatcc ctaggcttgg tcttccccat gttgcagcca ccgagcaccc   2040
cagatgcccc tttccagaca gcatctcatt cagatggctt cctcttaccc tgtggaagct   2100
ccatgatgtt aaagccaagc ttgtgcctct ccccgacccc cgccagtatc caccagagag   2160
gctggcctct ggcctcaatt catcccacag ccctgtgcag tgagcgtgac atccatcccc   2220
acggtccctg tgacagatgc tggcagtatg gcggccagcc tgaggtcccg tgtgggtggg   2280
caaggaatag catttgagaa gcagaggcag gagggtcaca agttcaaggt tatcctctgc   2340
tatatatgag gatgcatgcg attctttctc aaattttaga aaatgtgcat caaggaagag   2400
gcacaggtcg ggtgtgaggg cagaggggc  aagctagtca cctctagaag atcagcaggg   2460
cagagttccc ttgctgagga aagtcagaca tgaacatgtg aggcagatct agagggcagg   2520
ggccacaccc tcggtttcta tcttcatgcc actgaggcac atgggtccc  tggtctgaat   2580
tttatctctg gtccatgaat taattttcct ctcctccttg gagcagatgc ctccagtcag   2640
ccccatcctc aagccttgcc cagataccrt caattttctc atccaggttc cagtctctcc   2700
ctcctgccca caccatccct ccccgccctc acctctgctc agcccactcc cctggctctg   2760
accgtttcta tgcgtaggtg gcagcgtgta ccctcttcac aggagatttg ttgatttcat   2820
aaccataaat agataaaatg ttctgagtgc ttccatgagc gagtagaatt gagggagtga   2880
tcacacaatg aaaaggctgt aggagaagga aaacagcctg tggagacaca gctgaaaccg   2940
gcttggtgct gcacaaacca gcactacctg agggcgagct tgccgttgca taagaggtat   3000
accataaaca caggacttgg gactgccaga gaaccttctg gaaaacactt atgagactgc   3060
aagtctgtca attcaaagga acaatatatt aagaaaatct agatttaaaa tgaaaacaga   3120
acgtggaagc caacaaacat ggatttttaa ttctgagttc atctcatttt ggctgtgtga   3180
ctatgagcaa gtttctcatc ctctctggga aggtgtatat tcatctcttg ggtcagacta   3240
gagggaccaa tcatataata tgctcatttt ttcctctaag aaaaagtggt cttctcgatt   3300
acaacttaac ctccaatatg aacaatttg  tcttcccaaa acgcagtccc aagacactaa   3360
ggatggatag ggtaacctgc tttttcattg tcaagtagaa ctcatgttga catgaaatg    3420
ggttatgcac aatcattctt ggatggggag accatatatt catagttaca agaaagcta    3480
gacattagga aggacttccc aagttcttct ccctaagatg ggtaaagaga gtagagagag   3540
gatgtgacag ctcagtttgt tctgagactg gagagctttc cagagagagg gaaagctatt   3600
tctttacctt ctgctctaag ggtggcagga ttttctgtca agggttaggt agtaggtgtt   3660
tgggcttggt gggagctcta gtcccttctg cacttaactc tgtgactgtg tgaagaaggg   3720
caccagccat aagtatgtga atggtctgaa tgtgtcccag taaaacttca ttaatgaaaa   3780
gaaacagcgg accagatttt attcggtgcc atagtgtata ggcccaatc  tcgttctaca   3840
cggcaagaga acaagtttga atggggagga atgaaccatg cacagggcac tgccagagcc   3900
ctgctgtctg actttaagtc attgctcact tctgatctta acctcatcga ctatagaatg   3960
```

-continued

```
aacgtaataa tctcaatcat cagtcctgag acaatagcta agaggaaggt tagggtggct    4020
aggaaggctg tgtgtcaaag tgaaagaact gacgcctgca agttaacctc tgacctccac    4080
acacagacac catgcacat gtgtgttctc ttcatgtgac aaattaaaaa ttgcaaaata     4140
aaaagtgcct aagagatcag agtaagtctc tctctccctt tactccaccc ctttgagtgg    4200
cactgagtct agcagcacac gaggccacat ccttgtctgc tgcaggtgac ggtggccttc    4260
ttggatggag acaaatattt cattatagtt ggattcttgg tctgtctttc taacatgcgg    4320
tcctcagtga ccccatttct ggagcaagcc cagcacagga ggaaacgagg aatctctctt    4380
cctctccact gtccgggcat ttggcagggt gctagagttc atgtcaggga gcaacatggc    4440
cgcagtggct ggtgccagac cttgggagag gccttcaaga ctcaggctgg gatcagagtc    4500
aggaacagaa agctctgagt tctcccagaa cattcagctc tggtcccagc ttccctgggg    4560
tctccacgaa gcagccacag ctgtggtcca ctgggaacct gcagccccac ccacggcatc    4620
ataaagtgaa agttgtcctg ctcatctgct cagatgatct cggagtgctg catccttcag    4680
cactgattta tctcagaagc cctagcaagg gattccttta ttttctcatt ctgtccctct    4740
tcctcttccc ctccctctcc tttgcttcat ccttccttct cttcctcata ggcatacttg    4800
tgcagacaaa taccacatgt atgccgacag tcccccgtca catccttgct ccagtatttg    4860
agaaaaggag ccaggagtct ccatgatatt cttaagaatc aaaccctcca ttccaattcc    4920
tcaggaggtc ttcctcctgg acaatctctg aaaaagatgc accatttctc taatagggat    4980
tgaggggtga tgaccctcta gagccccaat aaagccatga agagaggagc agaggacttc    5040
atggtctgct cttgctataa aaaggccttt ttcgggaaaa aataaagaa aggaatcagc     5100 caatcccttc acgatgccat cacctcttct tggtggtttt tcggggaagg agtgggtggg    5160
tttccatggc aacagatgcg agctctgctc agtaaagaag ggaccttgat attttttctc    5220
tctcattctc tcagttgtgt gtgtgcctgt gtgtatgtgc gtgctacaca tgcctatgcc    5280
cacaccagca atttttttag aactaaagaa agcccttcta tcagctcccc aaatatggag    5340
tgatagaaaa ccatgcactc ctgcaggcca gagaaggttc tggatggttc cagagaaggg    5400
tgctcctgtg aacttgtttt cctccattgc agagattgtg tgcagcagag aggcctttgc    5460
aaactgttag aggctaagag ttagaaaaaa ggatgtttgg tggagagagg ggaacaaagg    5520
atagatggtg caaaaaccaa cgaatggcgt cctagtgggc aaccaaaggt gcacggagtc    5580
tcaggaagca cagtcagcac aaaccaccta acgctgaaga aaaggctcaa ggcagactca    5640
tatatggaca caaacacaca gagaggtata aaagcaaata tattaggcaa aaccgcaaaa    5700
ctgcatacaa cacagaaagg cagagactta gagaaataaa acagacaaat aaaaacacag    5760
atgcaggtac tggcagatat gtagacacac aaggatgcag agcctatcat caaaacacag    5820
gcaaatagat acatggatgc agatagataa gtgtatccag acagataggt ttggatgcag    5880
acatagaaca tgcaacacag cctcattcaa gtgcacacac tcgtgtgcgc tcacacacac    5940
actccccttt ccccctcag ttgctcaagc ttcctatagc aggaaggcag atctgcaaat     6000
gctgcatgtt cacccagtaa gtttggctgt gaatatcttg taaccccac ctattgcttc     6060 tacacacaca cacacacaca cacacacaca cacacacacc ccaaagcccc                6120
tctcccaact ttgtccactt tcccataacc aaaggctgtg ataccctcccc catctccaggc  6180 ttccaattct gttttgctgc tgctgctgcc gccgcctgcc gcttgggggg ggagagagtg    6240
gggtgactca gccaggccag gatgactcac actgacagta tttttagcag cggccaggag    6300
ctctctagcg tgccagccgc ccccctcctc ctgcttgcta tttcggaacc gtcactggtg    6360
```

-continued

```
atataaatag ctcttctccc acggcctgaa gctgctgcca ggctatttttt ggttctgcac    6420 agttaaaaat agtttcatgg aggtgggagg caagaggagt gggagctggc ctagggagag    6480
gagacattgg gggcatacag agcttctcaa cttgaatcag agtagtcgaa ctaagatgat    6540
cccttcccta cccctcccct tgcccctttc tagaaccttc tccccttcca acgttcctta    6600
tccctagtcc atcctcctgg aaaaatccaa ggattcctcc cttgagccca attttctttc    6660
caagcttaac taattcctag aaccgaggag tcttgacagc cacacctgta aatagcccat    6720
atgtattctc aatgaggagg atgacagcat cgggatgcca ttctcatcta tcccgaggcc    6780
cagctcggct ttgatgtcac aggcaaacca cgaccattct gagtgggaag gcaacattca    6840
gcaccacgga cagcgacaac atccccccccc ccctccccc ttccaggtct gcttaaattg    6900
cttggagacc agctgtggac ccagcagaga gatgcaactt attgtggagg agatatcaag    6960
aacgtctcct ggccagggct taaagcacct gtctgtgagg aagacagggc agagatgaac    7020
cccagagata gaatggttgt ctagcataca cagagccctg gtttcatcct cagctttggg    7080
aaactaatct agaaactcca tcttggattt gcatatggaa agagaatcca aaaccaagg    7140 gaagagaatg gaacagggag tggtggtgtt gagtgggggat atcagagtta ataaggatga    7200
aacatgccag agagaaatac atcctgaaga aaccatttct gtcacccata aggttggaaa    7260
cagtgtctta cagacacaca ccattttctc catctcagct ataccactgg ctggctacat    7320
ggttgtatat gtagatgctt tctatctgaa ctaaaattgt acaaaatatt aggataggg    7380 ctctacaacc atgaacctct ccccgcccct ccccggcatt actagggagt gcactcaagt    7440
cttgagcatg atagaagtgt gaactcctac taagccatgg ccctggtcac caaagtaccc    7500
tcttcccata ccccctgctt ttcactccac gttgcctctc ttgctatcac cccttttccat    7560 gaagaacagg ggtttcttga ccacaaactt ttctccttgg tgtcaaagtt catctctaac    7620
tttctgcagc cagttctgtc cctctctccc aattttttttt tgtttttttgt tctgtttgtt    7680 tgtgtgttttt tgttttttga acagggtttt ctctgtgtag ccttggctgt cctggaactc    7740
actttgtaga ccaggctggc ctcgaactca gaaatctgct tgcctctgcc tcccaagtgc    7800
tgggattaaa ggcgtgtgcc accacgcccg gcttccctca acttttttaaa tggtcttgtt    7860 tttcaggctc taaaagtgct tttatatgtt cctactctaa atgaaatttt gggcaaaaag    7920
tttctctagt cctttgtgaa atggttgtgg gataaaaaaa gggctcccat accctgtgta    7980
gacagcaatc gcatgtaagt gacctgaaga aaggtgtgtg tgggggtgtg tgtctggagg    8040
ggtggggtga tgcaaaggcc acactacaaa gacaagcctg acatgacagg tagttaaacc    8100
aaaggtgcaa attagagggg tggggtggg gggcgcccac aaagccgaga tagactgtcc    8160
aacgctcaat gaacgaagga aaaaaaaaa agaaaggtg tatgttgtgc gctcactcag    8220
tgacaagtgc acaggcagaa cgaggagccc tggagctaaa gatggagcaa gaattgaagg    8280
gagatgggga gggactctg gcagaattaa agggtcttgg gtaggtgcag cagccactga    8340
gggcacagca gaccctggct acttggcagc ctcccctct tcccggctga agcagtgggg    8400
agagctttct agagctgtgc ggaggccggt aggccccgcc cgccgctgcc gccgccgcag    8460
ccgccggagg attcctgtcc taatatggag ctgggattcc cccggcccg ccccgcccc    8520 ccagcccgcc ggagagactg gggctcgcaa gagggcgggg gaacagctcg tcttgggggc    8580
tgacaagcgg gaggggatcg tgggagaggt tcaaacacac atccagatcc tcaccaggcc    8640
ctgggtcttt gcctcagttt ccccgacagg tggctaagat gaactaatag aggaaaaagg    8700
```

-continued

```
aatccctgca gatcacagtg gagatgtttg tgttcctatg gtgctaagga aatatgatca    8760
agaccgaatt caagtggtct cttctccaca ggaccaccat tccaccctat cctggagatt    8820
tagaccctca ggtcagggca tggaggcgaa aaggaatta tttatttgaa actggctaag    8880
ggactttcag attgaataga ccccagaaaa gaccccagt tgtgacctag cccctcccca    8940
aaagccaagg aaagtccctc atgtaatttc gaccctgcc tggcagatgg cggcaaattg    9000
gcagaggacc aagcccttc tcatcctttg cctccttaga aaaatctatg ttgatagcag    9060
cctcgctttg ccttctacaa actctcttgt taagggcttc agaccaccct aatccatgta    9120
ctgttcctcc tcctaataga atgtaatgga aaacctgggt ccctgcaccc cattcctggc    9180
tctgcacagc tcttgccagc cggccccctc tgcaccctcc cttctccccc ttccccgcc    9240 ccctccctct cccgttcgac gtcacgggat gacgtcggaa gtctgggagg gaggaggagc    9300
accccccctc cccagccagt ggctccctct gcagcttgct ttagcccagc ctcccgcctc    9360
ccgctgcccc cccgtctct aaaaacgagc ccccacgcc tgtcaggagc tatataaggc     9420
ggatcgaggc aggcgagggg ggcagcgctg ccgagcggag cccaggagtg gagcgagagc    9480
gagcaagagc ctgagcgaaa agaccgggaa gcaaggaaga ggaagcctcc ggtgcatcgg    9540
gaaaggatcg caggtgctcg ggagccggag ctggagctcc acagccggca gtcatgtacc    9600
gatccaccaa gggcgcctcc aaggcgcgcc gcgaccagat caacgccgag attcggaacc    9660
tcaaggagct gctgccgttg gctgaagcgg acaaggtccg gctgtcctac ctgcacatca    9720
tgagtcttgc ctgcatctac actcgcaagg gtgtcttctt tgctggaggt gagcagcttg    9780
ggctaccgga gaccagagct gacggggacc agggatggag gagctgaggg aatgtgctaa    9840
aactgccgct tgtctagcac agcgtgctgg aagcctgtgg agagaaggga cttgagggga    9900
ccctggactt cctactttt cttctgagct ccatctagac tagcctaaac gatagtccta    9960
gcactggatt tgtgtgagat agagcgctaa aacagaatgg tccaggctcc cattgcctca    10020
gaggcactcc aggaatccgg ggagggtacg gaaggaagcc tggcaagcta cagggaaagc    10080
ctgcaaaggc aaagtatgag gaagagtagc ttgtgctaga aaatgctgag agggtctttc    10140
tatgcgctct ggagctgttc gacgtcctga agccatcacc ctttctggcg ctgcccgcgg    10200
tgctgaaatg gccatagccc cttttcgcag gagctgtccg cggtgctgaa tcccagtcct    10260
ttcgggagag ctctgtccac agtgctgaca gcagagggct gctgaggttc cggccaggct    10320
tggaagtcca ggggctccct ggctagatag ttttagcaac aggtctcctg gccaagatcc    10380
acaagcatag ggtcaacagg tgttggcaga aataggtcta tgggaatttc ctgtgtcttc    10440
tccaagactc aaaagatgtt ctctttattt ctgtgttgtc cctgattctt atcctgactc    10500
accacatctt ctcaccctac aggcactcct ttggctggcc ccaccgggct tctctctgct    10560
caagagcttg aagacattgt ggcagcacta cctggatttc tccttgtatt cacagctgag    10620
gggaagttgc tatacctgtc ggagagtgtg agcgagcatc tgggccactc tatggtgagt    10680
actaaaagtc cttgcatctc aagttggggt atatgtgaga taaatgagc ctctcactac     10740 tgaaaacaga gttattagag gcgagtgtgg gggagtcttc cctaagaaaa atcattggtt    10800
gcagataggc tcttgctgcc ttcactaatg atcacttctc cttctaggt ggacctggtt     10860 gcccagggcg acagtatcta cgatatcatt gaccctgctg accatctcac tgtgcgccag    10920
cagctcacca tgccctctgc tctggatgct ggtaagaacc tcctctcggt tcttcagttt    10980
actcctctgc tgccctgccc taactatcta ctctcctcca atgcccaccc tcttagtcag    11040
tttttccttt tgctcaccta gatcgccttt tccgttgtcg attcaacacc tccaagtccc    11100
```

```
tccggcgcca gagttcagga aacaaactgg tgcttattcg aggtcgattc catgctcacc    11160
cacctggggc ctactgggca ggaaaccctg tgttcaccgc tttctgcgcc ccactggagc    11220
caagaccccg ccctggcccc ggccctggcc ctgccctgg tcctgcttct ctcttcctgg     11280
ccatgttcca gagccggcat gctaaggacc tagccctact ggacgtttct gaaaggtaag    11340
cccaaagtgt tcaaactcca gtaagaaggg aggccagaaa gaagggaact ttagattcgt    11400
gatcttagat tcagggcagg gaggatgggg cttaagtggg cagagagcat gggagggagt    11460
gaagtgcatg cattttgagt aaggtaaaca gaaagctgac ctcatcattt ccaccttccc    11520
agtgtcctaa tctacctggg ctttgagcgc agcgaactgc tctgtaaatc atggtatgga    11580
ctgctacacc ccgaggacct ggcccaagct tcttctcaac actaccgcct gtgtgagtgt    11640
cctgagaggc cgtgcataac acaggaagct gggagaaagc atgggagaca ggccagggac    11700
tggctgtggt ccaaactgat gttaaggagt tcggaggct acagagtgag cttgaggatg     11760
agaagtcaag gcaagaatag gacagagtta gaaaacactg tgtgataagg tcaagtgggg    11820
agcctagagg tacaggttag ggtagttaga agagaatatg tcatggctcc ctcaattcag    11880
tgtagaggta agaaaggtgg gtgtgtaggt ggtgttgatt gatggaccttt ctaatccggt   11940
attccttttt tctccccagt ggctgaaagt ggagatattc aggctgaaat ggtggtgaga    12000
cttcaagcca agcatggagg ctggacatgg atttactgca tgctatactc agaaggtcca    12060
gaaggccctt ttactgccaa taactaccct atcaggtaag ctgtaagata caagatggcg    12120
gagagggggag gggagctgag gtcagcatag aagaaatgca acgaagaaaa ctactctggt   12180
aatggacagc agaccttac aagctgccac ctcttccctt tccagtgaca cggaagcctg     12240
gagcctccgc cagcagctaa actctgaaga cacccaggca gcctatgtcc taggaacccc    12300
agctgtgcta ccctcattct ctgagaatgt cttctcccag gagcaatgct ctaatccact    12360
cttttacacca tccctgggga ctcctagaag tgccagcttc cccagggctc ctgaactagg   12420
tgtgatctca acaccagaag agcttccca accctccaaa gagctggact tcagttacct    12480
gccattccct gctaggcctg agccttccct ccaagcagac ctgagcaagg atttggtgtg   12540
tactccacct tacacacccc accagccagg aggctgtgcc ttcctcttca gcctccatga    12600
acccttccag actcacttgc cccctccgtc cagctctctc caagaacagc tgacaccaag    12660
tacagtgact ttctctgaac agttgacacc cagcagtgct accttcccag acccactaac    12720
cagttcacta caaggacagt tgacagaaag ctcagccaga agctttgaag accagttgac    12780
tccatgcacc tcttccttcc ctgaccagct acttcccagc actgccacat tcccagagcc    12840
tctgggcagc ccgcccatg agcagctgac tcctcccagc acagcattcc aggctcatct    12900
gaacagcccc agccaaacct tcccagagca actgagcccc aatcctacca agacttactt    12960
cgcccaggag ggatgcagtt ttctctatga gaagttgccc ccaagtccta gcagccctgg    13020
taatggggac tgtacactcc tggccctagc tcagctccgg ggccccctct ctgtggatgt    13080
ccccctggtg cccgaaggcc tgctcacacc tgaggcctct ccagtcaagc aaagtttctt    13140
ccactacaca gagaaagagc aaaatgagat agatcgtctc attcagcaga tcagccagtt    13200
ggctcagggc gtggacaggc ccttctcagc tgaggctggc actgggggc tggagccact    13260
tggagggctg gagcccctga accctaacct gtccctgtca ggggctggac cccctgtgct    13320
tagcctggat cttaaaccct ggaaatgcca ggagctggac ttcctggttg accctgataa    13380
tttattcctg gaagagacgc cagtggaaga catcttcatg gatctttcta ctccagaccc    13440
```

```
caatgggaa tggggttcag gggatcctga ggcagaggtc ccaggaggga ccctgtcacc    13500
ttgcaacaac ctgtccccag aagatcacag cttcctggag gacttggcca cctatgaaac   13560
cgcctttgag acaggtgtct caacattccc ctacgaaggg tttgctgatg agttgcatca   13620
actccagagc caagttcaag acagcttcca tgaaggtaag tctagcctga atgtccaaga   13680
gccctgccct tctaatcaga cattgcatag attgggtgaa tcagtcccca actctgaaac   13740
tctgttttat aagagaaca atattacctc ctactaagaa gagtagtgag gtaggaataa    13800
tacaaagctt tgtgtgaaag atgagtagac ctggtgggcg ggggaggtga gctagaaaaa   13860
cgcgatagac aatccctagg caaaagcttg aaagcttctg agagacctag accagacaac   13920
accgtcattt tatagacaaa aataatcaag gccccagagt taaagaaact ttaagtggca   13980 caaaattga tagaagttga tgcttccccc tgaaggggac ccagagcaac aactggttaa    14040
aattaggaga cagaaagaac aatgccaagc ccctagctcc aatctggcgg ccttgtgctg   14100
tttgtccaaa gctgtggcca cagtttccct ccatatttgc atattgcctc ttatctgctg   14160
acaccctggg gatcagttca tttggctaac acatttgacg tccatagact atagcaatat   14220
tgtaccactg cctgagccca atgacgcttt tactgaataa gcttgactaa catacgcact   14280
ttctctcttc tctctctctc tctttcccca cagatggaag tggaggggaa ccaacgtttt   14340
gaataagtct gtgacttaac gtcttcaagt atggcatatt gtcatcaaga cgtgagccg    14400 ctctccaccc ccccgggact gttgggggga ttctgggggc cagaggggga tatatctgat   14460
tctccaggcc ctgaaggatt tagggggag gtggagggt aagggagggg agcaacttt     14520 taaaatcaag agacttcgag cgatcccagt ttccatttca atctgtattc actcgtagtg   14580
agtttccttg aatggatttc aagcggagaa tgggggagtc tcacttcctc accgcgctgc   14640
cccatgggcc tgggccagtt ctccactcct aggggcaaag ccaccctgg gctttggtgg   14700 gggaaaggca tggcccacct ggggctagcc tgtgccccga ggggctcttg cacccacgt   14760 agaattctct acaaaccagt aacgggattt caattccgac ggactctgcc gccctggcgg  14820
ctcttcctgt gacttttgcg ccccgcgcct ggggtggggg gcgcgaagag acgctacatt  14880
cctttccgat ggaggaaggc agatctgccg tcacacgtgt gcttgcacga gtgcgtgtac  14940
ctggtgcggg actcacccgg ccgccagacc gcctaggctt gcccaggtgg ccacctcgtg  15000
gtgctgcggt gactttgtag ccaactttat aataaagtcc agtttgcctt tttggtatct  15060
ctggtgtcat gcgctattgt gaaaagggaa gggaggggaa gggagagatt gaggagccca  15120
gataggaggc tggggcagga gtcacaggtt agacctcctc tcagccctgg tatctctaag  15180
tgagtttgtt catatctcca tttgactctg cttggtccac actgtgctag aagactaagt  15240
acttgtcaga agcagacatt gcaccaaaga cactggagtc ttctctctgc cctgggttta  15300
tggtgtgatg gggaggaaag agcctggggc tgagcaagtt tgtcactggt cttggatatg  15360
ggtttaaagt ttctggtcat ttcctgcctg gtctttcagg atattgattt cctcatggag  15420
gcttagattt taaaaatcag aagctgaaac ctgttacgct tgcgtagggc tgttcagtta  15480
gcaaataccc aatccactgc aataaatttc cacttcattg ggaaagcaac ccgataacgg  15540
gtgttcctcc agttacaggt gagaaacaca tcaaccccctc cccaaatctg gggagctccc  15600
agatctcaat gccagcgaat aaccatcata gaccatctca ccacagagct gaggaccagt  15660
cactggggag gaaatttcag aaaatggtgt tgactctaa actcgtaggc tcaaccccac    15720
agggtgtggt tagtggagga caaatgaaag ttaggtggta aaggacctg acagatccaa    15780 tcacgatccc acctttttgta tttggagtgc acctaaagcc cccacttcct cacaggtcaa   15840
```

```
aggagggcag caatcaagag gcagtgtcag aacaggacaa gtctcttcca gctcacgaag   15900
tgcagtgaag gcttggtcgg tgcgacctcc atttcagtgg tgacccgcag acttagagaa   15960
agccttgtcc tcaaggagag gacaacaact ccaggctcca gtctttccac agaagcacag   16020
gggcacagcc ttgaaaaccc tgtagcctcc actcatcctg aagcccagct gtggagacag   16080
acaggccctt tggagggtcc ttccttcact gtggagacag acaggccctt tggagggtcc   16140
ttccttcact gtggagacag acaggccctt tggagggtcc ttccttcact gtggagacag   16200
gcccttggga tccttccttc acagaaagga aggatccaca gggacctttc ccttctttga   16260
tgggtatttg ggtggagcca agaacttccc tgtcactccc aagaggaacc tgtcttagct   16320
cagttccctc ctcagcacag ggacacggag atggggagat ggataaaggt gctgggccaa   16380
gcatgatgct ctgatttgat ccttgatggg aagagataac tgacagttgt cctctgacgt   16440
gtaactgcac tccaggacat gttacactca catgtgcaca cacacacact acacacacta   16500
catacacata ccatacacat actatacaca ataccacaca cacacacata ctatacacac   16560
ataccacata cactcacacac agtacacatg ctacacatac atacacacac cacacacata   16620
taccacacac aaacactcta cacacacaca ctacacacac tacatacata taccacacac   16680
acttaccaca catacagtat atacagtaca tacatatgcc acacacacat aacacacact   16740
cacacacacc atatatacta ctaatagaaa ataataaaaa ttttttaaatg gggtggattt   16800 aggaaatgaa atttctgtga gaataaagga aaggcttcct tgatgtttgg tggtggctgg   16860
caatagtgta tgctttcttt gtctttgttt gttgtagttt ttttgtttat tttgcttttg   16920
attttttttt tgttgttgtt gttacttgtt tgttgaaaac ctgcctctgc ctcctaagca   16980
ctgaattgtc ttgggtggtt tttaaaaatt aattaatgtt gaaatatttt tttcattttt   17040
gagacaagat ttctttgtgt agccttagct gtcttagaac tagctctgta gactaagctg   17100
gccttaaact tacagagatc tgcttgcttc tgcctcctga gtgctgggat taaagttttt   17160 agttttaaa aaatataat tacagatatg cactgtcttt gcatcatgtc ctcttgtttt   17220
gggcttattt ttgttgttgt ggtggtgata agtgattttt tttgtttgtt tttgttttta   17280
gttttgtttt tcttcagctc aggtcaatct ggagttcact atgtagtcca aggtggccac   17340
agacttttgc aaatccccct gcctcagcct cccaggtgct aggattacag aagaaccaga   17400
ccaactggtc ctgtgtgagg aaaataaagt agaagaggca atactgccac ctgctggaag   17460
gaaaagaagc tgcttccttg ctggctgctg aggcccttgc agctcagaat atcttcacct   17520
tagaatggag agataaactg agtccctggg agagaaaagg acttcaggat ctgagagtga   17580
gtgatgttct ggaagcagag tgcatgagag aaggtgtctt aatcattgta gtactgctgt   17640
gagaagacac catgaccaag gtaacataaa ataaagcatt tagttgggga cttgcttaga   17700
gtttaaaagg gttgctccat gaccagcaga gcagggagca tgggagtatg caggtagaca   17760
cggcactgga gaagtacctg agagcttcca tctgatcccc aagatagagg cagagagaac   17820
cctcaaagcc cacaccccct ccaacaacaa acacctcctg atccttccta aacagtccac   17880
caaatggaga ctaagcattc agatatgggg accattatca tccaaaccac tatggaaggc   17940
tcgagtctgg ggaccagaca gactgaaccc aggagaccaa ggggatagct tagtgggtaa   18000
aggcgctagc tgccgagctt ggagacgcaa gtccaatccc taggttctgt atggtggaaa   18060
gaaacgggat tccagtaagt cacccctgg ccttcgcgca caccatgatg ctcatgccca   18120
cacacataca aatccaaaag aaagaccgaa cctaaggatg gttctgctgt tgtacatttt   18180
```

```
tcctgtaata gatcatccat gacacttgcc tgagttctgg gaaaactgaa caaacaagat    18240
gggtggggcc agacagctgt gctctaactg ggaacatcac aagaggtaag acagagcctg    18300
agtgctgaag gcaagagcta gggtatcgtg acagagtaac cggggactga tttatagtgc    18360
cactttctga gaaggtgaca ctgagcttgt tagcaacagg tgacaacaaa gaagagtcca    18420
acctaaagga agcatctgta atgacattaa aacgggagag tgtctgagct gcttaagaag    18480
tacacaggaa gtgggctgag acaagcagga gaggggctgg agagaaggtc gcccagtact    18540
tctagaccac aataaaagat gtaggttgca ttctggctga gcgtggtagt gcacacctgc    18600
aattgcagcc tcaaaaggcc gagggtggaa atcttgagc tcctggacag cctgggctcc     18660
atagaaagaa aagtctgcaa acaacagcaa caaaaaccc aaccaaaaa ccaaagtgct       18720 ggtgtcctag tgagggttcc tattgctatg aggaaaaaca atgatcaaaa acaaactgcg    18780
gacgaaaggg tttgtttgcc tggcacttcc acatcacagt ccatcattga aggaatccag    18840
aacaggaacg caagcaaggc aggaacctgg aggcaggagc caatgaagag gtcatgaagg    18900
gttgctgctt atggcttgct ccacatggct ttacagcctg ctagatctca gcaccaacag    18960
cctaccatga gcgtggccct cctccatcaa tcactgatta agaaaatgtc ctacacagga    19020
agggaggaag gaagagagag ttaggagcat attggatggg gatagtgaca ggataagatg    19080
tagctactag agtcttctgg tttagatggt gaatctgcca gaatttgcca ctgaaggatt    19140
tagatttaga tttaacataa cttacaagat tagcattcta gttgttgcac ccagagactg    19200
agttaccatt gtttctgaac taagtttgtg tgctgttttt cttcacgcgg tggctcgact    19260
gggttcaaga gagaaaggta cagcggcaaa gcctgggttt gccagatgcg caccacaaag    19320
gcagtggggg tttgaacgat ggggctagca cggcagtggg aactcattga gccgggtgga    19380
gggattttgg agctccaggt cagagagttt gctgagatga gaacaccagg ctggagccat    19440
gtggcctgcc ggtaccttgg cataatgagg gaacttgctg ttcttttta tatttcccac    19500 aacaggtggt gaaccagcat gttggggaag aatccactag aaatgtaaga ttatgccggg    19560
cgtggtggtg ctcgccttta atcccagcac tcgggaggca gaggcaggca gatttctgag    19620
ttcgaggcca gcctggtcta caaagtgagt tccaggacag ccaggctac acagagaaac      19680 cctgtctcga aagacaaaac aaaacaaaac aaacaaaaca aaacaaaacg tatgatcatt    19740
agcctgagag ttagagtttt atttgtttgt ttgtttgttt gttatttaaa atgagtagct    19800
gggtagtgct gacacaagtc atgtggaccc aagcgtggaa ttgaaacaaa gactgtaact    19860
ctgaggtccc ctgctgtggg ggctgcaggc tgttctgagt caggagaaga aggatgaagt    19920
tgcctacttc ttagggcaga gatggattga actgtgaatt tataaaattg gtattatttg    19980
cttttaggaa agatttatat ctgggttttg cctgaatcac atggggattt tcgcccactg    20040
ttcagaatta ggataggaaa aaaatcagtc cctgactcca ggtagaaaag acagtgatta    20100
tcgtctgcta caaacaggta tcaattaact atgtctgtgg ctccctgtag agagctcaaa    20160
agatggatat tataacaggt attaataaaa ttaatgtcac ccaggcagtg gtggcacacg    20220
cctttaatcc cagcacttgg gaggcagagg caggcggatt tctgagttcg aggccagcct    20280
ggtctacaga gtgagttcca gcacagccag ggctacacag agaaaccta tcttgaaaaa     20340 aaaattaaat aaaattaatg tctgtggccc cagtgctgag cagatagaca gtgtaacaag    20400
atggctgctc taggcagaga gctgaacagg aagatggtat gaagatagtt tgctctaaca    20460
cacctcacag gatgctcaaa tcctgtctat gtgggctcca tgggaatctt ttttttaatt    20520
aggtattttc ctcatttaca tttccaatgc tatcccaaaa gtcccccata ccctcctccc    20580
```

```
aacccccccaa ccacccactc ccactttttg gccctggcgt tccctgtac tggggcatat     20640 aaagtttgcg tgtccaatgg gcctctcttt ccagtgatgg ctgactaggc cacctttttga    20700 tacatatgca gctagagtca agagctccgg ggtactggtt agttcataat gttgttccac    20760
ctatagggtt gcaga                                                     20775
```

```
<210> SEQ ID NO 56
<211> LENGTH: 83
<212> TYPE: DNA
<213> ORGANISM: Artificial Sequence
<220> FEATURE:
<223> OTHER INFORMATION: Designed oligonucleotide

<400> SEQUENCE: 56
cgcgtcgagc tcgggtcgga ggactgtcct ccgactgctc gagtcgagct cgggtcggag    60
gactgtcctc cgactgctcg aga                                            83

<210> SEQ ID NO 57
<211> LENGTH: 83
<212> TYPE: DNA
<213> ORGANISM: Artificial Sequence
<220> FEATURE:
<223> OTHER INFORMATION: Designed oligonucleotide

<400> SEQUENCE: 57
cgcgtctcga gcagtcggag gacagtcctc cgacccgagc tcgactcgag cagtcggagg    60
acagtcctcc gacccgagct cga                                            83

<210> SEQ ID NO 58
<211> LENGTH: 52
<212> TYPE: DNA
<213> ORGANISM: Artificial
<220> FEATURE:
<223> OTHER INFORMATION: Oligonucleotide derived from Genbank Accession
      No. J00605

<400> SEQUENCE: 58
gatctcgact ataagaggg caggctgtcc tctaagcgtc accacgactt ca              52

<210> SEQ ID NO 59
<211> LENGTH: 52
<212> TYPE: DNA
<213> ORGANISM: Artificial
<220> FEATURE:
<223> OTHER INFORMATION: Oligonucleotide derived from Genbank Accession
      No. J00605

<400> SEQUENCE: 59
agcttgaagt cgtggtgacg cttagaggac agcctgccct ctttatagtc ga             52

<210> SEQ ID NO 60
<211> LENGTH: 45
<212> TYPE: DNA
<213> ORGANISM: Artificial
<220> FEATURE:
<223> OTHER INFORMATION: Designed oligonucleotide primer for PCR

<400> SEQUENCE: 60
gggcggtacc atacctaggg ccaataggag tgatgagccc atgtc                    45

<210> SEQ ID NO 61
<211> LENGTH: 45
<212> TYPE: DNA
```

-continued

```
<213> ORGANISM: Artificial
<220> FEATURE:
<223> OTHER INFORMATION: Designed oligonucleotide primer for PCR

<400> SEQUENCE: 61
gggcggtacc aacgaggaat ctctcttcct ctccactgtc cgggc          45

<210> SEQ ID NO 62
<211> LENGTH: 45
<212> TYPE: DNA
<213> ORGANISM: Artificial
<220> FEATURE:
<223> OTHER INFORMATION: Designed oligonucleotide primer for PCR

<400> SEQUENCE: 62
gggcggtacc ctgcttaaat tgcttggaga ccagctgtgg accca          45

<210> SEQ ID NO 63
<211> LENGTH: 45
<212> TYPE: DNA
<213> ORGANISM: Artificial
<220> FEATURE:
<223> OTHER INFORMATION: Designed oligonucleotide primer for PCR

<400> SEQUENCE: 63
gggcggtacc ctcagtgaca agtgcacagg cagaacgagg agccc          45

<210> SEQ ID NO 64
<211> LENGTH: 45
<212> TYPE: DNA
<213> ORGANISM: Artificial
<220> FEATURE:
<223> OTHER INFORMATION: Designed oligonucleotide primer for PCR

<400> SEQUENCE: 64
gggcacgcgt tcgcctgcct cgatccgcct tatgtagctc ctgac          45
```

BHLH-PAS PROTEINS, GENES THEREOF AND UTILIZATION OF THE SAME

Figure 1:
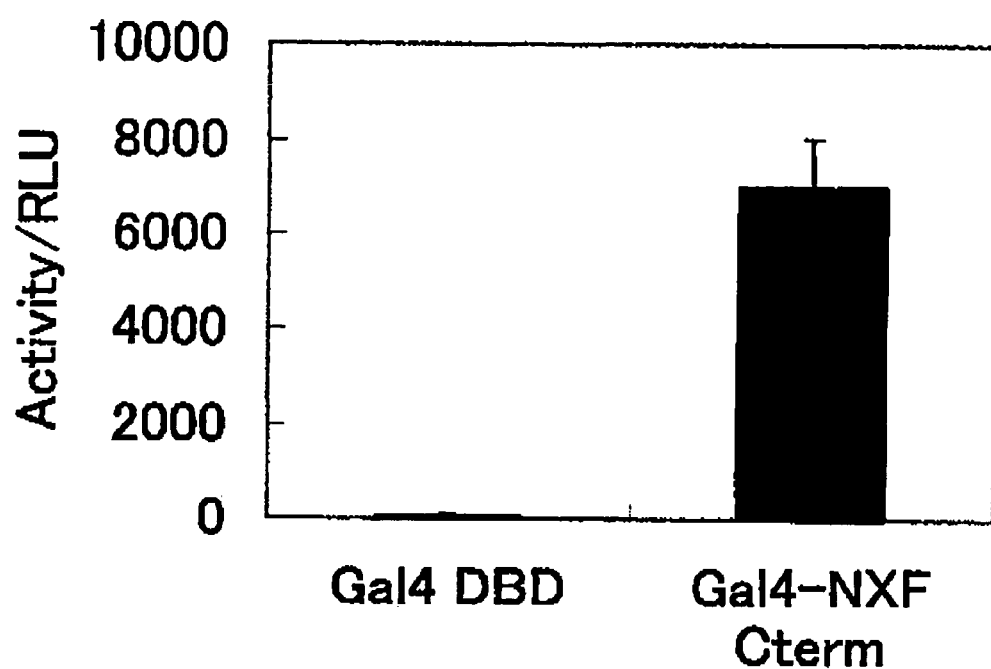

This is a 371 National Stage of PCT/JP01/11064 filed Dec. 17, 2001.

TECHNICAL FIELD

The present invention relates to a bHLH-PAS proteins, genes thereof and utilization of the same.

BACKGROUND ART

A protein having a basic helix-loop-helix (hereinafter referred to as bHLH) motif and a PAS domain (Per-Arnt-Sim homology domain) (such protein hereinafter being referred to as bHLH-PAS protein) binds to a DNA by forming a homodimer or a heterodimer to act as a transcription regulatory factor, whereby playing an important role in the transcriptional regulation of a gene involved in the cell proliferation, development and differentiation, as well as biological function exertion (Annu Rev Pharmacol Toxicol 2000; 40:519–61).

For example, an Ah receptor (aryl hydrocarbon receptor) is activated as a result of the binding of a ligand such as a dioxin to form a heterodimer with an Arnt (AhR nuclear translocator) which is also a bHLH-PAS protein, whereby binding to a transcription regulatory region for example of a drug metabolism enzyme gene, whose transcription is thus activated. An Hif activate the gene expression in a biological response under a hypoxic condition, while Per and Clock are involved in a circadian rhythm control and SRC-1 and TIF2 serve as coactivators of a steroidal hormone receptor family. Since a Sim involved in the development of the median line in a fruit fly is expressed in the median line during the development process also in a mammalian animal such as human, it is considered to be involved in the development of the latter, and a human Sim2 is suggested to be involved also in a genetic disease Down's syndrome (Genome Res 1997; 7:615–624, Chrast, R et al). In addition, NPAS1 and NPAS2 expressed mainly in the central nervous system in an adult are suggested to be involved in a mouse genetic disease exhibiting an abnormality in the nervous functions or behaviors (Proc. Natl. Acad. Sci. USA 1997; 94:713–18), and a knockout mouse whose NPAS 2 gene has been destroyed exhibited an abnormality in a long-term memory (Science 2000; 288:2226–2230).

Thus, a bHLH-PAS protein, in a tissue where it is expressed, is involved in the transcriptional regulation of a gene such as an enzyme gene or structural gene necessary for the development of the such a tissue as well as the exertion of the function, and its malfunction leads to a disease or disorder. Accordingly, in order to develop a means useful in the diagnosis, prophylaxis and therapy of such a disease or disorder, it is highly desirable to obtain a bHLH-PAS protein and a DNA encoding such a protein.

DISCLOSURE OF THE INVENTION

We made an effort under the circumstance described above and were successful finally in isolating a DNA encoding a bHLH-PAS protein which is expressed in a brain, whereby achieving the invention.

Thus, the present invention provides:

1) a DNA encoding any of the proteins (a) to (e):

(a) a protein comprising the amino acid sequence represented by any of SEQ ID NOs:1 to 3, (b) a protein comprising an amino acid sequence exhibiting an amino acid identity of 90% or more to the amino acid sequence represented by any of SEQ ID NOs:1 to 3 and also having a transcription regulation ability, (c) a protein comprising an amino acid sequence encoded by a DNA which hybridizes under a stringent condition with a DNA consisting of the nucleotide sequence represented by the nucleotide numbers 102 to 2507 in the nucleotide sequence represented by SEQ ID NO:4 and also having a transcription regulation ability, (d) a protein comprising an amino acid sequence encoded by a DNA which hybridizes under a stringent condition with a DNA consisting of the nucleotide sequence represented by the nucleotide numbers 51 to 2456 in the nucleotide sequence represented by SEQ ID NO:5 and also having a transcription regulation ability, and (e) a protein comprising an amino acid sequence encoded by a DNA which hybridizes under a stringent condition with a DNA consisting of the nucleotide sequence represented by the nucleotide numbers 35 to 2440 in the nucleotide sequence represented by SEQ ID NO:6 and also having a transcription regulation ability;

2) a DNA comprising any of the nucleotide sequences (a) to (d):

(a) the nucleotide sequence represented by the nucleotide numbers 102 to 2507 in the nucleotide sequence represented by SEQ ID NO:4, (b) the nucleotide sequence represented by the nucleotide numbers 51 to 2456 in the nucleotide sequence represented by SEQ ID NO:5, (c) the nucleotide sequence represented by the nucleotide numbers 35 to 2440 in the nucleotide sequence represented by SEQ ID NO:6, and (d) the nucleotide sequence represented by the nucleotide numbers 1419 to 6164 in the nucleotide sequence represented by SEQ ID NO:54;

3) a vector containing the DNA according to the above-mentioned 1) or 2) (hereinafter referred to as an inventive vector);

4) a vector containing a DNA being formed by operably connecting a promoter to the upstream of the DNA according to the above-mentioned 1) or 2);

5) a method for producing a vector comprising integrating the DNA according to the above-mentioned 1) or 2) into a vector which can replicate itself in a host cell;

6) a transformant being formed by introducing the DNA according to the above-mentioned 1) or 2) or the vector according to the above-mentioned 3) into a host cell (hereinafter referred to as an inventive transformant);

7) a transformant according to the above-mentioned 6) wherein the host cell is an animal cell;

8) a transformant according to the above-mentioned 6) wherein the host cell is a E. coli or yeast;

9) a method for producing a transformant comprising introducing the DNA according to the above-mentioned 1) or 2) or the vector according to the above-mentioned 3) into a host cell;

10) a protein which is any of the following proteins (a) to (e) (hereinafter generally referred to as an inventive protein):

(a) a protein comprising the amino acid sequence represented by any of SEQ ID NOs:1 to 3, (b) a protein comprising an amino acid sequence exhibiting an amino acid identity of 90% or more to the amino acid sequence represented by any of SEQ ID NOs:1 to 3 and also having a transcription regulation ability, (c) a protein comprising an amino acid sequence encoded by a DNA which hybridizes under a stringent condition with a DNA consisting of the nucleotide sequence represented by the nucleotide numbers 102 to 2507 in the nucleotide sequence represented by SEQ ID NO:4 and also having a transcription regulation ability, (d) a protein comprising an amino acid sequence encoded by a DNA which hybridizes under a stringent condition with a DNA consisting of the nucleotide sequence represented by the nucleotide numbers 51 to 2456 in the nucleotide sequence represented by SEQ ID NO:5 and also having a transcription regulation ability, and (e) a protein comprising an amino acid sequence encoded by a DNA which hybridizes under a stringent condition with a DNA consisting of the nucleotide sequence represented by the nucleotide numbers 35 to 2440 in the nucleotide sequence represented by SEQ ID NO:6 and also having a transcription regulation ability;

11) a method for producing an inventive protein comprising culturing a transformant being formed by introducing the DNA encoding any of the following proteins (a) to (e):

(a) a protein comprising the amino acid sequence represented by any of SEQ ID NOs:1 to 3, (b) a protein comprising an amino acid sequence exhibiting an amino acid identity of 90% or more to the amino acid sequence represented by any of SEQ ID NOs:1 to 3 and also having a transcription regulation ability, (c) a protein comprising an amino acid sequence encoded by a DNA which hybridizes under a stringent condition with a DNA consisting of the nucleotide sequence represented by the nucleotide numbers 102 to 2507 in the nucleotide sequence represented by SEQ ID NO:4 and also having a transcription regulation ability, (d) a protein comprising an amino acid sequence encoded by a DNA which hybridizes under a stringent condition with a DNA consisting of the nucleotide sequence represented by the nucleotide numbers 51 to 2456 in the nucleotide sequence represented by SEQ ID NO:5 and also having a transcription regulation ability, and (e) a protein comprising an amino acid sequence encoded by a DNA which hybridizes under a stringent condition with a DNA consisting of the nucleotide sequence represented by the nucleotide numbers 35 to 2440 in the nucleotide sequence represented by SEQ ID NO:6 and also having a transcription regulation ability, into a host cell;

12) an antibody which recognizes an inventive protein or a polypeptide comprising a partial amino acid sequence thereof;

13) a method for detecting an inventive protein comprising:

(1) a step for bringing an antibody which recognizes an inventive protein or a polypeptide comprising a partial amino acid sequence thereof into contact with a test sample, and, (2) a step for detecting a complex of a protein in the test sample and said antibody;

14) a method for screening for a substance which binds to an inventive protein comprising:

(1) a step for bringing an inventive protein or a polypeptide comprising a partial amino acid sequence thereof into contact with a test sample, and, (2) a step for selecting a substance which binds to the inventive protein or said polypeptide;

15) a method for measuring a transcription regulation ability of an inventive protein or a polypeptide comprising a partial amino acid sequence thereof comprising a step for measuring the expression level of a reporter gene in a transformant being formed by introducing a gene i) and gene ii) into a host cell and in a transformant being formed by introducing a gene iii) and gene ii) and then comparing the measured expression levels, said genes being:

i) a chimera gene being formed by connecting, to a downstream of a promoter which is capable of functioning in a host cell, a DNA encoding a fusion protein of a DNA binding region of a transcription regulatory factor which is capable of functioning in the host cell and an inventive protein or a polypeptide comprising a partial amino acid sequence thereof, ii) a reporter gene being formed by connecting a DNA encoding a reporter protein to a downstream of a promoter containing a DNA to which the DNA binding region described in i) can be bound and a minimum promoter which is capable of functioning in a host cell, iii) a gene being formed by connecting, in the downstream of the promoter described in i), a DNA encoding the DNA binding region described in i);

16) a method for screening for a substance which alters the transcription regulation ability of an inventive protein or a polypeptide comprising a partial amino acid sequence thereof comprising:

(1) a step for bringing a transformant being formed by introducing:

i) a chimera gene being formed by connecting, to a downstream of a promoter which is capable of functioning in a host cell, a DNA encoding a fusion protein of a DNA binding region of a transcription regulatory factor which is capable of functioning in the host cell and an inventive protein or a polypeptide comprising a partial amino acid sequence thereof, and, ii) a reporter gene being formed by connecting a DNA encoding a reporter protein to a downstream of a promoter containing a DNA to which the DNA binding region described in i) can be bound and a minimum promoter which is capable of functioning in a host cell, into a host cell into contact with a test substance and then measuring the expression level of said reporter gene in the presence of the test substance, and, (2) a step for selecting a test substance which results in a expression level of said reporter gene, as measured in the step (a), which is different substantially from the expression level of said reporter gene in the absence of the test substance;

17) a use of the DNA according to the above-mentioned 1 for a two-hybrid assay;

18) a method for screening for a substance which alters the intracellular expression level of an inventive protein or a polypeptide comprising a partial amino acid sequence thereof comprising:

(1) a step for bringing a transformant being formed by introducing into a host cell a reporter gene obtained by ligating in a functional manner the expression regulation region of a DNA encoding said protein into contact with a test substance and then measuring the expression level of said reporter gene in the presence of the test substance, and, (2) a step for selecting a test substance which results in a expression level of said reporter gene, as measured in the step (1), which is different substantially from the expression level of said reporter gene in the absence of the test substance;

19) a polynucleotide consisting of 10 to 5000 nucleotides capable of hybridizing under a stringent condition with a polynucleotide consisting of the nucleotide sequence represented by SEQ ID NO:4, 5, 6 or 54 or the nucleotide sequence complementary to said nucleotide sequence;

20) a polynucleotide consisting of 10 to 5000 nucleotides comprising a partial nucleotide sequence of the nucleotide sequence represented by SEQ ID NO:4, 5, 6 or 54 or the nucleotide sequence complementary to said partial nucleotide sequence;

21) a method for detecting a nucleic acid encoding an inventive protein comprising:

(1) a step for bringing a polynucleotide consisting of 10 to 5000 nucleotides capable of hybridizing under a stringent condition with a polynucleotide consisting of the nucleotide sequence represented by SEQ ID NO:4, 5, 6 or 54 or the nucleotide sequence complementary to said nucleotide sequence into contact with a nucleic acid derived from a test sample under a hybridization condition, and, (2) a step for detecting a hybrid of said polynucleotide and the nucleic acid derived from the test sample;

22) a polynucleotide consisting of 10 to 50 nucleotides capable of being annealed under a polymerase chain reaction condition with a polynucleotide consisting of the nucleotide sequence represented by SEQ ID NO:4, 5, 6 or 54 or the nucleotide sequence complementary to said nucleotide sequence;

23) a polynucleotide consisting of 10 to 50 nucleotides comprising a partial nucleotide sequence of the nucleotide sequence represented by SEQ ID NO:4, 5, 6 or 54 or the nucleotide sequence complementary to said partial nucleotide sequence;

24) a polynucleotide consisting of 10 to 50 nucleotides capable of being annealed under a polymerase chain reaction condition with a polynucleotide consisting of the nucleotide sequence represented by any of SEQ ID NOs:43 to 51 or the nucleotide sequence complementary to said nucleotide sequence;

25) a polynucleotide consisting of 10 to 50 nucleotides comprising a partial nucleotide sequence of the nucleotide sequence represented by any of SEQ ID NOs:43 to 51 or the nucleotide sequence complementary to said partial nucleotide sequence;

26) a polynucleotide comprising the nucleotide sequence represented by any of SEQ ID NOs:11 to 42;

27) a kit comprising one or more polynucleotides selected from the following polynucleotides (a) to (f) (hereinafter sometimes referred to as an inventive kit):

(a) a polynucleotide consisting of 10 to 5000 nucleotides capable of hybridizing under a stringent condition with a polynucleotide consisting of the nucleotide sequence represented by SEQ ID NO:4, 5, 6 or 54 or the nucleotide sequence complementary to said nucleotide sequence, (b) a polynucleotide consisting of 10 to 50 nucleotides capable of being annealed under a polymerase chain reaction condition with a polynucleotide consisting of the nucleotide sequence represented by SEQ ID NO:4, 5, 6 or 54 or the nucleotide sequence complementary to said nucleotide sequence, (c) a polynucleotide consisting of 10 to 5000 nucleotides comprising a partial nucleotide sequence of the nucleotide sequence represented by SEQ ID NO:4, 5, 6 or 54 or the nucleotide sequence complementary to said partial nucleotide sequence, (d) a polynucleotide consisting of 10 to 50 nucleotides capable of being annealed under a polymerase chain reaction condition with a polynucleotide consisting of the nucleotide sequence represented by any of SEQ ID NOs:43 to 51 or the nucleotide sequence complementary to said nucleotide sequence, (e) a polynucleotide consisting of 10 to 50 nucleotides comprising a partial nucleotide sequence of the nucleotide sequence represented by any of SEQ ID NOs:43 to 51 or the nucleotide sequence complementary to said partial nucleotide sequence, and (f) a polynucleotide comprising the nucleotide sequence represented by any of SEQ ID NOs:11 to 42;

28) a method for amplifying a genomic DNA encoding an inventive protein comprising a step for conducting a polymerase chain reaction using one or more polynucleotides selected from polynucleotides (f) to (j) as primers together with the genomic DNA as a template, said polynucleotides being:

(f) a polynucleotide consisting of 10 to 50 nucleotides capable of being annealed under a polymerase chain reaction condition with a polynucleotide consisting of the nucleotide sequence represented by SEQ ID NO:4, 5, 6 or 54 or the nucleotide sequence complementary to said nucleotide sequence, (g) a polynucleotide consisting of 10 to 50 nucleotides comprising a partial nucleotide sequence of the nucleotide sequence represented by SEQ ID NO:4, 5, 6 or 54 or the nucleotide sequence complementary to said partial nucleotide sequence, (h) a polynucleotide consisting of 10 to 50 nucleotides capable of being annealed under a polymerase chain reaction condition with a polynucleotide consisting of the nucleotide sequence represented by any of SEQ ID NOs:43 to 51 or the nucleotide sequence complementary to said nucleotide sequence, (i) a polynucleotide consisting of 10 to 50 nucleotides comprising a partial nucleotide sequence of the nucleotide sequence represented by any of SEQ ID NOs:43 to 51 or the nucleotide sequence complementary to said partial nucleotide sequence, and (j) a polynucleotide comprising the nucleotide sequence represented by any of SEQ ID NOs:11 to 42;

29) a method for amplifying a cDNA encoding an inventive protein comprising a step for conducting a polymerase chain reaction using one or more polynucleotides selected from polynucleotide (f) or (g) as primers together with the cDNA as a template, said polynucleotides being:

(f) a polynucleotide consisting of 10 to 50 nucleotides capable of being annealed under a polymerase chain reaction condition with a polynucleotide consisting of the nucleotide sequence represented by any of SEQ ID NOs:4 to 6 or the nucleotide sequence complementary to said nucleotide sequence, and (g) a polynucleotide consisting of 10 to 50 nucleotides comprising a partial nucleotide sequence of the nucleotide sequence represented by any of SEQ ID NOs:4 to 6 or the nucleotide sequence complementary to said partial nucleotide sequence;

30) a method for analyzing a genotype of a gene encoding an inventive protein comprising a step for investigating whether a nucleotide sequence encoding the inventive protein, in a nucleic acid in a test sample, contains a nucleotide sequence encoding an amino acid sequence which is different from the amino acid sequence of a standard protein or not;

31) a method according to the above-mentioned 30) wherein the step for investigating whether a nucleotide sequence encoding the amino acid sequence which is different from the amino acid sequence of a standard protein is contained or not comprises a step for amplifying a DNA encoding an inventive protein using the nucleic acid in the test sample as a template and then determining the nucleotide sequence of the amplified DNA;

32) a method according to the above-mentioned 30) wherein the step for investigating whether a nucleotide sequence encoding the amino acid sequence which is different from the amino acid sequence of a standard protein is contained or not comprises a step for amplifying a DNA encoding the amino acid sequence of an inventive protein using the nucleic acid in the test sample as a template and then subjecting the amplified DNA to an electrophoresis to measure the mobility;

33) a method according to the above-mentioned 30) wherein the step for investigating whether a nucleotide sequence encoding the amino acid sequence which is different from the amino acid sequence of a standard protein is contained or not comprises a step for investigating the pattern of a hybridization under a stringent condition between the nucleic acid of a test sample or an amplification product of said nucleic acid and a polynucleotide consisting of 10 to 5000 nucleotides capable of hybridizing under a stringent condition with a polynucleotide consisting of the nucleotide sequence represented by SEQ ID NO:4, 5, 6 or 54 or the nucleotide sequence complementary to said nucleotide sequence;

34) a method according to any of the above-mentioned 30) to 33) wherein the amino acid sequence of the standard protein is the amino acid sequence represented by SEQ ID NO:1, 2 or 3;

35) a method for promoting the expression of a drebrin 1 in a mammalian cell comprising a step for providing the mammalian cell with the DNA according to the above-mentioned 1 or 2 in a position enabling the expression of said DNA in said cell (hereinafter sometimes referred to as an inventive expression promoting method);

36) a method according to the above-mentioned 35 wherein said mammalian cell is a cell present in a body of a mammalian animal which can be diagnosed to suffer from a disease accompanied with a mental retardation or from Alzheimer's disease;

37) a gene therapy agent comprising the DNA according to the above-mentioned 1 or 2 as an active ingredient and obtained by formulating said active ingredient in a pharmaceutically acceptable carrier.

BRIEF DESCRIPTIONS OF THE DRAWINGS

FIG. 1 shows the results of the one hybrid assay using pGL3-TATA-Galx4 which is a reporter gene plasmid for verifying the transcription regulation ability of an inventive protein. The abscissa represents the tested transformants (the right side is a transformant which expresses a Gal4 DNA binding region exclusively and corresponds to a control, while the left side is a transformant which expresses a fusion protein formed by binding a Gal4 DNA binding region to an inventive protein transcrptional regulation region). The ordinate represents the measured values of the luciferase activity (i.e., the expression levels of the reporter gene), each of which is an index of the transcription regulation ability of a transcription regulatory factor.

Figure 2:
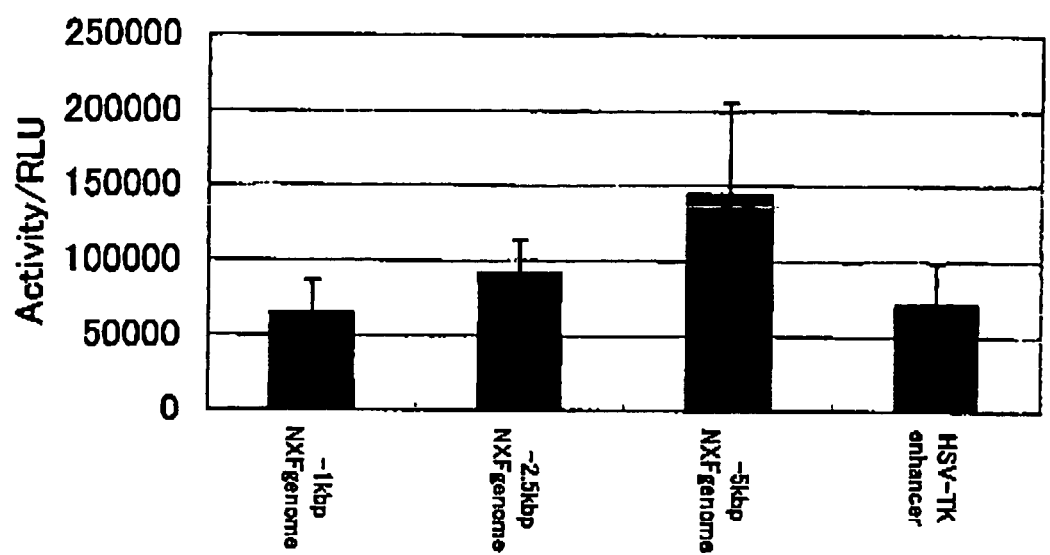

FIG. 2 shows the results of a reporter gene assay for verifying the promoter activity possessed by the expression regulation region of a DNA encoding an inventive protein. The abscissa represents the tested expression regulation region. Starting from the left end, the bars represents the inventive protein-encoding DNA expression regulation regions containing the regions from the inventive protein gene transcription initiation point to the upstream by about 1 kbp, 2.5 kbp and 5 kbp (in the figure, designated as −5 kbp NXF genome, −2.5 kbp NXF genome and −1 kbp NXF genome) and a herpes simplex virus thymidine kinase promoter (HSV-TK enhancer) as a control. The ordinate represents the measured values of the luciferase activity (i.e., the expression levels of the reporter gene), each of which is an index of the promoter activity possessed by the expression regulation region of a protein gene.

BEST MODE FOR CARRYING OUT THE INVENTION

The invention is further detailed below.

An inventive protein includes a protein comprising the amino acid sequence represented by any of SEQ ID NOs:1 to 3 (wherein the transcription regulatory factor comprising the amino acid sequence represented by SEQ ID NO:1 is a human-derived inventive transcription regulatory factor, which may sometimes be designated as hNXF; the transcription regulatory factor comprising the amino acid sequence represented by SEQ ID NO:2 is a mouse-derived inventive transcription regulatory factor, which may sometimes be designated as mNXF; the transcription regulatory factor comprising the amino acid sequence represented by SEQ ID NO:3 is a rat-derived inventive transcription regulatory factor, which may sometimes be designated as rNXF), a protein comprising an amino acid sequence exhibiting an amino acid identity of 90% or more to the amino acid sequence represented by any of SEQ ID NOs:1 to 3 and also having a transcription regulation ability, a protein comprising an amino acid sequence encoded by a DNA which hybridizes under a stringent condition with a DNA consisting of the nucleotide sequence represented by the nucleotide numbers 102 to 2507 in the nucleotide sequence represented by SEQ ID NO:4 and also having a transcription regulation ability, a protein comprising an amino acid sequence encoded by a DNA which hybridizes under a stringent condition with a DNA consisting of the nucleotide sequence represented by the nucleotide numbers 51 to 2456 in the nucleotide sequence represented by SEQ ID NO:5 and also having a transcription regulation ability and a protein comprising an amino acid sequence encoded by a DNA which hybridizes under a stringent condition with a DNA consisting of the nucleotide sequence represented by the nucleotide numbers 35 to 2440 in the nucleotide sequence represented by SEQ ID NO:6 and also having a transcription regulation ability.

The difference from the amino acid sequence represented by any of SEQ ID NOs:1 to 3 observed in the amino acid sequence of an inventive protein may for example be a variation such as the deletion, substitution, modification and addition of amino acids. Such a variation includes a variation which can artificially be introduced by means of a site-directed mutagenesis method or a mutagenic treatment as well as a polymorphic variation which occurs naturally such as a difference in an amino acid sequence resulting from the difference by the animal line, individual, organ and tissue.

In the invention, the "amino acid identity" means an identity and a homology in the amino acid sequence between two proteins. The "amino acid identity" described above can be determined by comparing two amino acid sequence which are aligned optimally over the entire range of a reference amino acid. A reference protein here may have an addition or deletion (for example, a gap) in the optimal alignment of the two amino acid sequences. Such an amino acid identity can be calculated for example by producing an alignment utilizing a Clustal W algorism [Nucleic Acid Res., 22 (22): 4673–4680 (1994)] using a Vector NTI. The amino acid identity can be investigated also by using a sequence analysis software, typically Vector NTI, GENETYX-MAC or any other analytical tools provide DNA public database.

A preferred amino acid identity in the invention may for example be 90% or higher.

A "DNA which hybridizes under a stringent condition" described above may for example be a DNA capable of maintaining a hybrid, which was formed previously as a DNA-DNA hybrid by a hybridization at 65° C. at a high ion concentration [for example using 6×SSC (900 mM sodium chloride, 90 mM sodium citrate)], even after washing for 30 minutes at 65° C. at a low ion concentration [for example using 0.1×SSC (15 mM sodium chloride, 1.5 mM sodium citrate)]. The transcription regulation ability of an inventive protein can be evaluated based for example on an assay using a reporter gene described below.

A DNA encoding an inventive protein (hereinafter referred to as an inventive DNA) can be obtained in accordance with a genetic engineering method described in J. Sambrook, E. F. Frisch, T. Maniatis, Molecular Cloning, 2nd Edition, Cold Spring Harbor Laboratory, 1989, from a tissue of an animal such as human, mouse, rat and the like.

Typically, a total RNA derived from a tissue of an animal such as human, mouse and rat is first prepared. For example, a brain tissue is pulverized in a solution containing a protein denaturant such as guanidine hydrochloride or guanidine thiocyanate, and then the pulverized material is treated with phenol, chloroform and the like, to denature the protein. The denatured protein is removed for example by a centrifugation to obtain a supernatant, from which the total RNA is extracted by a guanidine hydrochloride/phenol method, SDS-phenol method, guanidine thiocyanate/CsCl method and the like. A commercially available kit based on the methods described above may for example be ISOGEN (NIPPON GENE). The resultant total RNA is used as a template and an oligo dT primer is annealed to a poly A sequence of the RNA, whereby synthesizing a single-stranded cDNA using a reverse transcriptase. Then, the synthesized single-stranded cDNA is used as a template together with a primer which is an RNA obtained by inserting a nick and a gap into the RNA chain using an E. coli RnaseH, whereby synthesizing a double-stranded cDNA using an E. coli DNA polymerase I. Subsequently, the both ends of the synthesized double-stranded cDNA is made blunt using a T4 DNA polymerase. The double-stranded cDNA having both blunt ends is purified and recovered by means of a standard procedure such as a phenol-chloroform extraction and ethanol precipitation. A commercially available kit based on the methods described above may for example be a cDNA synthesis system plus (Amarsham Pharmacia Biotech) or a TimeSaver cDNA synthesis kit (Amarsham Pharmacia Biotech). Then the resultant double-stranded cDNA is ligated to a vector such as a plasmid pUC118 or phage λgt10 using a ligase to prepare a cDNA library. As such a cDNA library, a commercially available cDNA library (GIBCO-BPL or Clontech) may also be employed.

Alternatively, a genomic DNA may be prepared from a tissue sample of an animal such as human, mouse and rat in accordance with a standard method described for example in J. Sambrook, E. F. Frisch, T. Maniatis, Molecular Cloning, 2nd Edition, Cold Spring Harbor Laboratory (1989), or M. Muramatsu, "Labomanual genetic engineering" (Maruzen, 1988). For example, when the sample is a hair, 2 or 3 hairs are washed with a sterilized water and then with ethanol, cut into 2 to 3 mm pieces, which are combined with 200 μl of a BCL-Buffer [10 mM Tris-HCl (pH7.5), 5 mM $MgCl_2$, 0.32 sucrose, 1 Triton X-100] followed by a Proteinase K at the final concentration of 100 μl/ml and SDS at the final concentration of 0.5 (w/v). The mixture thus obtained is incubated at 70° C. for 1 hour, and then subjected to a phenol/chloroform extraction to obtain a genomic DNA. When the sample is a peripheral blood, the sample is treated using a DNA-Extraction kit (Stratagene) and the like to obtain a genomic DNA. The resultant genomic DNA is ligated to a vector such as a λgt10 using a ligase to obtain a genomic DNA library. As such a genomic DNA library, a commercially available genomic DNA library (Stratagene) may also be employed.

From a cDNA library or genomic DNA library obtained as described above, an inventive DNA can be obtained for example by a polymerase chain reaction (hereinafter abbreviated as PCR) using as a primer an oligonucleotide comprising a partial nucleotide sequence of the nucleotide sequence represented by SEQ ID NO:4, 5, 6 or 54 or the nucleotide sequence complementary to said partial nucleotide sequence or by a hybridization method using as a probe a DNA comprising the nucleotide sequence represented by SEQ ID NO:4, 5, 6 or 54 or a partial nucleotide sequence of said partial nucleotide sequence.

A primer employed in a PCR may for example be an oligonucleotide having a length of about 10 nucleotides to about 50 nucleotides which is an oligonucleotide comprising a nucleotide sequence selected from a 5' non-translation region of the nucleotide sequence represented by SEQ ID NO:4, 5, 6 or 54 and which is an oligonucleotide comprising the nucleotide sequence complementary to a nucleotide sequence selected from a 3' non-translation region of the nucleotide sequence represented by SEQ ID NO:4, 5, 6 or 54. Typically, the forward primer may for example be the oligonucleotide consisting of the nucleotide sequence represented by SEQ ID NO:7 and the oligonucleotide consisting of the nucleotide sequence represented by SEQ ID NO:8. The reverse primer may for example be the oligonucleotide consisting of the nucleotide sequence represented by SEQ ID NO:9 and the oligonucleotide consisting of the nucleotide sequence represented by SEQ ID NO:10. An example of the PCR condition involves an incubation in 50 μl of a reaction solution containing 5 μl of a 10-fold diluted buffer for a LA-Taq polymerase (Takara), 5 μl of a 2.5 mM dNTP mixture (each 2.5 mM dATP, dGTP, dCTP and dTTP) (the final concentration of each of dATP, dGTP, dCTP and dTTP is 0.25 mM), each 0.25 to 1.25 μl of 20 μM primers (final concentration of 0.1 to 0.5 μM), 0.1 to 0.5 μg of a template cDNA and 1.25 units of a LA-Taq polymerase (Takara) for 1 minutes at 95° C. followed by 3 minutes at 68° C. in a single cycle, the cycle being repeated 35 times.

A probe employed in a hybridization method may for example be the DNA consisting of the nucleotide sequence represented by the nucleotide numbers 102 to 2507 in the nucleotide sequence represented by SEQ ID NO:4, a DNA consisting of the nucleotide sequence represented by the nucleotide numbers 51 to 2456 in the nucleotide sequence represented by SEQ ID NO:5, a DNA consisting of the nucleotide sequence represented by the nucleotide numbers 35 to 2440 in the nucleotide sequence represented by SEQ ID NO:6, a DNA consisting of the nucleotide sequence represented by the nucleotide numbers 1419 to 6164 in the nucleotide sequence represented by SEQ ID NO:54 and the like. An example of the hybridization condition involves an incubation at 65° C. in the presence of 6×SSC (0.9M sodium chloride, 0.09M sodium citrate), 5× Denhart's solution (0.1 (w/v) ficoll 400, 0.1 (w/v) polyvinyl pyrrolidone), 0.1 (w/v) BSA), 0.5 (w/v) SDS and 100 μg/ml denatured salmon sperm DNA followed by an incubation at room temperature for 15 minutes in the presence of 1×SSC (0.15M sodium chloride, 0.015M sodium citrate) and 0.5 (w/v) SDS, followed by an incubation at 68° C. for 30 minutes in the presence of 0.1×SSC (0.015M sodium chloride, 0.0015M sodium citrate) and 0.5 (w/v) SDS. Alternatively, an incubation at 65° C. in the presence of 5×SSC, 50 mM HEPES, pH7.0, 10× Denhart's solution and 20 μg/ml denatured salmon sperm DNA followed by an incubation at room temperature for 30 minutes in 2×SSC, followed by an incubation at 65° C. for 40 minutes in 0.1×SSC, which is repeated twice, may also be exemplified.

An inventive DNA can be prepared also by performing a chemical synthesis of a nucleic acid in accordance with a standard method such as a phosphite triester method (Hunkapiller, M. et al., Nature, 310, 105, 1984) based on the nucleotide sequence represented by SEQ ID NO:4, 5, 6 or 54.

An inventive DNA thus obtained can be cloned into a vector in accordance with a genetic engineering method described in J. Sambrook, E. F. Frisch, T. Maniatis, Molecular Cloning, 2nd Edition, Cold Spring Harbor Laboratory (1989). Typically, the cloning can for example be performed using a TA cloning kit (Invitrogen) or a commercially available plasmid vector such as pBluescriptII (Stratagene).

The nucleotide sequence of a resultant inventive DNA can be identified by a Maxam Gilbert method (described for example in Maxam, A. M. & W. Glibert, Proc. Natl. Acad. Sci. USA, 74, 560, 1997) or a Sanger method (described for example in Sanger, F. & A. R. Coulson, J. Mol. Biol., 94, 441, 1975, Sanger, F. & Nicklen and A. R. Coulson., Proc. Natl. Acad. Sci. USA, 74, 5463, 1997).

A typical example of an inventive DNA may for example be the DNA consisting of the nucleotide sequence represented by the nucleotide numbers 102 to 2507 in the nucleotide sequence represented by SEQ ID NO:4, a DNA consisting of the nucleotide sequence represented by the nucleotide numbers 51 to 2456 in the nucleotide sequence represented by SEQ ID NO:5, a DNA consisting of the nucleotide sequence represented by the nucleotide numbers 35 to 2440 in the nucleotide sequence represented by SEQ ID NO:6, a DNA consisting of the nucleotide sequence represented by the nucleotide numbers 1419 to 6164 in the nucleotide sequence represented by SEQ ID NO:54 and the like.

An inventive DNA has an ability of promoting the expression of a drebrin 1 as evident from the Examples described below. In this context, the drebrin 1 is depleted in a cell of an Alzheimer's disease patient, and the suppression of it may contribute to the recovery from the cognition dysfunction and the memory insufficiency in the Alzheimer's disease. Accordingly, an inventive DNA is useful as an active ingredient in a gene therapy pharmaceutical.

An inventive vector can be constructed by integrating an inventive DNA, in accordance with a standard genetic engineering method, into a vector capable of being utilized in a host cell to which said gene is introduced (hereinafter referred to as a basic vector), such as a vector which contains a gene information capable of being replicated in the host cell, which can independently be proliferated, which can be isolated and purified from the host cell and which has a detectable marker.

A basic vector which can be employed for constructing an inventive vector may for example be a plasmid pUC119 (Takara) or phagimid pBluescriptII (Stratagene) when using a coliform as a host cell. When using a budding yeast as a host cell, then plasmids pGBT9, pGAD242, pACT2 (Clontech) may be exemplified. When using a mammalian cell as a host cell, a vector containing an autonomous replication origin derived from a virus such as pRc/RSV, pRc/CMV (Invitrogen), bovine papilloma virus plasmid pBV (Amarsham Pharmacia Biotech) or EB virus plasmid pCEP4 (Invitrogen) and a virus such as a vaccinia virus may be exemplified, while an insect virus such as a baculovirus may be exemplified when using a insect cell as a host cell.

In order to integrate an inventive DNA into a virus such as a baculovirus or vaccinia virus, a transfer vector containing a nucleotide sequence homologous to the genome of a virus to be employed can be used. Such a transfer vector is typically a plasmid available from Pharmingen such as pVL1372, pVL1393 (Smith, G. E., Summers M. E. et al., Mol. Cell Biol., 3, 2156–2165 (1983) and pSFB5 (Funahashi, S. et al., J. Virol., 65, 5584–5588 (1991). When an inventive DNA is inserted into a transfer vector described above and the transfer vector and the genome of a virus are introduced into a host cell simultaneously, a homologous recombination occurs between the transfer vector and the genome of the virus, whereby obtaining a virus into whose genome the inventive gene is integrated. The genome of a virus may be the genome for example of Baculovirus, Adenovirus, Vacciniavirus and the like.

More specifically, an inventive gene is integrated for example into a baculovirus by inserting the inventive DNA into a multiple cloning site of a transfer vector such as pVL1393 or pBL1392 followed by introducing the DNA of said transfer vector and a baculovirus genomic DNA (Baculogold; Pharmingen) into an insect cell line Sf21 (available from ATCC) for example by a calcium phosphate method followed by incubating the resulting cell. A virus particle containing the genome of the virus into which the inventive DNA has been inserted is recovered from the culture medium for example by a centrifugation, and then made free from proteins using phenol and the like, whereby obtaining the genome of the virus containing the inventive DNA. Subsequently, the genome of said virus is introduced into a host cell having a virus particle forming ability such as an insect cell line Sf21 for example by a calcium phosphate method and the resultant cell is incubated, whereby proliferating the virus particle containing the inventive DNA.

On the other hand, a relatively small genome such as that of a mouse leukemia retrovirus can directly be integrated with an inventive DNA without using any transfer vector. For example, a virus vector DC(X) (Eli Gilboa et al., BioTechniques, 4, 504–512 (1986)) is integrated with an inventive DNA on its cloning site. The resultant virus vector into which the inventive DNA has been integrated is introduced into a packaging cell such as an Ampli-GPE (J. Virol., 66, 3755 (1992)), whereby obtaining a virus particle containing the genome of the virus into which the inventive DNA has been inserted.

A promoter capable of functioning in a host cell is operably connected to the upstream of an inventive DNA and then integrated into a basic vector such as those described above, whereby constructing an inventive vector capable of allowing the inventive DNA to be expressed in the host cell. The expression "operably connected" means that a promoter and an inventive gene are bound to each other in a condition which allows the inventive DNA is expressed under the control of the promoter in a host cell into which the inventive DNA is to be introduced. A promoter capable of functioning in a host cell may for example be a DNA exhibiting a promoter activity in a host cell into which it is to be introduced. Those which may be exemplified when the host cell is a coliform cell are $E.$ $coli$ lactose operon promoter (lacP), tryptophan operon promoter (trpP), arginine operon promoter (argP), galactose operon promoter (galP), tac promoter, T7 promoter, T3 promoter, λ phage promoter (λ-pL, λ-pR) and the like, while those which may be exemplified when the host cell is an animal cell or fission yeast are Rous sarcoma virus (RSV) promoter, cytomegalovirus (CMV) promoter, simian virus (SV40) early or late promoter, mouse mammary tumor virus (MMTV) promoter and the like. Those which may be exemplified when the host cell is a budding yeast are an ADH1 promoter and the like (the ADH1 promoter can be prepared by a standard genetic engineering method for example from an yeast expression vector pAAH5 comprising an ADH1 promoter and terminator [available from Washington Research Foundation, Ammerer et al., Method in Enzymology, 101 part (p. 192–201)]; the ADH1 promoter is encompassed in the U.S. patent application Ser. No. 299,733 by Washington Research Foundation, and should be used industrially or commercially in United States only after obtaining the approval from the claimant).

When a basic vector which initially possesses a promoter capable of functioning in a host cell is employed, an inventive DNA may be inserted to the downstream of said promoter so that the vector-possessed promoter and the inventive DNA are operably connected to each other. For example, each of the plasmids such as pRc/RSV and pRc/CMV described above is provided with a cloning site downstream of a promoter capable of functioning in an animal cell, and by inserting an inventive DNA into said cloning site followed by a introduction into an animal cell, the inventive DNA can be expressed. Since any of these plasmids has previously been integrated with a SV40 autonomous replication origin, the introduction of said plasmid into a host cell which has been transformed with an SV40 genome from which an ori is deleted, such as a COS cell, leads to an extremely increased number of the intracellular plasmid copies, resulting in a high expression of the inventive DNA which has been integrated into said plasmid. Also since the plasmid pACT2 for yeast described above possesses an ADH1 promoter, an inventive vector capable of allowing an inventive DNA to be expressed highly in a budding yeast such as CG1945 (Clontech) can be constructed by inserting the inventive DNA into the downstream of the ADH1 promoter of said plasmid or a derivative thereof.

Furthermore, by binding an inventive DNA or a DNA comprising its partial nucleotide sequence and a DNA encoding other desired protein to each other with aligning their reading frames upstream of which a promoter capable of functioning in a host cell is then operably connected and then integrated into a basic vector described above, it is possible to construct an inventive vector capable of allowing a DNA encoding a fusion protein with said desired protein to be expressed in the host cell. Such a construction of an inventive vector may also employ a basic vector which originally possesses a promoter capable of functioning in a host cell and a DNA encoding a desired protein described above. When a DNA encoding a fusion protein of an inventive protein or a polypeptide comprising its partial amino acid sequence with a Gal4 DNA binding region is intended to be expressed, a pGBT9 or pAS2 (Clontech) when the host cell is a budding yeast and a pM vector (Clontech) when the host cell is an animal cell may for example be employed. When a DNA encoding a fusion protein of an inventive protein or a polypeptide comprising its partial amino acid sequence with a LexA DNA binding region is intended to be expressed, a pGilda vector for a budding yeast expression (Clontech) may for example be employed. When a DNA encoding a fusion protein of an inventive protein or a polypeptide comprising its partial amino acid sequence with a glutathion S transferase (hereinafter designated as GST) is intended to be expressed, a pGEX series for a coliform expression (Amersham Pharmacia) may for example be employed.

By introducing a constructed inventive vector into a host cell, an inventive transformant can be obtained. A method for introducing an inventive vector into a host cell may be a standard introducing method suitable for the host cell. For example, when $E.$ $coli$ is employed as a host cell, a standard method such as a calcium chloride method or electroporation described for example in J. Sambrook, E. F. Frisch, T.

Maniatis, Molecular Cloning, 2nd Edition, Cold Spring Harbor Laboratory (1989) may be employed. When a mammalian cell or insect cell is employed as a host cell, the introduction into a cell described above can be effected in accordance with a general gene introduction method such as a calcium phosphate method, DEAE dextran method, electroporation, lipofection and the like. When an yeast is employed as a host cell, the introduction can be effected for example by means of an Yeast transformation kit (Clontech) based on a lithium method.

When a virus is employed as a vector, the genome of the virus can be introduced into a host cell by a standard gene introduction method described above, or a virus particle containing the genome of the virus into which an inventive DNA has been inserted is infected to a host cell, whereby introducing the genome of said virus into the host cell.

In order to screen for an inventive transformant, a marker gene is introduced into a host cell simultaneously with an inventive vector and the cell is cultured in a manner suitable to the nature of the marker gene. For example, when the marker gene is a gene which impart the host cell with a resistance to a lethally active screening drug, then the cell into which the inventive vector has been introduced is cultured in a medium supplemented with said drug. The combination of such a drug resistance imparting gene and a screening drug may for example be the combination of a neomycin resistance imparting gene with neomycin, the combination of a hygromycin resistance imparting gene with hygromycin, and the combination of blasticidin S resistance imparting gene and blasticidin S. When the marker gene is a gene which compensates the auxotrophic nature of the host cell, then a minimum medium free from the relevant nutrition is used to culture the cell into which the inventive vector has been introduced.

In order to obtain an inventive transformant generated as a result of the introduction of an inventive DNA into a chromosome of a host cell, an inventive vector and a marker gene-carrying vector are made linear by a digestion with restriction enzymes, and then introduced as described above into a host cell, which is cultured usually for several weeks to screen for an intended transformant on the basis of the expression of the introduced marker gene. Alternatively, it is also possible to screen for an inventive transformant generated as a result of the introduction of an inventive DNA into a chromosome of a host cell by introducing an inventive vector comprising as a marker gene a gene providing a resistance to a screening drug describe above into a host cell as described above, subculturing this cell for several weeks in a medium supplemented with the screening drug, and then incubating a selected drug resistance clone surviving as a colony in a pure culture manner. In order to verify that the introduced inventive DNA has surely been integrated into the chromosome of the host cell, a standard genetic engineering method may be employed to prepare the genomic DNA of the cell, from which the presence of the inventive DNA is detected by a PCR using as a primer an oligonucleotide comprising a partial nucleotide sequence of the introduced inventive DNA or by a southern hybridization method using as a probe the introduced inventive DNA. Since such a transformant can be stored frozen and can be made viable upon any need of use, it allows the step for producing the transformant at every time of the experiment to be omitted, and allows the experiment to be conducted using a transformant whose characteristics and the handling condition for which are well established.

By culturing an inventive transformant obtained as described above, an inventive protein can be produced.

For example, when an inventive transformant is a microorganism, this transformant can be cultured using any culture medium containing carbon sources, nitrogen sources, organic salts and inorganic salts, as appropriate, used in an ordinary culture of an ordinary microorganism. The culture can be conducted in accordance with a usual procedure for an ordinary microorganism, such as a solid culture, liquid culture (rotary shaking culture, reciprocal shaking culture, Jar Fermenter, tank culture and the like). The culture temperature and the pH of the medium may appropriately be selected from the range enabling the growth of the microorganisms, and the culture is conducted usually at a temperature of about 15° C. to about 40° C. at a pH of about 6 to about 8. The culture time period is usually about 1 day to about 5 days, although it may vary depending on various culture conditions. When an expression vector comprising a promoter of a temperature shift type or an induction type such as an IPTG induction type, the induction time is preferably within 1 day, usually several hours.

When a transformant described above is an animal cell such as an insect cell, then the transformant can be cultured using a culture medium employed in an ordinary culture of an ordinary cell. When such a transformant was prepared using a screening drug, then the culture is conducted preferably in the presence of the relevant drug. In the case of a mammalian cell, the culture is conducted for example in a DMEM medium supplemented with FBS at the final concentration of 10% (v/v) (NISSUI and the like) at 37° C. in the presence of 5% $CO_2$ with replacing the culture medium with a fresh medium every several days. When the culture became confluent, a PBS solution supplemented with trypsin for example at a concentration of about 0.25 (w/v) is added to disperse the culture into individual cells, which are subjected to a several-fold dilution and then inoculated to new dishes where they are further cultured. Similarly in the case of an insect cell, an insect cell culture medium such as a Grace's medium containing 10% (v/v) FBS and 2% (w/v) Yeastlate is employed to conduct the culture at a temperature of 25° C. to 35° C. In this case, a cell which tends to be peeled off from a dish easily such as a Sf21 cell can be dispersed by pipetting instead of using a trypsin solution, whereby continuing the subculture. In the case of a transformant containing a vector of a virus such as a baculovirus, the culture time period is preferably shorter than the time period allowing a cytoplasm effect to be evident to cause the cell death, for example up to 72 hours after the virus infection.

An inventive protein produced by an inventive transformant can be recovered appropriately by a combination of ordinary isolation and purification methods, and a fraction containing the inventive protein can be obtained by collecting the transformant cells by a centrifugation after completion of the culture, suspending the collected cells in an ordinary buffer solution, pelletizing the cells for example using Polytron, ultrasonic treatment, Dounce homogenizer and the like, and then centrifuging the pelletized cell fluid to recover the supernatant. A further purified inventive protein can be recovered by subjecting the supernatant fraction described above to various chromatographic procedures such as ion exchange chromatography, hydrophobic interaction chromatography, gel filtration chromatography, affinity chromatography and the like. When an inventive protein or a polypeptide comprising its partial amino acid sequence is produced as a fusion protein with GST, the purification can be accomplished by an affinity chromatography using a glutathione sepharose (Amersham Pharmacia).

An inventive protein thus produced can be employed as an immune antigen for producing an antibody which recognizes an inventive protein or a polypeptide comprising its partial amino acid sequence, and can also be employed in an assay for screening for a substance which binds to the inventive protein.

Using an inventive protein produced as described above as an immune antigen, an animal such as mouse, rabbit, chicken and the like is immunized in accordance with an immunological procedure described in Frederick M. Ausubel et al., Short Protocols in Molecular Biology 3nd Edition, John Wiley & Sons, Inc, whereby producing an antibody which recognizes an inventive protein or a polypeptide comprising its partial amino acid sequence. More typically and in one example, an inventive protein as an antigen is mixed with a complete Freunds adjuvant to form an emulsion. The resultant emulsion is administered subcutaneously to a rabbit. After about 4 weeks, an antigen emulsified in an incomplete Freunds adjuvant is administered. If necessary, a similar administration is further conducted every two weeks. The blood is sampled to obtain a serum fraction, the antibody titre of which against the inventive protein is then verified. The resultant serum fraction having the antibody titre which recognizes the inventive protein or a polypeptide comprising its partial amino acid sequence is fractionated in accordance for example with an ordinary ammonium sulfate sedimentation method, whereby obtaining an IgG which recognizes the inventive protein or a polypeptide comprising its partial amino acid sequence.

Alternatively, a polypeptide comprising a partial amino acid sequence of an inventive protein is synthesized chemically and administered as an immune antigen to an animal, whereby producing an antibody which recognizes the inventive protein or a polypeptide comprising its partial amino acid sequence. As the amino acid sequence of a polypeptide employed as an immune antigen, an amino acid sequence which has as a low homology as possible with the amino acid sequences of other proteins and which has many differences from the amino acid sequence of an inventive protein possessed by an animal species to be immunized is selected for example from the amino acid sequences represented by SEQ ID NOs:1 to 3. A polypeptide having a length of 10 amino acids to 15 amino acids consisting of the selected amino acid sequence is synthesized chemically by a standard method and crosslinked for example with a carrier protein such as *Limulus plyhemus* hemocyanin using MBS and the like and then used to immunize an animal such as a rabbit as described above.

The resultant antibody which recognizes the inventive protein or a polypeptide comprising its partial amino acid sequence is then brought into contact with a test sample, and then a complex of the protein in the test sample with the antibody described above is detected by an ordinary immunological method, whereby detecting the inventive protein in the test sample. By means of such a detection procedure, the level or the distribution of an inventive protein for example in various tissues can be measured. Typically, when this antibody is employed as a diagnostic for a disease accompanied with a mental retardation or Alzheimer's disease, an application may become possible that an immune chromosome is employed to identify the presence or the stage of the disease described above.

A method for screening for a substance which binds to an inventive protein comprises (1) a step for bringing an inventive protein or polypeptide comprising a partial amino acid sequence thereof into contact with a test sample and (2) a step for selecting a substance which binds to the inventive protein or said polypeptide.

A typical method may for example be a method in which a test sample is brought into contact with a column to which an inventive protein has been bound and the substance which is bound to the column is purified, or other known methods such as a western blotting.

A test sample used in the screening may for example be a cell extract, gene library expression product, synthetic low molecular compound, synthetic peptide, naturally occurring compound and the like.

By means of such a screening method, it is possible to isolate a ligand of an inventive protein or a protein having a function for regulating the activity of an inventive protein to which it is bound (including antibodies).

The transcription regulation ability of an inventive protein can be measured for example by an assay using a DNA encoding said protein and a reporter gene. In a typical procedure, one which is produced first is a transformant formed by introducing:

i) a chimera gene being formed by connecting, to a downstream of a promoter which is capable of functioning in a host cell, a DNA encoding a fusion protein of a DNA binding region of a transcription regulatory factor which is capable of functioning in the host cell and an inventive protein or a polypeptide comprising a partial amino acid sequence thereof, and, ii) a reporter gene being formed by connecting a DNA encoding a reporter protein to a downstream of a promoter containing a DNA to which the DNA binding region described in i) can be bound and a minimum promoter which is capable of functioning in a host cell, into a host cell (hereinafter designated as a test transformant). On the other hand, a transformant as a control in the measurement is produced by introducing:

iii) a gene being formed by connecting, in the downstream of the promoter described in i), a DNA encoding the DNA binding region described in i), and, a reporter gene described in ii), into a host cell (hereinafter designated as a control transformant).

As a "DNA binding region of a transcription regulatory factor which is capable of functioning in a host cell" described in i) may for example be a DNA binding region of an yeast transcription regulatory factor GAL4, a bacteria repressor LexA and the like. A DNA encoding any of these is ligated to an inventive DNA or a DNA comprising a nucleotide sequence which is a partial nucleotide sequence of the inventive DNA and which encodes a partial amino acid sequence of an inventive protein with their reading frames being aligned, and then to the upstream of the ligated DNA a promoter capable of functioning in a host cell is operably connected, whereby obtaining a chimera gene being formed by connecting, to a downstream of a promoter which is capable of functioning in a host cell, a DNA encoding a fusion protein of a DNA binding region of a transcription regulatory factor which is capable of functioning in the host cell and an inventive protein or a polypeptide comprising a partial amino acid sequence thereof described in i). The "DNA comprising a nucleotide sequence which is a partial nucleotide sequence of the inventive DNA and which encodes a partial amino acid sequence of an inventive protein" described above may for example a DNA comprising a nucleotide sequence encoding an amino acid sequence from about amino acid No. 100 to about 800 in the amino acid sequence represented by any of SEQ ID NOs:1 to 3.

A promoter may for example be a inducible promoter such as a GAL1 promoter or a routinely expressed promoter such as an ADH promoter for example when a host cell is a budding yeast cell. When the host cell is an animal cell, then a Rous sarcoma virus (RSV) promoter and cytomegalovirus (CMV) promoter may be mentioned.

A reporter gene described in ii) may for example be a luciferase, secretor alkaline phosphatase, β-galactosidase, chloramphenicol acetyl transferase, growth factor and the like, with a reporter protein which is relatively stable in a host cell being preferred. A DNA encoding such a reporter gene is connected to a downstream of a promoter containing a DNA to which the DNA binding region described in i) can be bound and a minimum promoter which is capable of functioning in the host cell. For example, a DNA to which a DNA binding region of a GAL4 can be bound may for example be a Gal4 binding region of a GAL1 promoter, while a DNA to which a Lex A can be bound may for example be a LexA binding region. The minimum promoter which is capable of functioning in the host cell may for example be a DNA consisting of a minimum TATA box sequence derived from a gene capable of being expressed in a host cell, typically a DNA comprising a TATA box and a nucleotide sequence consisting of about 50 nucleotides near the transcription initiation point.

A "gene being formed by connecting, in the downstream of the promoter described in i), a DNA encoding the DNA binding region described in i)" in iii) described above can be obtained by binding, in a functional manner to a downstream of a "promoter which is capable of functioning in a host cell" used for producing a chimera gene described in i), a DNA encoding a "DNA binding region of a transcription regulatory factor which is capable of functioning in the host cell" used for producing a chimera gene described in i).

Each of genes described in i) to iii) is inserted for example into a vector, which is introduced in a combination described above into a host cell to obtain a transformant. As a vector containing a reporter gene described in ii), a commercially available vector such as a pFR-LUC (Stratagene) may be employed. As a host cell, a budding yeast cell or a mammalian cell such as a HeLa cell may be exemplified. When an intrinsic reporter gene capable of being utilized as a reporter gene described in ii) is possessed by the host cell, it may be utilized, and in such a case the introduction of a reporter gene can be omitted. In this context, a two hybrid can be accomplished by introducing both of a chimera gene, i.e., (a) a chimera gene encoding a fusion protein of one of a pair of the proteins capable of forming a complex consisting of two proteins in a host cell and a DNA binding region described in i), and (b) a chimera gene encoding a fusion protein of the other of the pair of the proteins capable of forming the complex consisting of the two proteins in the host cell and an inventive protein or a polypeptide comprising its partial amino acid sequence, instead of a gene described in i), into the host cell to obtain a test transformant.

A test transformant and a control transformant prepared as described above, for example after being allowed to stand for about several hours to several days, are subjected to the measurement of the reporter gene in each transformant. Typically, when a luciferase is employed as a reporter protein, a cell extract prepared from each transformant is combined with luciferrin which is a substrate for the luciferase, whereby allowing a luminescence to be emitted at an intensity in proportion with the luciferase level in the cell extract. Accordingly, by measuring this luminescence using a measuring device such as a luminometer, the luciferase level, and thus the luciferase (reporter) gene expression level, can be determined. When the expression level of the reporter gene in the test transformant is higher than the expression level of the reporter gene in the control transformant, the inventive protein or a polypeptide comprising its partial amino acid sequence encoded by the DNA introduced into said test transformant can be judged to have a transcription regulation ability (transcription activating ability in this case). On the contrary, when the expression level of the reporter gene in the test transformant is lower than the expression level of the reporter gene in the control transformant, the inventive protein or a polypeptide comprising its partial amino acid sequence encoded by the DNA introduced into said test transformant can be judged to have a transcription inhibiting ability.

For example, as evident from the Examples described later in this specification, an inventive protein or a polypeptide comprising its partial amino acid sequence has a transcription activating ability when using as a host cell a neuroblastoma such as an IMR32.

By using a test transformant described above, it is also possible to screen for a substance which alters the transcription regulation ability of an inventive protein. During a culture of the test transformant for 1 day or several days, a test substance is added into the medium to be brought into contact with said transformant, and then the expression level of a reporter gene in the presence of the test substance is measured. On the other hand, the expression level of the reporter gene under the condition involving no contact between the test transformant with the test substance is measured similarly. The expression level in the absence of the test substance and the expression level in the presence of the test substance are compared with each other, and a test substance which gives the expression level which may vary depending on the presence or absence of the test substance is selected, whereby screening for a substance which alters the transcription regulation ability of an inventive protein or a polypeptide comprising a partial amino acid sequence thereof encoded by the DNA introduced in said test transformant.

Then, a substance which alters the transcription regulation ability of an inventive protein in a cell unit (in other words, a substance which alters the transcriptional regulation by an inventive protein) may be screened for, for example, in an assay in which a test substance is brought into contact with a transformant obtained by introducing into a host cell a reporter gene obtained by ligating in a functional manner the expression regulation region of a DNA encoding the inventive protein. Thus, such a method may be a method for screening for a substance which alters the intracellular expression level of an inventive protein or a polypeptide comprising a partial amino acid sequence thereof comprising:

(1) a step for bringing a transformant being formed by introducing into a host cell a reporter gene obtained by ligating in a functional manner the expression regulation region of a DNA encoding said protein into contact with a test substance and then measuring the expression level of said reporter gene in the presence of the test substance, and, (2) a step for selecting a test substance which results in a expression level of said reporter gene, as measured in the step (1), which is different substantially from the expression level of said reporter gene in the absence of the test substance. Such a screening method is a method for screening for a substance altering the transcription regulation by an inventive protein or a polypeptide comprising its partial amino acid sequence, which method employs a so called reporter gene assay.

In this process, the concentration of a test substance to be brought into contact with said test transformant is usually about 0.1 µM to about 10 µM, preferably 1 µM to 10 µM. The time period during which said transformant and the test substance are brought into contact with each other is usually 18 hours to about 60 hours, preferably 24 hours to about 40 hours.

A transformant described above can be prepared as described below.

First, the expression regulation region of a DNA encoding an inventive protein is identified for example by a procedure involving (i) a step for determining the 5'-terminal by a standard method such as a 5'-RACE method (for example by using a 5' full Race Core Kit (Takara)), oligocapping method, S1 primer mapping and the like; (ii) a step for obtaining a 5'-upstream region for example by using a Genome Walker Kit (Clontech) and measuring the promoter activity of the upstream region, and then cut out by a standard genetic engineering method, and then the expression regulation region thus cut out is operably ligated to a reporter gene (a gene whose expression can be analyzed) such as glucuronidase (GUS), luciferase, chloramphenicol acetyltransferase (CAT), β-galactosidase and green fluorescence protein (GFP), whereby preparing a reporter gene being formed by operably ligated with the expression regulation region of a DNA encoding the inventive protein. The expression "operably ligated" means here that a gene and one or more regulatory sequences are ligated in such a manner that it allows the gene to be expressed when an appropriate exogenous signal or factor is bound to the regulatory sequences. The term "expression regulation region" means a sequence which contains a promoter element under a cell specific or tissue specific control or a promoter element sufficient for inducing a promoter-dependent gene expression induced by a exogenous signal or factor (such as a transcription activating protein) and which is also required for promoting the transcription. Such an element may be located on either the 5' region or the 3' region of the native gene. Subsequently, the reporter gene being formed by operably ligated with the expression regulation region of the DNA encoding an inventive protein is inserted by a standard genetic engineering method into a vector capable of being utilized in a cell to which said reporter gene is to be introduced, whereby producing a plasmid. Then, said plasmid is introduced into a cell. A method for such a introduction may for example be a calcium phosphate method, electroinduction, DEAE dextran method, micelle formation and the like. The calcium phosphate method may be a method described in Grimm, S. et al., Proc. Natl. Acad. Sci. USA, 93, 10923–10927, the electroinduciton and DEAE dextran method may for example be those described in Ting, A. T. et al. EMBO J., 15, 6189–6196, and the micelle formation may for example be a method described in Hawkins, C. J. et al., Proc. Natl. Acad. Sci. USA, 93, 13786–13790. When a micelle formation is employed, a commercially available reagent such as Lipofectamine (Gibco) or Fugene (Boehringer) may be utilized.

A cell which has been introduced with a plasmid described above is cultured in a medium providing a screening condition suitable to a screening marker gene for example by utilizing the screening marker gene which has previously been contained in vector, whereby screening for said transformant (a cell into which an inventive gene has transiently been introduced). It is also possible to screening further continuously to obtain said transformant which now became a stable transformant into whose chromosome said DNA has been introduced. In order to verify that the introduced DNA has been integrated into a chromosome present in the cell, the genomic DNA of said cell may be produced in accordance with a standard genetic engineering method and then the presence of said DNA in the genomic DNA may be detected and identified by means of a PCR employing a DNA comprising a partial nucleotide sequence of said DNA as a primer, or by a southern hybridization method employing a DNA comprising a partial nucleotide sequence of said DNA as a probe.

Said transformant may be prepared also from a transformed non-human animal tissue described below by an ordinary procedure.

A substance screened for by the searching procedures described above or a pharmaceutically acceptable salt may be utilized as an inventive expression regulating agent comprising it as an active ingredient which is obtained by formulating said active ingredient in a pharmaceutically acceptable carrier.

In a screening method described above, a method for "measuring the expression level of a reporter gene" may be any method in which the expression level of the reporter gene in said transformant can be measured continuously or intermittently over a certain period. The expression "selecting a substance which is different substantially" means to select a compound capable of giving an expression level in the presence of the test substance which is higher by 10% or more, preferably 30% or more, more preferably 50% or more, than that in the absence of the substance. For example, when the reporter gene is a luciferase gene, a commercially available product such as a luciferase assay reagent (Promega) may be employed.

A method for analyzing a genotype of a gene encoding an inventive protein possessed by an individual animal such as a human may for example be a method for investigating whether a nucleotide sequence encoding an inventive protein in a nucleic acid such as a genomic DNA or RNA contained in a sample obtained from a test individual contains a nucleotide sequence encoding an amino acid sequence which is different from the amino acid sequence of a standard protein.

Typically, first, a sample is obtained from a test individual such as a human, and from said sample a genomic DNA or RNA is prepared. For example, from a sample of a cellular tissue such as a hair, peripheral blood, oral cavity epithelium and the like, a genomic DNA can be prepared in accordance with a standard method described for example in M. Muramatsu, "Labomanual Genetic Engineering", Maruzen (1988) or TAKARA PCR Technical News No. 2, TAKARA SHUZO, (1991.9). For example, when the sample is a hair, 2 or 3 hairs are washed with a sterilized water and then with ethanol, cut into 2 to 3 mm pieces, which are combined with 200 µl of a BCL-Buffer [10 mM Tris-HCl (pH7.5), 5 mM $MgCl_2$, 0.32M sucrose, 1 Triton X-100] followed by a Proteinase K at the final concentration of 100 µl/ml and SDS at the final concentration of 0.5 (w/v). The mixture thus obtained is incubated at 70° C. for 1 hour, and then subjected to a phenol/chloroform extraction to obtain a genomic DNA. When the sample is a peripheral blood, the sample is treated using a DNA-Extraction kit (Stratagene) and the like to obtain a genomic DNA. When the sample is a fresh biopsy test sample, an RNA can be prepared from said sample for example by using a TRIZOL reagent (GIBCO). By using the resultant RNA as a template in the presence of the effect of a reverse transcriptase, a cDNA can be synthesized.

From a genomic DNA, cDNA and the like thus prepared, a DNA encoding an inventive protein is amplified for example by means of a PCR, if necessary.

A primer which may be employed for amplifying a DNA encoding an inventive protein from a genomic DNA by means of a PCR may for example be:

a polynucleotide consisting of 10 to 50 nucleotides capable of being annealed under a polymerase chain reaction condition with a polynucleotide consisting of the nucleotide sequence represented by SEQ ID NO:4, 5, 6 or 54 or the nucleotide sequence complementary to said nucleotide sequence, and typically, a polynucleotide consisting of 10 to 50 nucleotides comprising a partial nucleotide sequence of the nucleotide sequence represented by SEQ ID NO:4, 5, 6 or 54 or the nucleotide sequence complementary to said partial nucleotide sequence. More specifically, the polynucleotide consisting of the nucleotide sequence represented by SEQ ID NO:7 or 8 may be exemplified as a forward primer, while the polynucleotide consisting of the nucleotide sequence represented by SEQ ID NO:9 or 10 may be exemplified as a reverse primer.

In a genomic DNA, an inventive protein is encoded as being divided in 8 exons (hereinafter an exon containing the nucleotide sequence encoding the inventive protein is designated as exon 1 to 8 in this order from the 5'-upstream side). For example, the nucleotide sequence represented by SEQ ID NO:4 which encodes an inventive protein derived from a human is contained in the exons as being divided into the following 8 portions:

Nucleotide sequence of Nucleotide Nos.1 to 276: Exon 1
Nucleotide sequence of Nucleotide Nos.277 to 428: Exon 2
Nucleotide sequence of Nucleotide Nos.429 to 531: Exon 3
Nucleotide sequence of Nucleotide Nos.532 to 799: Exon 4
Nucleotide sequence of Nucleotide Nos.800 to 909: Exon 5
Nucleotide sequence of Nucleotide Nos.910 to 1045: Exon 6
Nucleotide sequence of Nucleotide Nos.1046 to 2481: Exon 7
Nucleotide sequence of Nucleotide Nos.2482 to 3252: Exon 8

Thus, a DNA containing the nucleotide sequence of an exon of a genome gene encoding an inventive protein and a part of the nucleotide sequence of the intron adjacent to said exon may be amplified from genomic DNA. A primer which can be employed for amplifying such a DNA may for example be:

a polynucleotide consisting of 10 to 50 nucleotides capable of being annealed under a polymerase chain reaction condition with a polynucleotide consisting of the nucleotide sequence represented by any of SEQ ID NOs:43 to 51 or the nucleotide sequence complementary to said nucleotide sequence, and typically, a polynucleotide consisting of 10 to 50 nucleotides comprising a partial nucleotide sequence of the nucleotide sequence represented by any of SEQ ID NOs:43 to 51 or the nucleotide sequence complementary to said partial nucleotide sequence. Such a primer can be designed for example as described below.

A forward primer for amplifying a DNA containing the exon 1 and a sequence in the non-translation region 5'-upstream thereof; designed based on the nucleotide sequence represented by SEQ ID NO:43.

e.g.) Polynucleotide consisting of the nucleotide sequence represented by SEQ ID NO:11 or 12.

A reverse primer for amplifying a DNA containing the exon 1 and an intron sequence 3'-downstream thereof; designed based on the nucleotide sequence complementary to the nucleotide sequence represented by SEQ ID NO:44.

e.g.) Polynucleotide consisting of the nucleotide sequence represented by SEQ ID NO:13 or 14.

A forward primer for amplifying a DNA containing the exon 2 and an intron sequence 5'-upstream thereof; designed based on the nucleotide sequence represented by SEQ ID NO:44.

e.g.) Polynucleotide consisting of the nucleotide sequence represented by SEQ ID NO:15 or 16.

A reverse primer for amplifying a DNA containing the exon 2 and an intron sequence 3'-downstream thereof; designed based on the nucleotide sequence complementary to the nucleotide sequence represented by SEQ ID NO:45.

e.g.) Polynucleotide consisting of the nucleotide sequence represented by SEQ ID NO:17 or 18.

A forward primer for amplifying a DNA containing the exon 3 and an intron sequence 5'-upstream thereof; designed based on the nucleotide sequence represented by SEQ ID NO:45.

e.g.) Polynucleotide consisting of the nucleotide sequence represented by SEQ ID NO:19 or 20.

A reverse primer for amplifying a DNA containing the exon 3 and an intron sequence 3'-downstream thereof; designed based on the nucleotide sequence complementary to the nucleotide sequence represented by SEQ ID NO:46.

e.g.) Polynucleotide consisting of the nucleotide sequence represented by SEQ ID NO:21 or 22.

A forward primer for amplifying a DNA containing the exon 4 and an intron sequence 5'-upstream thereof; designed based on the nucleotide sequence represented by SEQ ID NO:46.

e.g.) Polynucleotide consisting of the nucleotide sequence represented by SEQ ID NO:23 or 24.

A reverse primer for amplifying a DNA containing the exon 4 and an intron sequence 3'-downstream thereof; designed based on the nucleotide sequence complementary to the nucleotide sequence represented by SEQ ID NO:47.

e.g.) Polynucleotide consisting of the nucleotide sequence represented by SEQ ID NO:25 or 26.

A forward primer for amplifying a DNA containing the exon 5 and an intron sequence 5'-upstream thereof; designed based on the nucleotide sequence represented by SEQ ID NO:47.

e.g.) Polynucleotide consisting of the nucleotide sequence represented by SEQ ID NO:27 or 28.

A reverse primer for amplifying a DNA containing the exon 5 and an intron sequence 3'-downstream thereof; designed based on the nucleotide sequence comprementaly to the nucleotide sequence represented by SEQ ID NO:48.

e.g.) Polynucleotide consisting of the nucleotide sequence represented by SEQ ID NO:29 or 30.

A forward primer for amplifying a DNA containing the exon 6 and an intron sequence 5'-upstream thereof; designed based on the nucleotide sequence represented by SEQ ID NO:48.

e.g.) Polynucleotide consisting of the nucleotide sequence represented by SEQ ID NO:31 or 32.

A reverse primer for amplifying a DNA containing the exon 6 and an intron sequence 3'-downstream thereof;

designed based on the nucleotide sequence comprementaly to the nucleotide sequence represented by SEQ ID NO:49.

e.g.) Polynucleotide consisting of the nucleotide sequence represented by SEQ ID NO:33 or 34.

A forward primer for amplifying a DNA containing the exon 7 and an intron sequence 5'-upstream thereof; designed based on the nucleotide sequence represented by SEQ ID NO:49.

e.g.) Polynucleotide consisting of the nucleotide sequence represented by SEQ ID NO:35 or 36.

A reverse primer for amplifying a DNA containing the exon 7 and an intron sequence 3'-downstream thereof; designed based on the nucleotide sequence complementary to the nucleotide sequence represented by SEQ ID NO:50.

e.g.) Polynucleotide consisting of the nucleotide sequence represented by SEQ ID NO:37 or 38.

A forward primer for amplifying a DNA containing the exon 8 and an intron sequence 5'-upstream thereof; designed based on the nucleotide sequence represented by SEQ ID NO:50.

e.g.) Polynucleotide consisting of the nucleotide sequence represented by SEQ ID NO:39 or 40.

A reverse primer for amplifying a DNA containing the exon 8 and a sequence in the non-translation region 3'-downstream thereof; designed based on the nucleotide sequence comprementaly to the nucleotide sequence represented by SEQ ID NO:51.

e.g.) Polynucleotide consisting of the nucleotide sequence represented by SEQ ID NO:41 or 42.

A primer which may be employed for amplifying a DNA encoding an inventive protein from a cDNA by means of a PCR may for example be:

a polynucleotide consisting of 10 to 50 nucleotides capable of being annealed under a polymerase chain reaction condition with a polynucleotide consisting of the nucleotide sequence represented by any of SEQ ID NO:4 to 6 or the nucleotide sequence complementary to said nucleotide sequence, and typically, a polynucleotide consisting of 10 to 50 nucleotides comprising a partial nucleotide sequence of the nucleotide sequence represented by any of SEQ ID NO:4 to 6 or the nucleotide sequence complementary to said partial nucleotide sequence. More specifically, the polynucleotide consisting of the nucleotide sequence represented by SEQ ID NO:7 or 8 may be exemplified as a forward primer, while the polynucleotide consisting of the nucleotide sequence represented by SEQ ID NO:9 or 10 may be exemplified as a reverse primer.

Any of these polynucleotides can be prepared for example by using a commercially available automatic DNA synthesizer employing a β-cyanoethyl phosphoamidite method or thiophosphite method.

When a PCR is conducted using a polynucleotide described above as a primer, two primers, i.e., forward and reverse primers, are employed usually in combination. The PCR can be conducted in accordance with a method described for example in Saiki et al., Science, Vol. 230, p. 1350 to 1354 (1985). For example, an amplification buffer solution containing about 1.5 mM to about 3.0 mM magnesium chloride and the like, to which about 10 pmol of each of the polynucleotides employed as primers is added and to which a DNA polymerase, 4 nucleotides (dATP, dTTP, dGTP, dCTP) and about 100 ng of a genomic DNA or about 10 ng of a cDNA as a template has previously been added, is prepared. The resultant amplification buffer solution is subjected to 35 cycles, each cycle involving an incubation at 95° C. for 1 minutes followed by 68° C. for 3 minutes.

The nucleotide sequence of a DNA amplified as described above using a nucleic acid in a test sample as a template is determined, whereby determining whether the nucleotide sequence encoding an inventive protein in the nucleic acid of the test sample contains the nucleotide sequence encoding the amino acid sequence which is different from the amino acid sequence of the standard protein.

More specifically, a DNA amplified by a PCR as described above is subjected to a low melting point agarose gel electrophoresis, and recovered from the gel, and the recovered DNA is subjected for example to a direct sequence [BioTechniques, 7, 494 (1989)], whereby determining the nucleotide sequence of said DNA. The nucleotide sequence may be analyzed in accordance with a Maxam Gilbert Method (for example, described in Maxam. A. M. & W. Gilbert, Proc. Natl. Acad. Sci. USA, 74, 560, 1977 and the like) or a Sanger method (for example, described in Sanger, F. & A. R. Coulson, J. Mol. Biol., 94, 441, 1975., Sanger, F/. & Nicklen and A. R. Coulson., Proc. Natl. Acad. Sci. USA., 74, 5463, 1977 and the like). When an automatic DNA sequencer such as an ABI model 377, a relevant DNA sequence kit such as ABI BigDye terminator cycle sequencing ready reaction kit can be employed to prepare a sample for the sequencing.

Alternatively, a DNA amplified as described above using a nucleic acid in a test sample as a template is subjected to an electrophoresis to determine the mobility, and the measured mobility is examined for the difference from the mobility of a DNA encoding the relevant region of a standard protein, whereby determining whether the nucleotide sequence encoding an inventive protein in the nucleic acid of the test sample contains the nucleotide sequence encoding the amino acid sequence which is different from the amino acid sequence of the standard protein.

More specifically, for example upon amplifying a DNA by a PCR as described above, a $^{32}$P-labeled polynucleotide is employed as a primer in accordance with a standard method to conduct the PCR as described above. A DNA encoding the relevant region of a standard DNA is also amplified similarly. The amplified DNA is subjected to an electrophoresis in accordance for example with an SSCP (single strand conformation polymorphism) method described in Hum. Mutation, Vol. 2, p. 338. Typically, the amplified DNA is denatured with heating to dissociate into single-stranded DNAs, which are subjected to a non-denaturing polyacrylamide electrophoresis to separate into individual single-stranded DNAs. The buffer solution employed in this electrophoresis may for example be a Tris-phosphate (pH7.5–8.0), Tris-acetate (pH7.5–8.0), Tris-borate (pH7.5–8.3) and the like. If necessary, the buffer may contain EDTA and the like. The condition of the electrophoresis may involve a constant power of 30 W to 40 W, a running temperature of room temperature (about 20° C. to about 25° C.) or 4° C., and a running period of 1 hour to 4 hours. Subsequently, the gel after the electrophoresis is transferred onto a filter paper, with which an X-ray film is brought into a close contact, and then placed in a suitable light-protected cassette, where the radioactivity of individual radio-labeled single-stranded DNAs is exposed to the film. The film is developed, and the resultant autoradiogram is observed to compare the mobility between the DNA amplified using the nucleic acid in the test sample as a template and the DNA encoding the relevant region of the standard protein. When the mobility of these DNAs is different from each other, then the nucleotide sequence encoding the inventive protein in the nucleic acid in the test sample is judged to contain the nucleotide sequence encoding the amino acid sequence which is different from the amino acid sequence of the standard protein. Furthermore, the gel containing the DNA having a different mobility is extracted with a boiling water to recover the DNA contained therein, which is employed as a template to perform a PCR, whereby amplifying said DNA, which is subjected to a low melting point agarose gel electrophoresis, and recovered from the gel, and then subjected to a direct sequence, whereby determining the nucleotide sequence of said DNA. In this manner, the nucleotide sequence encoding the amino acid sequence which is different from the amino acid sequence of the standard protein can be identified.

By investigating the pattern of the hybridization between a nucleic acid such as a genomic DNA, cDNA or mRNA in a test sample or a DNA amplified using as a template a nucleic acid in a test sample as described above and a polynucleotide consisting of 10 to 5000 nucleotides capable of hybridizing under a stringent condition with a polynucleotide consisting of the nucleotide sequence represented by SEQ ID NO:4, 5, 6 or 54 or the nucleotide sequence complementary to said nucleotide sequence, it can be determined whether the nucleotide sequence encoding an inventive protein in the nucleic acid of the test sample contains the nucleotide sequence encoding the amino acid sequence which is different from the amino acid sequence of a standard protein.

A "polynucleotide consisting of 10 to 5000 nucleotides capable of hybridizing under a stringent condition with a polynucleotide consisting of the nucleotide sequence represented by SEQ ID NO:4, 5, 6 or 54 or the nucleotide sequence complementary to said nucleotide sequence" may for example be a polynucleotide consisting of 10 to 5000 nucleotides comprising a partial nucleotide sequence of the nucleotide sequence represented by SEQ ID NO:4, 5, 6 or 54 or the nucleotide sequence complementary to said partial nucleotide sequence.

A nucleic acid such as a genomic DNA, cDNA or mRNA prepared from a test sample or a DNA amplified using as a template a nucleic acid in a test sample as described above is mixed with a polynucleotide described above and subjected to a hybridization under a stringent condition. The hybridization can be accomplished in accordance with a standard dot blot hybridization, southern blot hybridization or northern blot hybridization described for example in J. Sambrook, E. F. Frisch, T. Maniatis, Molecular Cloning, 2nd Edition, Cold Spring Harbor Laboratory (1989) or by a mismatch detection method utilizing a Taq MutS which is an enzyme capable of binding to a mismatch hybridization site [described for example in Biswas, I. And Hsieh, P. J. Biol. Chem., 271, 9, pp. 5040–5048 (1996) or Nippon Gene information 1999, No. 125, Nippon Gene, TOYAMA].

A stringent condition in the hybridization may involve, for example, a prehybridization and a hybridization conducted in the presence of 6×SSC (0.9M sodium chloride, 0.09M sodium citrate), 5× Denhart's solution (0.1 (w/v) ficoll 400, 0.1 (w/v) polyvinyl pyrrolidone), 0.1 SA), 0.5 (w/v) SDS and 100 µg/ml denatured salmon sperm DNA, or in a DIG ESY Hyb solution (Boehringer Mannheim) containing 100 µg/ml denatured salmon sperm DNA, followed by an incubation, as a washing process, at room temperature for 15 minutes in the presence of 1×SSC (0.15M sodium chloride, 0.015M sodium citrate) and 0.5 DS, followed by an incubation for 30 minutes in the presence of 0.1×SSC (0.015M sodium chloride, 0.0015M sodium citrate) and 0.5 DS. The incubation temperature in the prehybridization, hybridization and washing process may vary depending on the length and the composition of the polynucleotide employed as a probe, and is generally identical to the Tm of the probe or a temperature higher slightly than the Tm. Typically, in the case for example of a base pair when a inter-base hydrogen bond is formed between the probe and the nucleic acid in the sample in the hybridization, Tm is the sum of the all values of the base pairs forming hydrogen bonds with one pair of A and T being assigned to 2° C. and one pair of G and C being assigned to 4° C. A temperature identical to the Tm value thus calculated or a temperature which is higher by 2 to 3° C. may be selected.

In a typical procedure of a dot hybridization, a nucleic acid such as a genomic DNA, cDNA and the like prepared from a test sample or a DNA amplified using as a template a nucleic acid in a test sample as described above is incubated at 90° C. to 100° C. for 3 to 5 minutes, and then spotted onto a nylon filter [Hybond N (Amersham Pharmacia) and the like], and then the spotted filter is dried on a filter paper, and then irradiated with a UV light, whereby immobilizing the DNA on the filter. Then, the resultant DNA-immobilizing filter and the probe described above are incubated for example at 40° C. to 50° C. for 10 hours and 20 hours to effect a hybridization, and the hybrid containing the probe is detected in accordance with a standard method. When the probe employed is a radioactive probe labeled with a radioactive isotope such as $^{32}p$, the filter after the hybridization is exposed to an X-ray film whereby detecting a hybrid containing the probe. When the probe employed is a non-radioactive probe labeled with a biotinylated nucleotide, a hybrid containing said probe is labeled with an enzyme such as a biotinylated alkaline phosphatase via streptoavidine, and the color development or luminescence of the substrate due to the enzyme reaction is detected, whereby detecting a hybrid containing the probe. It is also possible to use a non-radioactive probe which is labeled directly via a spacer with an enzyme such as an alkaline phosphatase or peroxidase. When the DNA from the test sample gave no detectable hybrid containing the probe or when the DNA from the test sample gave a level of the hybrid which is higher than that of the level of the hybrid given by a DNA encoding the relevant region of a standard protein, then it can be judged that the nucleic acid in the test sample contains a nucleotide sequence different from the nucleotide sequence of the probe employed.

The procedure of a southern blot hybridization or northern blot hybridization may involve digesting a nucleic acid such as a genomic DNA, cDNA or mRNA prepared from a test sample or a DNA amplified using as a template a nucleic acid in a test sample as described above with a restriction enzyme if necessary, followed by an electrophoresis such as an agarose gel electrophoresis or polyacrylamide gel electrophoresis to effect a fractionation, followed by blotting onto a filter such as a nitrocellulose filter or nylon filter. The resultant filter is treated as described above and then hybridized with a probe. When the level of the hybrid containing the probe or the length of the nucleic acid forming a hybrid with the probe is different between the nucleic acid from the test sample and the relevant nucleic acid of a standard protein, then the nucleotide sequence encoding the inventive protein in the nucleic acid in the test sample is judged to contain the nucleotide sequence encoding the amino acid sequence which is different from the amino acid sequence of the standard protein.

When using a mismatch detection method utilizing a Taq MutS which is an enzyme capable of binding to a mismatch hybridization site, the binding characteristics of the Taq Muts, such as a high stability to a heat (0 to 75° C.) and an ability of maintaining the activity even at a high temperature to recognize the DNA mismatch base pair whereby enabling the binding, are utilized to detect the mismatch base pair by conducting a gel shift assay using a non-denatured polyacrylamide gel or a dot blotting method on a solid phase such as a nylon filter or nitrocellulose filter. When a mismatch is detected, then it can be judged that the nucleic acid in the test sample contains a nucleotide sequence different from the nucleotide sequence of the probe employed.

A standard protein can be selected from inventive proteins as appropriate, and may for example be an inventive protein consisting of the amino acid sequence represented by SEQ ID NO:1, 2 or 3.

An inventive kit can be applied to a method for investigating the presence of a gene, the genotype, the protein type and the like utilizing a known method such as a hybridization (for example, dot blot hybridization, Southern blot hybridization, Northern blot hybridization, mismatch detection utilizing a Taq MutS), an SSCP method (method utilizing the mobility of a DNA), a PCR method (for example, genomic PCR, cDNA PCR and the like) as described above. In such a case, an inventive kit may contain a reagent required for a known method described above, or may be used in combination with such a reagent.

An analysis of the genotype of a gene encoding an inventive protein possessed by an individual animal such as a human, which can be conducted as described above, is useful in the diagnosis, prophylaxis and therapy of a disease induced by the variation in the inventive protein.

Furthermore, since a gene encoding an inventive protein is a gene which is mapped between STS markers D11S913 and D11S1889 positioned in 11q13 on a human chromosome, more specifically, a gene which is present at a position whose distance from D11S913 is about 175 kbp in the direction of the telomere, it can be expected to be utilized as a tightly linked gene marker with regard to Bardet-Biedl syndrome Type I, and thus can be applied to the diagnosis of such a disease based on the methods described above.

The invention also provides a method for promoting the expression of a drebrin 1 in a mammal comprising a step for providing the mammalian cell with the DNA encoding an inventive protein in a position enabling the expression of said DNA in said cell [inventive promoting method].

Such a mammalian cell may for example be a cell derived from a mammal such as human, monkey, mouse, rat, hamster and the like. Such a cell may be a cell which constitutes a population having identical functions and morphologies, or a cell present in the body of said mammalian animal.

Accordingly, when the mammalian animal is a human, a range from a human receiving a so called gene therapy to a cell line employed in various experiments is contemplated, while when the mammalian animal is a non-human animal then a range from a non-human animal receiving a so called gene therapy to an animal model or a cell line employed in various experiments is contemplated. In the latter case, a preferred species is rat, mouse and the like.

Moreover, a case in which a mammalian cell is a cell in the body of a mammalian animal which can be diagnosed to suffer from a disease accompanied with a mental retardation or from Alzheimer's disease can be exemplified as a more typical case.

A method for preparing a DNA encoding an inventive protein may be prepared in accordance with a method equivalent to that described above.

Using such a DNA thus prepared, a transformant is prepared as described below, whereby obtaining a transformant in which said DNA is provided in a position which enables its expression in the mammalian cell.

In an inventive expression promoting method, the phrase "provided in a position enabling the expression" means that a DNA molecule is placed in the position adjacent to a DNA sequence directing the transcription and the translation of its nucleotide sequence (i.e., promoting the production of an inventive protein or its RNA molecule).

The expression level of the DNA of an inventive protein may be any level which is sufficient to promote the expression of a drebrin 1 when compared with a cell into which no DNA of the inventive protein has been introduced. In such a case, the DNA encoding the inventive protein may be a DNA encoding the entire or a part of the inventive protein.

In an expression promoting method described above, it is also possible to promote a drebrin 1 by preparing a transformant in which a DNA encoding an inventive protein is integrated into a genome.

In an expression promoting method described above, a gene construct employed for introducing a DNA encoding an inventive protein into a mammalian cell (hereinafter sometimes referred to as an inventive gene construct) and a method for accomplishing a gene import may employ a virus vector having an affinity to the mammalian cell to which said DNA is to be introduced, such as a retrovirus vector, adenovirus vector, adeno-associated virus vector or others. For example, known vectors described in Miller, Human Gene Therapy 15 to 14, 1990; Friedman, Science 244:1275 to 1281, 1989; Eglitis and Anderson, BioTechniques 6:608 to 614, 1988; Tolstoshev and Anderson, Current opinion in Biotechnology 1;55 to 61, 1990; Sharp, The Lancet 337: 1277 to 1278, 1991; Cornetta et al, Nucleic Acid Research and Molecular Biology 36:311 to 322, 1987; Anderson, Science 22-:401 to 409, 1984; Moen, Blood Cells 17:407 to 416, 1991; Miller et al., Biotechniques 7:980 to 990, 1989; Le Gai La Salle et al., Science 259:988 to 990, 1993; and Johnson) Chest 107:77S to 83S, 1995 and the like may be exemplified. The retroviruses described for example in Rosenberg et al, N. Engl. J. Med 323:370, 1990; Anderson et al., U.S. Pat. No. 5,399,346 have extensively developed, and have already been introduced into a clinical stage. For example, when said cell is an animal cell, those which may be exemplified are an SV40 virus promoter, cytomegalovirus promoter (CMV promoter), Rous sarcoma virus promoter (RSV promoter, β actin gene promoter, aP2 gene promoter and the like. It is also possible to use a commercially available vector containing any of these promoters upstream of the multiple cloning site.

Said DNA may be placed under the control of a promoter which allows a DNA of an inventive protein to be expressed constitutively. Such a DNA may also be placed under the control of a promoter which regulates the expression of a DNA of an inventive protein via an environmental stimulation. For example, said DNA may be expressed using a tissue-specific or cell type-specific promoter or a promoter which is activated by a chemical signal or exogenous signal such as a drug or by the introduction of a drug.

It is also possible to employ an non-viral technique. Those which may be exemplified are a lipofection described in Felgner et al., Proc. Natl. Acad. Sci. USA 84:7413, 1987; Ono et al., Neurosci. Lett. 117:259, 1990; Brigham et al., Am. J. Med. Sci. 298:278, 1989; Staubinger et al., Meth. Enz. 101:512, 1983, asialoorosomucoid-polylysine conjugation (Wu et al., J. Biol. Chem. 263:14621, 1988, lipofection described in Wu et al., J. Biol. Chem. 264:16985, 1989 and the like, microinjection described in Wolff et al., Science 247:1465, 1990 and the like, calcium phosphate method, DEAE dextran method, electroporation, protoplast fusion method, liposome method and the like.

While in any of the technologies described above an inventive gene construct is applied (for example by an infusion) to the site where an underexpression of a drebrin 1 is expected, it may be applied to a tissue near the site where an event such as an underexpression of a drebrin 1 is expected or to a vessel supplying to the cell assumed to undergo an underexpression of a drebrin 1.

In an inventive gene construct, the expression of a DNA (cDNA) of an inventive protein can be directed by an appropriate promoter (for example, a promoter of human cytomegalovirus (CMV), simian virus 40 (SV40) or metallothionein and the like), and may also be regulated by an appropriate mammalian animal regulatory factor. For example, a DNA of an inventive protein can be expressed if necessary using an enhancer known to direct predominantly to the expression of the DNA in a neurocyte. Such an enhancer may be any enhancer whose expression is characterized to be specific to a tissue or cell. When a clone of a DNA (genome) of an inventive protein is employed as a gene construct (for example, a clone of a DNA (genome) of an inventive protein isolated by the hybridization with a DNA (cDNA) of an inventive protein described above), the regulation can be accomplished also via a cognate regulatory sequence, if necessary together with a regulatory sequence derived from an heterologous source containing any promoter or regulatory element described above.

When an expression promoting method described above is applied as a method for a gene therapy, it can be used by a direct administration of the gene of an inventive protein into a cell. While the gene which may be employed may be any gene which has been produced or isolated by a standard method, a most convenient production can be accomplished by an in vivo transcription employing the gene of an inventive protein under the control of a highly efficient promoter (for example, human cytomegalovirus promoter). The administration of the gene of an inventive protein can be conducted by any of the direct nucleic acid administration methods described above.

An expression promoting method described above can be applied also as a gene therapy method in which a normal gene is implanted into a diseased cell of a patient. In this method, the normal inventive protein gene is transfected into the cell which is exogenous or endogenous to the patient and which can be cultured. Then, the transfected cell is infused serologically into a target tissue.

Ideally, the production of an inventive protein by all technologies for the gene therapy gives an intracellular level of the inventive protein which is at least equal to a normal intracellular level of the inventive protein in a non-diseased cell.

As an example, an inventive expression promoting method in the case where the mammalian animal is a transformed mouse is detailed below.

A method for introducing a DNA encoding an inventive protein in the production of a transformed mouse may for example be a microinjection method, a method employing a retrovirus, a method employing an embryonic stem cell (ES cell) and the like. Among those listed above, the microinjection method is employed most frequently. The microinjection method employs a micromanipulator to infuse a solution containing the relevant DNA into the pronucleus of a fertilized ovum under the observation by a microscope.

First, a DNA encoding an inventive protein is infused into a fertilized ovum. In this step, it is preferably to remove the vector region employed for isolating this DNA as much as possible, to remove an AU-rich region contributing to the instabilization of a mRNA and to make the DNA linear for the purpose of integrating the DNA into a chromosome at a high probability. It is also preferable to insert an intron previously into the DNA, and such an intron may for example be a β-globin intron and the like.

A fertilized ovum is obtained from a mouse of a line suitable for the purpose. An inbred C57BL/6 mouse or C3H mouse, a cross line of the C57BL/6 mouse with another line (such as (C57BL/6×DBA/2) F1), a non-inbred line ICR mouse may be exemplified. The fertilized ovum is obtained by mating a female mouse whose superovulation is induced by intraperitoneal administration of both of a pregnant mare's serum gonadotropin and chorionic gonadotropin with a male mouse followed by isolating the ovum from this female mouse. The isolated fertilized ovum is placed in a culture drop, which is maintained in a $CO_2$ gas incubator, whereby enabling the storage until the infusion of the relevant DNA.

The infusion of the DNA is conducted under the observation with an inverted microscope fitted with a micromanipulator. A fertilized ovum employed is preferably one in a developmental stage of the time when the male pronucleus becomes larger than the female pronucleus through the time when the both pronuclei are fused with each other. First, the fertilized ovum is fixed, and a DNA solution containing the relevant DNA is infused into the male pronucleus of the fertilized ovum. This DNA solution can be prepared as a complex if necessary. A substance used for forming a complex may for example be a liposome, calcium phosphate, retrovirus and the like. The infusion of the DNA solution is evident from the swelling of the male pronucleus. The amount of the DNA infused may for example be an amount containing about 200 to about 3,000 copies of the relevant DNA.

A fertilized ovum into which a DNA encoding an inventive protein has been infused is then cultured as described above until it becomes a blastocyst, which is then implanted into the uterus of a surrogate mother. Preferably, the ovum is implanted into the oviduct of the surrogate mother immediately after the infusion of the DNA. The surrogate mother is preferably a female mouse in a pseudo-pregnant female mouse after mating with a male mouse whose seminal duct has been ligated. Typically, the relevant female mouse is excised at the back skin and muscle near the kidneys to take the ovaries, oviducts and uterus out, and the ovarian membrane is opened to search for the oviduct opening. Then a surviving fertilized ovum after infusing the relevant DNA is imported from the oviduct opening, and then the ovaries, oviducts and uterus are returned into the abdominal cavity, and then the muscle coats are sutured and the skin is clipped. After about 20 days, a neonate is born.

A part of the somatic tissue of the neonate thus obtained, such as a part of the tail, is cut out as a sample, from which DNAs are extracted and subjected for example to a southern blotting, whereby identifying the relevant DNA. As described above, it can be verified that the relevant DNA has been introduced into a non-human animal. Otherwise, a PCR may also be employed for identification.

While a DNA encoding an inventive protein as an active ingredient of an inventive gene therapy agent may be prepared as described above, it can be employed in the form of a recombinant vector or recombinant virus containing the relevant DNA. Such a form may for example be a virus vector such as a retrovirus vector, adenovirus vector, adeno-associated virus vector, herpes simplex virus vector, SV40 vector, polyoma virus vector, papilloma virus vector, picornavirus vector and vaccinia virus vector and the like. When an adenovirus vector is employed, an AdEasy Kit produced by QUANTUM is employed to integrate an inventive DNA into a multiple cloning site of a Transfer Vector, and the resultant recombinant vector is made linear, and then transformed into a coliform microorganism together with a pAdEasy vector, and a homologous recombinant DNA is integrated into a human 293A cell, whereby producing a recombinant virus containing the inventive DNA, which is then recovered and used.

It is also possible to use a non-viral vector such as a plasmid DNA comprising a human cytomegalovirus promoter region. Similarly to a case where an inventive DNA is infused directly into a fibrotic tissue site, a use of a plasmid DNA is extremely beneficial in a system where the inventive DNA is delivered locally using a non-viral vector. By employing a method in which a cell once taken out of a body is introduced with an expression vector and then returned to the body, i.e., an ex vivo method, all of the known introduction methods can be utilized. For example, a non-viral vector can be introduced by means of a) direct infusion, b) liposome-mediated introduction, c) cell transfection by calcium phosphate method, electroporation and DEAE-dextran method, d) polybrene-mediated delivery, e) protoplast fusion, f) microinjection, g) introduction using polylysine and the like.

An inventive gene therapy agent can be given at an effective dose parenterally to a mammalian animal such as a human. For example, a parenteral administration can be accomplished for example by an injection (subcutaneous, intravenosu) as described above. A suitable dosage form described above can be produced by incorporating an inventive DNA (including vector form, virus form, plasmid form of the inventive DNA) into a pharmaceutically acceptable carrier such as an aqueous solvent, non-aqueous solvent, buffering agent, solubilizing aid, osmotic agent, stabilizer and the like. If necessary, auxiliary agents such as a preservative, suspending agent, emulsifier and the like may also be added.

While the dose may vary depending on the age, sex, body weight of a mammalian animal to be treated, the type of an inventive fat accumulation inhibitor, and the dosage form, it is usually an amount of an active ingredient which gives an intracellular level of an inventive protein which is equal to a level allowing the inventive protein to act effectively in the cell of the patient. The daily dose described above may be given all at once or in portions.

Furthermore, the present invention provides a nucleic acid consisting of the entire of or a part of the antisense chain of a DNA encoding an inventive protein or an RNA corresponding thereto. For example, a pathological section is subjected to an in situ hybridization of the DNA encoding the inventive protein, whereby detecting the presence or the stage of a disease.

When an inventive nucleic acid is employed as a diagnostic probe, it may not particularly be limited as long as it has a length of 20 nucleotides or more. For employing such a probe as an active ingredient of a diagnostic agent, the probe is dissolved preferably in a suitable buffer solution or sterilized water in which it is not decomposed. An in situ hybridization may be conducted for example by a method described in J. Neurobiol. 29, 1–17 (1996). It is also possible to employ a PCR method.

EXAMPLES

The present invention is further described in the following Examples, which are not intended to restrict the invention.

Example 1

Acquisition of Inventive DNA and Production of Inventive Vector

Each polynucleotide consisting of the nucleotide sequence represented by any one of SEQ ID NOs: 7 to 10 was synthesized using a DNA synthesizer (Applied Biosystems, Model 394). As a template, 10 ng of a human fetal brain cDNA library (#10662-013 Gibco BRL), a mouse brain cDNA library (#10655-017, Gibco BRL) or a rat brain cDNA library (#9539, Takara) was employed, and each template was combined as shown in Table 1 with the polynucleotide described above as a primer, and subjected to the PCR.

TABLE 1

| Combination | Forward primer | Reverse primer |
| --- | --- | --- |
| 1 | SEQ ID NO: 7 | SEQ ID NO: 9 |
| 2 | SEQ ID NO: 8 | SEQ ID NO: 10 |
| 3 | SEQ ID NO: 7 | SEQ ID NO: 10 |
| 4 | SEQ ID NO: 8 | SEQ ID NO: 9 |

In this PCR, each 10 pmol of the polynucleotide described above was added to 50 μl of the reaction solution, and an LA-Taq polymerase (Takara) and a buffer attached to this enzyme were employed. The reaction solution was incubated using a PCR system 9700 (Applied Biosystems) and subjected to 35 cycles, each cycle consisting of an incubation for 1 minutes at 95° C. followed by 3 minutes at 68° C. Then, the entire volume of the reaction solution was subjected to an agarose gel electrophoresis using a low melting point agarose (agarose L, Nippon Gene). After identifying a single band of an about 2.5 kb DNA, this DNA was recovered. A part of the DNA recovered was used together with a dye terminator sequence kit FS (Applied Biosystems) to prepare a direct sequencing sample, which was subjected to a direct nucleotide sequencing using an autosequencer (Applied Biosystems, Model 3700). The DNA obtained using the human cDNA as a template had the nucleotide sequence represented by SEQ ID NO:4, and this nucleotide sequence encoded the amino acid sequence represented by SEQ ID NO:1. The DNA obtained using the mouse cDNA as a template had the nucleotide sequence represented by SEQ ID NO:5, and this nucleotide sequence encoded the amino acid sequence represented by SEQ ID NO:2. The DNA obtained using the rat cDNA as a template had the nucleotide sequence represented by SEQ ID NO:6, and this nucleotide sequence encoded the amino acid sequence represented by SEQ ID NO:3.

Subsequently, about 1 μg of the about 2.5 kb DNA which was recovered as described above and whose nucleotide sequence was identified was mixed with 10 ng of a pGEM T easy vector (Promega), and combined with a T4 DNA ligase to effect a reaction. The resultant reaction solution was employed to transform an *E. coli* DH5a competent cell (TOYOBO), and a plasmid DNA was prepared from an ampicillin resistant colony, and its nucleotide sequence was determined using an ABI Model 3700 autosequencer by a dye terminator method. The determined nucleotide sequence was compared with the nucleotide sequence obtained by the direct sequencing described above, and a plasmid whose nucleotide sequence in the translation region exhibited a complete agreement was selected. A plasmid containing a DNA encoding the amino acid represented by SEQ ID NO:1 was designated as pGEM-hNXF, a plasmid containing a DNA encoding the amino acid represented by SEQ ID NO:2 as pGEM-mNXF and a plasmid containing a DNA encoding the amino acid represented by SEQ ID NO:3 as pGEM-rNXF.

The amino acid sequence represented by SEQ ID NO:1, 2 or 3 was compared with each other using a GenetyxSV/R ver.4 program (SOFTWARE KAIHATSU). As a result, the amino acid homology between the amino acid sequence represented by SEQ ID NO:1 and the amino acid sequence represented by SEQ ID NO:2 was 93%, and the amino acid homology between the amino acid sequence represented by SEQ ID NO:2 and the amino acid sequence represented by SEQ ID NO:3 was 98%.

The amino acid sequence represented by SEQ ID NO:1, 2 or 3 was subjected to a motif search by utilizing the database service by GenomNet referring to each of the motif dictionaries including PROSITE (Nucl. Acids. Res, 1997; 24:217–221, Bairoch, A. et al.), BLOCKS (Nucl. Acids. Res, 1991; 19:6565–6572, Henikoff, S. et al.), ProDom (Protein Sci, 1994; 3:482–492, Sonnhammer, E. L. et al.) and PRINTS (Protein Eng, 1994; 7:841–848, Attwood, T. K. et al.). As a result, any of the amino acid sequences had a bHLH motif in a region around the amino acid Nos.1 to 24 and a PAS domain in a region around the amino acid Nos.25 to 310.

Example 2

Amplification of cDNA Encoding Inventive Protein by PCR

A cDNA prepared from a mRNA extracted from a pooled reticulum of 76 humans (#7124-1, Clontech) was employed as a template to perform a PCR using the polynucleotide oligonucleotide comprising the nucleotide sequence represented by SEQ ID NO:52 and the polynucleotide oligonucleotide comprising the nucleotide sequence represented by SEQ ID NO:53 as primers. Each 10 pmol of the polynucleotide described above was added to 50 µl of the reaction solution, and an LA-Taq polymerase (Takara) and a buffer attached to this enzyme were employed. The reaction solution was incubated using a PCR system 9700 (Applied Biosystems) and subjected to 35 cycles, each cycle consisting of an incubation for 1 minutes at 95° C. followed by 3 minutes at 68° C. Then, the entire volume of the reaction solution was subjected to an agarose gel electrophoresis using an agarose (agarose S, Nippon Gene). A single band of the DNA was observed at about 2.5 kb. It was thus verified that the mRNA encoding the inventive protein was expressed in the human reticulum.

Example 3

Detection of Nucleic Acid Encoding Inventive Protein by Hybridization

The plasmid pGEM-hNXF prepared in EXAMPLE 1 was digested with BamHI and NotI, and the digestion product was subjected to an agarose gel electrophoresis using a low melting point agarose (agarose L, Nippon Gene) to recover an about 1.0 kbp DNA and an about 2.3 kbp DNA. 50 ng of each DNA thus recovered was $^{32}$P-labeled using a labeling kit by a random primer method (Rediprime II: Amersham Pharmacia) and $\alpha^{32}$P-dCTP (Amersham Pharmacia).

Using the about 1.0 kbp labeled DNA as a probe, a hybridization was performed with nylon filters blotted with mRNAs of various human tissues [Human 12-Lane MTN Blot (#7780-1, Clontech) and Human MTN Blot IV (#7766-1 Clontech)]. On the other hand, the about 2.3 kbp labeled DNA was used as a probe to perform a hybridization with nylon filters blotted with mRNAs of human tissues such as a brain [Human Brain MTN Blot II (#7755-1, Clontech) and Human Brain MTN Blot IV (#7769-1 Clontech)].

The hybridization conditions were in accordance with the manufacturer's instruction of the nylon filters described above. Thus, the nylon filter was incubated in 5 ml of an ExpressHyb solution (Clontech) at 68° C. for 30 minutes, and 50 ng of each labeled probe described above was added and the incubation was continued for 1 hour at 68° C. Then the filter was subjected twice to the incubation at 65° C. for 30 minutes in about 200 ml of 2×SSC containing 0.05 DS, and then further subjected twice to the incubation at 65° C. for 30 minutes in 0.1×SSC containing 0.1% SDS. Subsequently, the nylon filter was brought into a close contact with an imaging plate (FUJI FILM) and allowed to stand for 1 weeks, and then subjected to an imaging analyzer (BASstation: FUJI FILM) to detect the sensitized image on the plate. The investigated human tissues are as shown below.

Brain, Heart, Skeletal muscle, Colon (no mucosa), Thymus, Spleen, Kidney, Liver, Small intestine, Placenta, Lung, Peripheral blood leukocyte, Prostate, Testis, Uterus (no endometrium), Cerebellum, Cerebral cortex, Medulla, Spinal cord, Occipital pole, Frontal lobe, Temporal lobe, Putamen, Amygdala, Caudate nucleus, Corpus callosum, Hippocampus, Substantia nigra, Thalamus.

As a result, the nylon filters blotted with the mRNAs of various human tissues exhibited an intense signal at the brain, low signals at the skeletal muscle and kidney, and no signals at other tissues. On the other hand, the nylon filters blotted with mRNAs of human tissues such as a brain exhibited signals at all brain tissues, medulla and spinal cord blotted on the filters.

Example 4

Genotype Analysis of Gene Encoding Inventive Protein 0.1 gram of a frozen human brain sample is combined with 1 ml of a Trizole reagent (Gibco BRL) and homogenized. The resultant homogenate is combined with 0.2 m 1 of chloroform, stirred, centrifuged at 4° C. and 12000×g for 15 minutes, and the organic layer and the aqueous layer are transferred into separate tubes. The aqueous layer is combined with 0.5 ml of isopropanol, mixed, allowed to stand at room temperature for 5 minutes, centrifuged at 4° C. and 12000×g for 10 minutes, and the precipitated RNA is recovered. The recovered precipitate is rinsed with 70% ethanol, air-dried, dissolved in water, and used as a human RNA sample.

Using 1 µg of the human brain RNA thus prepared as a template and 1 µg of oligo dT primer (Amersham Pharmacia) as a primer, an incubation is conducted at 37° C. for 1 hour in the presence of Superscript II (Gibco) and a buffer attached to this enzyme. A ¹⁄₅₀ volume of the resultant human brain cDNA solution is employed as a template to perform a PCR similarly to EXAMPLE 1 using the polynucleotide consisting of the nucleotide sequence represented by SEQ ID NO:7 and the polynucleotide consisting of the nucleotide sequence represented by SEQ ID NO:9 as primers, whereby amplifying the DNA. The resultant DNA is subjected to an agarose gel electrophoresis using a 1% low melting point agarose (agarose L, Nippon Gene) and recovered. The entire amount of the recovered DNA is used as a template to prepare a sample for a direct sequencing by a dye terminator sequence kit FS (Applied Biosystems). Then the sample is subjected to a nucleotide sequencing using an autosequencer (Applied Biosystems, Model 3700) to determine the nucleotide sequence.

On the other hand, 0.1 g of a human liver frozen sample was combined with the Trizole reagent and the organic layer was isolated as described above. The resultant organic layer was combined with 0.3 ml of ethanol, centrifuged at 4° C. and 2000×g for 5 minutes to recover the precipitate. This precipitate was rinsed with a mixture of 0.1M sodium citrate and 10% ethanol, air-dried, dissolved in TE, whereby obtaining a human genomic DNA sample. This human genomic DNA was employed as a template to perform a PCR, whereby amplifying the nucleotide sequence of the exon of the genome gene encoding an inventive protein and the DNA containing a part of the nucleotide sequence of the intron adjacent to this exon. As a primer, the polynucleotide consisting of the nucleotide sequence represented by any of the SEQ ID NOs:11 to 42 was prepared by DNA synthesizer (Applied Biosystems, Model 394), and employed in the combinations shown in Table 2.

TABLE 2

| Sample No. | Forward primer | Reverse primer |
| --- | --- | --- |
| 1 | SEQ ID NO: 11 | SEQ ID NO: 13 |
| 2 | SEQ ID NO: 12 | SEQ ID NO: 14 |
| 3 | SEQ ID NO: 15 | SEQ ID NO: 17 |
| 4 | SEQ ID NO: 16 | SEQ ID NO: 18 |
| 5 | SEQ ID NO: 19 | SEQ ID NO: 21 |
| 6 | SEQ ID NO: 20 | SEQ ID NO: 22 |
| 7 | SEQ ID NO: 23 | SEQ ID NO: 25 |
| 8 | SEQ ID NO: 24 | SEQ ID NO: 26 |
| 9 | SEQ ID NO: 27 | SEQ ID NO: 29 |
| 10 | SEQ ID NO: 28 | SEQ ID NO: 30 |
| 11 | SEQ ID NO: 31 | SEQ ID NO: 33 |
| 12 | SEQ ID NO: 32 | SEQ ID NO: 34 |
| 13 | SEQ ID NO: 35 | SEQ ID NO: 37 |
| 14 | SEQ ID NO: 36 | SEQ ID NO: 38 |
| 15 | SEQ ID NO: 39 | SEQ ID NO: 41 |
| 16 | SEQ ID NO: 40 | SEQ ID NO: 42 |

The PCR was conducted using a LA-Taq DNA polymerase (Takara) in a buffer attached specially with the enzyme described above in the presence of 100 μM of each of the 4 nucleotides (dATP, dTTP, dGTP, dCTP), which was subjected to 35 cycles, each cycle involving an incubation at 95° C. for 1 minutes followed by 68° C. for 1 minute. A part of each resultant reaction solution was subjected to an agarose gel electrophoresis. Any of the sample Nos. 1 to 16, a single DNA band was detected on the agarose gel.

The remaining PCR reaction solution is run on a 1% low melting point agarose (agarose L, Nippon Gene) and the DNA detected as a band is recovered. The recovered DNA is used as a template to prepare a sample for a direct sequencing by a dye terminator sequence kit FS (Applied Biosystems). Then the sample is subjected to a nucleotide sequencing using an autosequencer (Applied Biosystems, Model 3700) to determine the nucleotide sequence.

2 or 3 hairs are washed with a sterilized water and then with 100% ethanol, dried at room temperature, cut into 2 to 3 mm pieces, which are transferred to a plastic tube. To this, 200 μl of a BCL-Buffer [10 mM Tris-HCl (pH7.5), 5 mM MgCl$_2$, 0.32 sucrose, 1 Triton X-100] is added, followed by a Proteinase K at the final concentration of 100 μl/ml and SDS at the final concentration of 0.5 (w/v). The mixture thus obtained is incubated at 70° C. for 1 hour, combined with an equal volume of phenol/chloroform, shaken vigorously, and centrifuged (15000 rpm, 5 minutes, 4° C.). The aqueous layer is recovered by pipetting carefully to avoid any disturbance to the phenol layer, and then extracted again with phenol. The recovered aqueous layer is combined with an equal volume of chloroform, shaken vigorously, and centrifuged to recover the aqueous layer. The recovered aqueous layer is combined with 500 μl of 100% ethanol, kept at −80° C. for 20 minutes, and then centrifuged. The resultant pellet is dried, dissolved in a sterilized water, and used as a genomic DNA, which is subjected to a PCR as described above. When a human peripheral blood is employed as a sample, 10 ml of the blood is taken and the genomic DNA is extracted using a DNA-Extraction kit (Stratagene) in accordance with the attached manual. The resultant genomic DNA is subjected to a PCR as described above.

Example 5

Analysis of Genotype by PCR-SSCP

The polynucleotide employed as a primer in EXAMPLE 4 is labeled at its terminal with $^{32}$p using a DNA MEGA-LABEL Kit (Takara). About 1 μg of a genomic DNA obtained similarly to EXAMPLE 4 is used as a template together with each about 100 pmol of the labeled polynucleotide as a primer to conduct a PCR to amplify the DNA of the genome gene encoding an inventive protein. This PCR is conducted using a LA-Taq DNA polymerase (Takara) in a buffer attached specially with the enzyme described above in the presence of 100 μM of each of the 4 nucleotides (dATP, dTTP, dGTP, dCTP), which is subjected to 35 cycles, each cycle involving an incubation at 95° C. for 1 minutes followed by 68° C. for 1 minute. A ¹⁄₂₀ volume of the amplified DNA is denatured by heating in a 80% formamide at 80° C. for 5 minutes, and the ¹⁄₂₀ volume of this is subjected to an electrophoresis in 180 mM tris-borate buffer solution (pH8.0) on a 5% non-modified neutral polyacrylamide gel. The electrophoresis conditions involves room temperature, air cooling, constant power 40 W for 60 minutes. After completing the running, the gel is brought into a close contact with an X-ray film to obtain an autoradiogram, whereby detecting the DNA which had been amplified using the labeled polynucleotides as primers. The DNA encoding the relevant region of a standard protein is also run in parallel, whereby comparing with the mobility of the DNA derived from the sample. When the mobility of the these DNAs is different from each other, then the nucleotide sequence encoding the inventive protein in the nucleic acid in the test sample is judged to contain the nucleotide sequence encoding the amino acid sequence which is different from the amino acid sequence of the standard protein. Then, the part of the gel in the position corresponding to the band of the DNA derived from the test sample detected by an autoradiography is cut into a 1 mm×1 mm square piece, which is treated in 100 μl of a sterilized water at 90° C. for 10 minutes, a ¹⁄₂₀ volume of which is then used as a template to perform a PCR. The amplified DNA is subjected to an electrophoresis on a low melting point agarose gel and the DNA is recovered from the gel, and the recovered DNA is used as a template to perform a nucleotide sequencing using a BigDye Terminator cycle sequence ready reaction kit (Applied Biosystems) and an automatic DNA sequencer (Applied Biosystems, Model 377), whereby characterizing any variation.

Example 6

Transcriptional Regulation Ability of Inventive Protein (6-1) pGL3-TATA-Galx Preparation A pGL3-TATA-Calx4, which is the reporter gene plasmid employed for measuring the transcription regulation ability of a fusion protein between the GAL4 DNA binding region and any transcription regulatory factor, is one formed by introducing, into the upstream of the luciferase gene comprising a TATA minimum promoter, 4 copies in tandem of a DNA to which the GAL4 DNA binding region can be bound. By measuring the expression level of the luciferase in the case that the fusion protein between the GAL4 DNA binding region and any transcriptional regulation factor exerts its effect on the reporter gene plasmid described above, the transcription regulation ability possessed by this fusion protein can applicably be measured. This pGL3-TATA-Galx4 reporter gene plasmid was prepared as described below.

First, two oligonucleotides each comprising a DNA to which the GAL4 DNA binding region can be bound (5'-cgcgtcgagc tcgggtcgga ggactgtcct ccgactgctc gagtcgagct cgggtcggag gactgtcctc cgactgctcg aga-3' (SEQ ID NO:56), 5'-cgcgtctcga gcagtcggag gacagtcctc cgacccgagc tcgactcgag cagtcggagg acagtcctcc gacccgagct cga-3' (SEQ ID NO:57)) were hybridized, and phosphorylated at the 5' terminal using a T4 kinase, and then bound in tandem using a T4 ligase. The resultant double-stranded oligonucleotide was subjected to an electrophoresis using a low melting point agarose (NuseiveGTG; FMCbio) to recover a DNA fragment in which these double stranded oligonucleotide are bound in tandem. This was used as an insert fragment, which was reacted with 0.1 µg of the pGL3-TATA vector, which had been cleaved with MluI and then treated with an alkaline phosphatase (BAP C75; Takara) in the presence of a T4 Ligase (Takara) at 16° C. for 16 hours, whereby effecting the binding. As a result, a pGL3-TATA-Calx4, which is the reporter gene plasmid formed by introducing, into the upstream of the luciferase gene comprising a TATA minimum promoter, 4 copies in tandem of the DNA to which the GAL4 DNA binding region can be bound, was obtained.

(6-2) pRC/RSV-Gal4-DBD Preparation

On the other hand, a pRC/RSV-Gal4-DBD which is a plasmid expressing only the GAL4 DNA binding region (i.e., Gal4-DBD, a part lacking the transcriptional control region) was prepared as described below.

A pM which is a plasmid comprising a Gal4-DBD (contained in a commercial kit K1602-1; Clontech) was cleaved with NheI and XbaI, and then made blunt-ended using a T4 polymerase. This was subjected to an electrophoresis on a low melting point agarose (agarose L; Nippon Gene) to recover a DNA fragment (about 500 bp) encoding a Gal4-DBD. The recovered DNA fragment was employed as an insert fragment.

Then, a pRC/RVS (Invitrogen) was cleaved with HindIII, and made blunt-ended using a T4 polymerase. This was BAP-treated and used as a vector, and this vector (0.1 µg) was ligated with the insert fragment (0.5 µg) described above using a T4 ligase, whereby obtaining a pRC/RSV-Gal4-DBD (thus, Gal4 DBD). The correct construction of the plasmid for expressing the Gal4-DBD under the control of the RSV promoter was verified using an ABI Model 3700 autosequencer to determine the nucleotide sequence by a dye terminator method.

(6-3) pRC/RSV-MA Preparation

In order to express a fusion protein in which a GAL4 DNA binding region has been bound for example to a transcription regulation region of any transcription regulatory factor, a pRC/RSV-MA in which the recognition site of PmaCI which is a restriction enzyme capable of giving a blunt end has been introduced to the downstream of the Gal4-DBD was prepared. This plasmid has a translation region of a DNA encoding the Gal4-DBD downstream of the RSV promoter, and can be bound, at a further downstream PmaCI cleavage blunt end, with a blunt-ended DNA fragment in such a manner that the translation frame of the DNA encoding the Gal4-DBD is in agreement with the translation frame of the blunt-ended DNA fragment. As a result, the fusion protein in which a GAL4 DNA binding region has been bound for example to a transcription regulation region of any transcription regulatory factor can be expressed.

Typically, the pRC/RSV-MA was prepared as described below.

First, two oligonucleotides (5'-agcttcatcccacgtgagtcat-3', 5'-ctagatgactcacgtgggatga-3') were hybridized and then phosphorylated at the 5' terminal using a T4 kinase. This was used as an insert fragment and the pRC/RSV-Gal4-DBD prepared in Section (6-2) described above was used as a vector after the cleavage with HindIII 29dand XbaI followed by the BAP treatment, and the both were bound using a T4 ligase, whereby obtaining a pRC/RSV-MA.

(6-4) Preparation of pRC/RSV-MA-mNXF(AvaI frg)

A pRC/RSV-MA-mNXF (AvaI frg) which is a plasmid for expressing a fusion protein between a GAL4 DNA binding region (i.e., GAL4-DBD) and the transcription regulation region of an inventive protein (hereinafter this plasmid being sometimes referred to as Gal4-NXF Cterm) was prepared as described below.

First, the pGEM-mNXF prepared in EXAMPLE 1 was cleaved with avaI and NotI, and then made blunt-ended using a T4 polymerase. This was subjected to a low melting point agarose gel electrophoresis (agarose L; Nippon Gene) to recover a DNA fragment (about 1.8 kbp). The recovered DNA fragment was a DNA fragment encoding the transcription regulation region from the inventive protein bHLH motif-PAS domain to the C terminal. This recovered DNA fragment was used as an insert fragment and the pRC/RSV-MA prepared in Section (6-3) described above was used as a vector after the cleavage with PmaCI restriction enzyme followed by the BAP treatment, and the both were bound using a T4 ligase, whereby obtaining a pRC/RSV-MA-mNXF (AvaI frag). The correct direction of the binding of the insert fragment and the agreement of the translation frames in the binding region were verified using an ABI Model 3700 autosequencer to determine the nucleotide sequence by a dye terminator method.

Then, about $1 \times 10^7$ cells of a neuroblastoma IMR32 (ATCC No.CCL127; purchased from DAINIPPON SEIYAKU) were cultured in a 10% FBS-supplemented DMEM medium (NISSUI SEIYAKU) at 37° C. in the presence of 5% $CO^2$ in a petri dish (Falcon) whose diameter was about 10 cm. On the next day, the cultured cells were dispersed by a trypsin treatment, washed twice with a FBS-free DMEM medium, and then dispersed again in a FBS-free DMEM medium at the cell density of $1 \times 10^7$. 0.4 ml of this cell dispersion was combined with each 3 µg of the two plasmids prepared in Sections (6-2) and (6-3) described above, namely, pRC/RSV-Gal4-DBD and pRC/RSV-MA-mNXF (AvaI frag), and the mixture was transferred into an electroporation cuvette, where a transfection was conducted by an electroporation method employing a Gene pulser (BIO-RAD) under the conditions involving 200V and 950 µF. After the transfection, the culture medium was replaced with a 10% FBS-supplemented DMEM, and then further cultured in a 6-well plate for about 24 hours. Then, the culture medium was removed from the wells, and the cells depositing on the plate wall were washed twice with PBS(-), and then 200 µl per well of a 5-fold diluted PGC 50 (TOYO INK) was added and allowed to stand at room temperature for 30 minutes. 20 µl Aliquots of this cell suspension were dispensed into a opaque plate (Coning Coaster Co., Ltd.), and this plate was mounted on a luminometer LB96P (Berthold, co. ltd) fitted with an enzyme substrate automatic injector, and after dispensing 20 µl of the substrate solution PGL100 (TOYO INK) automatically the luciferase activity of each well was determined.

The results are shown in FIG. 1. As evident from FIG. 1, the one hybrid assay employing the reporter gene plasmid pGL3-TATA-Galx4 revealed a high level expression of the reporter gene in a transformant (designated as Gal4-NXF Cterm in Figure) expressing the fusion protein in which the GAL4 DNA binding region has been bound to the transcription regulation region (AvaI site to C terminal) of the inventive protein. On the other hand, the control transformant expressing only the Gal4 DNA binding region (designated as Gal4 DBD in Figure) exhibited no reporter gene expression. Thus, in the case employing as a host cell a neuroblastoma such as an IMR32, the inventive protein was proven to have a transcription activating ability as a transcription regulation ability.

(6-5) Preparation of pGL3-TATA Vector

The pGL3-TATA vector employed for constructing the pGL3-TATA-Galx4 in Examples described above was prepared as described below.

First, two oligonucleotides consisting of a nucleotide sequence near the TATA box of a mouse metallothionein I gene and the nucleotide sequence derived from a reader sequence (Genbank Accession No. J00605) (5'-GATCTC-GACTATAAAGAGGGCAGGCTGTC-CTCTAAGCGTCACCACGACTTCA-3' (SEQ ID NO:58), 5'-AGCTTGAAGTCGTGGTGACGCTTAGAGGAC AGCCTGCCCTCTTTATAGTCGA-3' (SEQ ID NO:59)) were hybridized and phosphorylated at the 5' terminal using a T4 kinase (this DNA is sometimes designated as TATA DNA). 1 µg of this TATA DNA was used as an insert fragment and was ligated (16° C., reaction for 16 hours) to a firefly luciferase gene-containing vector plasmid pGL3 (Promega) after a digestion with restriction enzymes BglII and HindIII followed by a treatment with the alkaline phosphatase (BAP C75; Takara) (0.1 µg) using a T4 Ligase (Takara), whereby obtaining a pGL3-TATA.

Example 7

Screening for Substance Altering Transcription Regulation Ability of Inventive Protein An animal cell expression pM vector (Clontech) is digested with SmaI and incubated in the presence of an alkaline phosphatase (BAP) for 1 hour at 65° C., and then subjected to a low melting point agarose gel electrophoresis to recover a vector DNA. On the other hand, the pGEM-hNXF prepared in EXAMPLE 1 is digested with NcoI and NotI, made blunt-ended using a Blunting Kit (Takara), subjected to a low melting point agarose gel electrophoresis to recover an about 2 kb DNA. The recovered vector DNA described above is mixed with the about 2 kb DNA and reacted with a L4 ligase. This reaction mixture is introduced into an E. coli DH5α competent cell (TOYOBO). The resultant E. coli transformant is cultured and its plasmid is extracted, and the plasmid thus obtained is subjected to a restriction enzyme analysis and a nucleotide sequencing. A plasmid resulting from the insertion of the about 2 kb DNA described above into a pM vector is selected and designated as pM-hNXF (SmaI). As a result, a vector for expressing a fusion protein between the GAL4 DNA binding region and a polypeptide comprising a partial amino acid sequence of the inventive protein is obtained.

About $2 \times 10^6$ Hela cells are inoculated onto a 10-cm plate and cultured in an FBS-supplemented E-MEM medium in the presence of $5O_2$ at 37° C. for one day. To the cells thus obtained, 3.75 µg of the plasmid pM-hNXF (SmaI) and 3.75 µg of the plasmid pFR-LUC (Stratagene; containing a Gal4-responsive luciferase gene) are introduced using a lipofectamine (Life Technologies) in accordance with the attached protocol. After culturing at 37° C. for 16 hours, the medium is replaced and the culture is continued further for 3 hours. The cells are harvested, suspended uniformly in an FBS-supplemented E-MEM medium, and then inoculated into a 96-well plate to which the culture medium containing any of various test substances dissolved in DMSO at a varying concentration had been added (final concentration of DMSO: 0.1). This plate is cultured at 37° C. for about 40 hours, received 50 µl/well of a 5-fold diluted cell solubilizer PGC50 (Nippon Gene), and allowed to stand at room temperature for 30 minutes with an intermittent gentle shaking to effect the cell dissolution. The cell solution thus obtained is dispensed in 10 µl aliquots into a 96-well white sample plate (Berthold, co. ltd), and examined immediately for the luminescence over a period of 5 seconds using a luminometer LB96p (Berthold, co. ltd) fitted with an automatic substrate injector while adding 50 µl/well of the enzyme substrate solution PGL100 (Nippon Gene).

Example 8

Acquisition of Genomic DNA Encoding Inventive Protein

The plasmid pGEM-mNXF obtained in EXAMPLE 1 was digested with EcoRI and HindIII and subjected to an agarose gel electrophoresis using a low melting point agarose (agarose L, Nippon Gene) to recover an about 0.6 kb DNA, 0.9 kb DBA and 1 kb DNA. Equal amounts of the recovered DNAs were combined, and an about 25 ng aliquot was taken and labeled with $^{32}p$ using an Amersham Multiprime DNA labeling system in accordance with the protocol attached to this system.

An E. coli XL1-Blue MRA (Stratagene) was cultured overnight and 0.3 ml of the resultant culture medium was combined with a mouse (129SvJ line) genomic DNA library (#946313m Stratagene) in such an amount that $5 \times 10^4$ plaques were formed per plate whose diameter was 15 cm, incubated at 37° C. for 20 minutes, and then immediately after adding 6.5 ml of a 0.7 agarose which had been kept at 50° C., and it was spread over a NZYM (10 g of Nzamine, 5 g of NaCl, 5 g of yeast extract, 2 g of MgSO$_4$.7H$_2$O and 5 g of agar dissolved in 1 L of water) whose diameter was 15 cm.

This plate was incubated at 37° C. overnight. Then the surface of the plate on which the plaques were formed was covered gently with a round nitrocellulose filter (Hybond N; Amersham) whose diameter was 15 cm, to which the plaques were transferred. This filter was allowed to stand at room temperature for 20 minutes, and then mounted for 5 minutes on a filter paper which had been immersed in a denaturing buffer (composition: 0.2N, NaOH, 1.5M NaCl). Subsequently, this filter was mounted for 1 minutes on a filter paper which had been immersed in a neutral buffer (composition: 0.4M Tris-HCl, pH7,5, 2×SSC), and then immersed in 500 ml of 2×SSC for 5 minutes. Then the filter was transferred onto a dry filter paper, allowed to stand at room temperature for several hours for drying, and then kept in an oven at 80° C. for 2 hours. The resultant filter was placed in a plastic seal bag, and incubated overnight at 65° C. in 50 ml of a hybrid buffer (composition: 5×SSC, 5 mM HEPES, pH7.0, 10× Denhart's solution, 20 µg/ml denatured salmon sperm DNA). Then it was combined with the entire amount of the $^{32}$P-labeled DNA described above which had been denatured by heating, and then incubated at 65° C. overnight. Then the filter was taken out and rinsed in 2×SSC at room temperature for 30 minutes, and then rinsed in 0.1×SSC at 65° C. for 40 minutes. The filter was then transferred into a fresh 0.1×SSC, rinsed at 65° C. for 40 minutes, allowed to stand on a filter paper at room temperature for drying, and subjected to an autoradiography (at −80° C. for 2 days).

A phage was recovered from a plate corresponding a part which exhibited a positive signal in the autoradiography described above, and suspended in 100 µl of an SM buffer (5.8 g of NaCl, 2 g of MgSO$_4$.7H$_2$O and 0.1 g of gelatin dissolved in 1 L of water, pH7.5). The resultant phage suspension was employed to perform a secondary screening by a hybridization method in a manner similar to that described above, except that the number of the plaques to be formed per plate was about 1000. A plaque was recovered from a plate corresponding a part which exhibited a positive signal in this screening, subjected to a tertiary screening similarly to the secondary screening, whereby obtaining a phage clone exhibiting the positive signal.

1 µl of the suspension of a phage clone which exhibited the positive signal described above was added to 100 µl of a TE buffer, boiled and employed as a template to perform a PCR. As primers, two primers which anneal to the both sides of the cloning site possessed by a Lambda FIXII vector employed for preparing the genomic DNA library described above [T7 universal primer and T3 universal primer (Stratagene)] were employed. The PCR reaction solution contained 5 µl of the boiling solution described above, each 1 pmol of the two primers described above, LA-taq polymerase (Takara) and a buffer attached to this enzyme in the total volume of 50 µl. The reaction was conducted in 35 cycles, each cycle consisting of an incubation for 1 minutes at 95° C. followed by 1 minutes at 50° C. followed by 10 minutes at 72° C. Subsequently, the reaction solution was subjected to an agarose gel electrophoresis to recover an about 7 kbp DNA. About 10 µg of the recovered DNA was employed as a template to perform a direct sequencing using a Dye Terminator Cycle Sequence FS kit (Perkin Elmer ABI) in accordance with the protocol attached to this kit. As a result, the DNA described above was revealed to comprise the nucleotide sequence represented by SEQ ID NO:54. By comparing the resultant nucleotide sequence with the nucleotide sequence represented by SEQ ID NO:5, the intron/exon structure was clarified.

Example 9

Promotion of Drebrin 1 Expression by Inventive Protein

First, about 1×10$^7$ SK-N-MC cells (ATCC No. CHTB10; purchased from DAINIPPON SEIYAKU) were cultured in a 10% FBS-supplemented DMEM medium (NISSUI SEIYAKU) at 37° C. in the presence of 5% CO$_2$ in a petri dish (Falcon) whose diameter was about 10 cm.

On the next day, the cultured cells were dispersed by a trypsin treatment, washed twice with a FBS-free DMEM medium, and then dispersed again in a FBS-free DMEM medium at the cell density of 1×10$^7$. 0.4 ml of this cell dispersion was combined with 10 µg of the plasmids prepared as described above, namely, (a) a pRC/RSV-mNXFsense which is a plasmid expressing the sense strand of the DNA encoding the full-length inventive protein and (b) a pRC/RSV-mNXFantisense which is a plasmid expressing the antisense strand of the DNA encoding the full-length inventive protein downstream of the RVS promoter, and the mixture was transferred into an electroporation cuvette, where a transfection was conducted by an electroporation method employing a Gene pulser (BIORAD) under the conditions involving 200V and 950 µF. After the transfection, the culture medium was replaced with a 10% FBS-supplemented DMEM, and then further cultured in a 10-cm petri dish for about 24 hours. After the culture, (a) 5 dishes of the pRC/RSV-mNXFsense-introduced cell and (b) 5 dishes of the pRC/RSV-mNXFantisense-introduced cell were subjected to the purification of the DNA-free total RNA using a commercial RNA purification and radiolabelling kit, namely, Atlas Pure Total RNA Labeling system (K1038-1; Clontech). The RNA yield was (a) 23 µg and (b) 26 µg. Subsequently, the commercial kit described above and the resultant RNA were employed for radiolabelling each RNA with [α-P$^{32}$]-dATP (Amersham Pharmacia) using the specific primers contained in the commercial kit together with the reverse transcriptase. The radiolabeled RNA thus obtained (hereinafter referred to as a probe) was purified using the commercial kit described above, and this purified RNA was adjusted at 1.3×10$^5$ DPM, and then used in the hybridization reaction described below. The hybridization reaction was conducted using a commercial kit including a nylon membrane onto which various genes had been blotted (Atlas cDNA Expression array-Neurobiology; 7736-1) together with the attached hybridization buffers. The hybridization conditions involved the reactions of (a) the nylon membrane corresponding to the probe derived from the pRC/RSV-mNXFsense-introduced cell and (b) the nylon membrane corresponding to the probe derived from the pRC/RSV-mNXFantisense-introduced cell, over a period of 18 hours under identical conditions in identical incubators. After the reaction, the nylon membrane was washed with 2×SSC, 1% SDS buffer (68° C., 30 minutes). This procedure was repeated 4 times, and the washing was further conducted in 0.1×SSC, 0.5% SDS buffer (68° C., 30 minutes). Each nylon membrane was wrapped with a plastic film, exposed to an IP plate (FUJI FILM) for 7 days, and then subjected to the quantification and the comparison of the probe hybridization signals corresponding to various genes on the nylon membrane using an imaging analyzer (BASstation, FUJI FILM).

As a result, a significantly more intense signal to the drebrin 1 gene was noted by (a) the hybridization signal on the nylon membrane corresponding to the probe derived from the pRC/RSV-mNXFsense-introduced cell rather than (b) the hybridization signal on the nylon membrane corresponding to the probe derived from the pRC/RSV-mNX-Fantisense-introduced cell. Thus, the inventive protein was proven to have an ability of promoting the expression of the drebrin 1.

Example 10

Preparation of Reporter Gene Operably Ligated with Expression Regulation Region of DNA Encoding Inventive Protein and Verification of its Promoter Activity: Mouse-Originated Inventive Protein Genome Nucleotide Sequencing (10-1) Preparation of Materials The nucleotide sequence of the genome of the inventive protein derived from a mouse represented by SEQ ID NO:55 was determined as described below.

First, for the purpose of amplifying only the FIXII vector insert sequence part of the clone designated as Clone 12 among the genome phage clones of the inventive protein obtained by the screening as described above, a T7 universal primer and a T3 universal primer (Stratagene) which is a primer pair provided on the FIXIII vector were employed together with a LA-Taq polymerase (Takara) and 1 µl of a Clone 12 phage solution to conduct a PCR reaction including 35 cycles, each cycle involving an incubation at 95° C. for 1 minutes followed by 68° C. for 20 minutes. As a result, an amplified DNA fragment (about 21 kbp) was obtained. The resultant amplified DNA fragment was subjected to an electrophoresis on a 0.8% low melting point agarose (agarose L; Nippon Gene), whereby purifying and recovering the DNA fragment. The purified and recovered DNA fragment was subjected to a custom primer direct sequencing using a capillary sequencer (PE-biosystems, Model 3700) and a Dye Terminator Sequence Kit FS ver 2 (PE-biosystems), whereby determining the entire nucleotide sequence (SEQ ID NO:55) of this DNA fragment.

(10-2) Preparation of Reporter Gene Operably Ligated with Expression Regulation Region of DNA Encoding Inventive Protein In order to obtain the expression regulation region of a DNA encoding an inventive protein containing about 10 kbp, 5 kbp, 2.5 kbp or 1 kbp upstream of the transcription initiation point of the gene of an inventive protein derived from a mouse (nucleotide numbers 9437 to 9442 in the nucleotide sequence of the genome of the inventive protein derived from the mouse), the nucleotide sequence of the genome of the inventive protein represented by SEQ ID NO:55 was utilized to design the forward PCR primer consisting of any of the following nucleotide sequences. About 10 kbp upstream: 5'-gggcggtaccatacctagggccaatag-gagtgatgagcccatgtc-3' (SEQ ID NO:60);

About 5 kbp upstream: 5'-gggcggtaccaacgaggaatctctcttc-ctctccactgtccgggc-3' (SEQ ID NO:61);

About 2.5 kbp upstream: 5'-gggcggtaccctgcttaaattgcttg-gagaccagctgtggaccca-3' (SEQ ID NO:62);

About 1 kbp upstream: 5'-gggcggtaccctcagtgacaagtgca-caggcagaacgaggagccc-3' (SEQ ID NO:63).

Similarly utilizing the nucleotide sequence of the genome of the inventive protein, a reverse PCR primer comprising the following nucleotide sequence was also designed.

5'-gggcacgcgttcgcctgcctcgatccgccttatgtagctcctgac-3' (SEQ ID NO:64).

Into the forward primer employed here, a KpnI restriction enzyme site had been introduced, and a MluI restriction enzyme site had been introduced into the reverse primer. Using the forward primer and the reverse primer described above as a primer pair together with 1 µl of the genome phage clone of the inventive protein derived from the mouse as a template, a PCR was conducted using a KODplus polymerase (TOYOBO). The PCR conditions employed 35 cycles, each cycle involving an incubation at 95° C. for 1 minutes followed by 68° C. for 10 minutes. As a result, the expression regulation regions of the DNA encoding the inventive protein containing about 10 kbp, 5 kbp, 2.5 kbp and 1 kbp upstream of the transcription initiation point of the gene of the inventive protein derived from the mouse were amplified. Each of these regions was cleaved simultaneously by both of the restriction enzymes KpnI and MluI, and subjected to a low melting point agarose electrophoresis (agarose L; Nippon Gene) to recover each amplified DNA fragment. Each recovered amplified DNA fragment (about 0.5 µg) was employed as an insert fragment, which was ligated to a pGL3-TATA vector prepared in EXAMPLE 6 which had been cleaved by KpnI and MluI and then treated with an alkaline phosphatase (BAP C75; Takara) (0.1 µg) using a T4 ligase (Takara) (16° C., 16 hours), whereby obtaining the plasmids into which the expression regulation regions of the DNA encoding the inventive protein containing about 10 kbp (nucleotide Nos.72 to 9436 in the nucleotide sequence represented by SEQ ID NO:55), 5 kbp (nucleotide Nos.4364 to 9436 in the nucleotide sequence represented by SEQ ID NO:55), 2.5 kbp (nucleotide Nos.6889 to 9436 in the nucleotide sequence represented by SEQ ID NO:55) and 1 kbp (nucleotide Nos.8216 to 9436 in the nucleotide sequence represented by SEQ ID NO:55) upstream of the transcription initiation point of the gene of the inventive protein derived from the mouse had been inserted into the upstream of the luciferase gene comprising a TATA minimum promoter.

(10-3) Verification of Promoter Activity Possessed by Expression Regulation Region A pGL3-TK-BSD, which was a control reporter plasmid for investigating the relative activity of the promoter activity possessed by the expression regulation region of the DNA encoding the inventive protein, was prepared as described below. The luciferase gene of this control reporter plasmid is regulated by the promoter of a thymidine kinase of a herpes simplex virus.

First, a plasmid pRL-TK (Promega) was cleaved by both of HindIII and BglII, subjected to a low melting point agarose electrophoresis (agarose L; Nippon Gene) to recover a DNA fragment (760 bp) containing a TK promoter. Then, a plasmid pGL3 was cleaved by HindIII and BglII, subjected to a BAP treatment followed by a low melting point agarose electrophoresis to recover a BglII-HindIII DNA fragment containing a pGL-derived luciferase gene. About 0.1 µg of the recovered DNA fragment was mixed with about 0.2 µg of the DNA containing the TK promoter described above, and the mixture was reacted with a T4 ligase to prepare a pGL3-TK which was a plasmid comprising the TK promoter-containing DNA as being inserted between the HindIII cleavage site and the BglII cleavage site of the pGL. The DNA of the pGL3-TK thus obtained was cleaved by BanmHI and then subjected to a BAP treatment, followed by a low melting point agarose electrophoresis to recover a DNA fragment which was detected as a single band. This DNA fragment was ligated in the presence of a T4 ligase to a DNA encoding a blasticidin S deaminase gene expression cassette prepared by digesting a plasmid PUCSV-BSD (purchased from FUNAKOSHi) by BamHI, whereby preparing a pGL3-TK-BSD, which is a plasmid comprising the blasticidin S deaminase gene expression cassette as being inserted at the BamHI cleavage site of the pGL3-TK.

About $5 \times 10^6$ cells of 293 cell were cultured in a 10% FBS-supplemented DMEM medium (NISSUI SEIYAKU) at 37° C. in the presence of 5% $CO^2$ in a petri dish (Falcon) whose diameter was about 10 cm. On the next day, the cultured cells were dispersed by a trypsin treatment, washed twice with a FBS-free DMEM medium, and then dispersed again in a FBS-free DMEM medium at the cell density of $5 \times 10^6$. 0.4 ml of this cell dispersion was combined with each 3 µg of the plasmids prepared as described above, and the mixture was transferred into an electroporation cuvette, where a transfection was conducted by an electroporation method employing a Gene pulser (BIORAD) under the conditions involving 200V and 950 µF. After the transfection, the culture medium was replaced with a 10% FBS-supplemented DMEM, and then further cultured in a 6-well plate for about 24 hours. Then, the culture medium was removed from the wells, and the cells depositing on the plate wall were washed twice with PBS(-), and then 200 µl per well of a 5-fold diluted PGC 50 (TOYO INK) was added and allowed to stand at room temperature for 30 minutes. 20 µl Aliquots of this cell suspension were dispensed into a opaque plate (Coning Coaster Co., Ltd.), and this plate was mounted on a luminometer LB96P (Berthold, co. ltd) fitted with an enzyme substrate automatic injector, and after dispensing 20 µl of the substrate solution PGL100 (TOYO INK) automatically the luciferase activity of each well was determined.

The results are shown in FIG. 2. The thymidine kinase promoter of the herpes simplex virus (HSV-TK) and the inventive protein-encoding DNA expression regulation region promoter activity were compared, and it was revealed that any of the inventive protein-encoding DNA expression regulation regions containing about 5 kbp, 2.5 kbp and 1 kbp upstream of the transcription initiation point of the gene of the inventive protein (designated as −5 kbp NXF genome, −2.5 kbp NXF genome, and −1 kbp NXF genome in Figure) exhibited a promoter activity which was equal to or higher than that of the HSV-TK promoter (designated as HSV-TK enhancer in Figure) in the 293 cells. It is noteworthy especially that a part critical for the promoter activity identified here was revealed to be present in a region containing about 1 kbp upstream of the transcription initiation point of the gene of the inventive protein.

Example 11

Method for Screening for Altering Transcription Regulation Ability of Inventive Protein Utilizing Expression Regulation Region of DNA Encoding Present Protein The plasmids into which the expression regulation regions of the DNA encoding the inventive protein containing about 10 kbp, 5 kbp, 2.5 kbp and 1 kbp upstream of the transcription initiation point of the gene of the inventive protein derived from the mouse had been inserted into the upstream of the luciferase gene comprising a TATA minimum promoter prepared in EXAMPLE 10 are transfected into the 293 cells by an electroporation method. After the transfection, the transfected cells are inoculated to a 96-well plate to which (a) a test substance-free culture medium or (b) a test substance-supplemented culture medium had been added. The cells are cultured at 37° C. for about 24 hours, and then examined for the luciferase activity. When the comparison of the measured luciferase activities revealed that the luciferase activity in case (b) is higher than that in case (a), then the relevant test substance is judged to be a substance increasing the expression of the gene of the inventive protein. On the contrary, a lower luciferase activity in case (b) suggests that the relevant test substance is a substance reducing the expression of the gene of the invention. Thus, the substance altering the transcription regulation ability of the inventive protein can be screened for.

INDUSTRIAL APPLICABILITY

Based on the present invention, it becomes possible to provide a bHLH-PAS protein, DNA encoding this protein and the like.

Free Text in Sequence Listing

SEQ ID NO:7
Designed oligonucleotide primer for PCR SEQ ID NO:8
Designed oligonucleotide primer for PCR SEQ ID NO:9
Designed oligonucleotide primer for PCR SEQ ID NO:10
Designed oligonucleotide primer for PCR SEQ ID NO:11
Designed oligonucleotide primer for PCR SEQ ID NO:12
Designed oligonucleotide primer for PCR SEQ ID NO:13
Designed oligonucleotide primer for PCR SEQ ID NO:14
Designed oligonucleotide primer for PCR SEQ ID NO:15
Designed oligonucleotide primer for PCR SEQ ID NO:16
Designed oligonucleotide primer for PCR SEQ ID NO:17
Designed oligonucleotide primer for PCR SEQ ID NO:18
Designed oligonucleotide primer for PCR SEQ ID NO:19
Designed oligonucleotide primer for PCR SEQ ID NO:20
Designed oligonucleotide primer for PCR SEQ ID NO:21
Designed oligonucleotide primer for PCR SEQ ID NO:22
Designed oligonucleotide primer for PCR SEQ ID NO:23
Designed oligonucleotide primer for PCR SEQ ID NO:24
Designed oligonucleotide primer for PCR SEQ ID NO:25
Designed oligonucleotide primer for PCR SEQ ID NO:26
Designed oligonucleotide primer for PCR SEQ ID NO:27
Designed oligonucleotide primer for PCR SEQ ID NO:28
Designed oligonucleotide primer for PCR SEQ ID NO:29
Designed oligonucleotide primer for PCR SEQ ID NO:30
Designed oligonucleotide primer for PCR SEQ ID NO:31
Designed oligonucleotide primer for PCR SEQ ID NO:32
Designed oligonucleotide primer for PCR SEQ ID NO:33
Designed oligonucleotide primer for PCR SEQ ID NO:34
Designed oligonucleotide primer for PCR SEQ ID NO:35
Designed oligonucleotide primer for PCR SEQ ID NO:36
Designed oligonucleotide primer for PCR SEQ ID NO:37
Designed oligonucleotide primer for PCR SEQ ID NO:38
Designed oligonucleotide primer for PCR SEQ ID NO:39
Designed oligonucleotide primer for PCR SEQ ID NO:40
Designed oligonucleotide primer for PCR SEQ ID NO:41
Designed oligonucleotide primer for PCR SEQ ID NO:42
Designed oligonucleotide primer for PCR SEQ ID NO:52
Designed oligonucleotide primer for PCR SEQ ID NO:53
Designed oligonucleotide primer for PCR SEQ ID NO:56
Designed oligonucleotide SEQ ID NO:57

The invention claimed is:

1. An isolated protein which is any of the following proteins (a) to (e):

(a) a protein comprising the amino acid sequence represented by any of SEQ ID NOs: 1 to 3, (b) a protein comprising an amino acid sequence exhibiting an amino acid identity of 90% or more to the amino acid sequence represented by any of SEQ ID NOs: 1 to 3 and also having a transcription regulation ability to regulate expression of drebrin 1, (c) a protein comprising an amino acid sequence encoded by a DNA which hybridizes under a stringent condition that includes washing for 30 minutes at 65° C. in 0.1×SSC with a DNA consisting of the nucleotide sequence represented by the nucleotide numbers 102 to 2507 in the nucleotide sequence represented by SEQ ID NO: 4 and also having a transcription regulation ability to regulate expression of drebrin 1, (d) a protein comprising an amino acid sequence encoded by a DNA which hybridizes under a stringent condition that includes washing for 30 minutes at 65° C. in 0.1×SSC with a DNA consisting of the nucleotide sequence represented by the nucleotide numbers 51 to 2456 in the nucleotide sequence represented by SEQ ID NO: 5 and also having a transcription regulation ability to regulate expression of drebrin 1, and (e) a protein comprising an amino acid sequence encoded by a DNA which hybridizes under a stringent condition that includes washing for 30 minutes at 65° C. in 0.1×SSC with a DNA consisting of the nucleotide sequence represented by the nucleotide numbers 35 to 2440 in the nucleotide sequence represented by SEQ ID NO: 6 and also having a transcription regulation ability to regulate expression of drebrin 1.

2. An isolated DNA encoding any of the following proteins (a) to (e):

(a) a protein comprising the amino acid sequence represented by any of SEQ ID NOs: 1 to 3, (b) a protein comprising an amino acid sequence exhibiting an amino acid identity of 90% or more to the amino acid sequence represented by any of SEQ ID NOs: 1 to 3 and also having a transcription regulation ability to regulate expression of drebrin 1, (c) a protein comprising an amino acid sequence encoded by a DNA which hybridizes under a stringent condition that includes washing for 30 minutes at 65° C. in 0.1×SSC with a DNA consisting of the nucleotide sequence represented by the nucleotide numbers 102 to 2507 in the nucleotide sequence represented by SEQ ID NO: 4 and also having a transcription regulation ability to regulate expression of drebrin 1, (d) a protein comprising an amino acid sequence encoded by a DNA which hybridizes under a stringent condition that includes washing for 30 minutes at 65° C. in 0.1×SSC with a DNA consisting of the nucleotide sequence represented by the nucleotide numbers 51 to 2456 in the nucleotide sequence represented by SEQ ID NO: 5 and also having a transcription regulation ability to regulate expression of drebrin 1, and (e) a protein comprising an amino acid sequence encoded by a DNA which hybridizes under a stringent condition that includes washing for 30 minutes at 65° C. in 0.1×SSC with a DNA consisting of the nucleotide sequence represented by the nucleotide numbers 35 to 2440 in the nucleotide sequence represented by SEQ ID NO: 6 and also having a transcription regulation ability to regulate expression of drebrin 1.

3. An isolated DNA comprising any of the following nucleotide sequences (a) to (d):
   (a) the nucleotide sequence represented by the nucleotide numbers 102 to 2507 in the nucleotide sequence represented by SEQ ID NO: 4,
   (b) the nucleotide sequence represented by the nucleotide numbers 51 to 2456 in the nucleotide sequence represented by SEQ ID NO: 5,
   (c) the nucleotide sequence represented by the nucleotide numbers 35 to 2440 in the nucleotide sequence represented by SEQ ID NO: 6, and
   (d) the nucleotide sequence represented by the nucleotide numbers 1419 to 6164 in the nucleotide sequence represented by SEQ ID NO: 54.

4. A vector containing the DNA according to claim 2 or 3.

5. A vector containing a DNA being formed by operably connecting a promoter to the upstream of the DNA according to claim 2 or 3.

6. A method for producing a vector comprising integrating the DNA according to claim 2 or 3 into a vector which can replicate itself in a host cell.

7. A transformed cell formed by introducing the DNA according to claim 2 or 3 into a host cell.

8. A transformed cell according to claim 7 wherein the host cell is an animal cell.

9. A transformed cell according to claim 7 wherein the host cell is a *E. coli* or yeast.

10. A method for producing a transformed cell comprising introducing the DNA according to claim 2 or 3 into a host cell.

11. A method for producing any of the following proteins (a) to (e) comprising culturing a transformed cell formed by introducing the DNA encoding said protein and recovering said protein from the culture:
    (a) a protein comprising the amino acid sequence represented by any of SEQ ID NOs: 1 to 3,
    (b) a protein comprising an amino acid sequence exhibiting an amino acid identity of 90% or more to the amino acid sequence represented by any of SEQ ID NOs: 1 to 3 and also having a transcription regulation ability to regulate expression of drebrin 1,
    (c) a protein comprising an amino acid sequence encoded by a DNA which hybridizes under a stringent condition that includes washing for 30 minutes at 65° C. in 0.1×SSC with a DNA consisting of the nucleotide sequence represented by the nucleotide numbers 102 to 2507 in the nucleotide sequence represented by SEQ ID NO: 4 and also having a transcription regulation ability to regulate expression of drebrin 1,
    (d) a protein comprising an amino acid sequence encoded by a DNA which hybridizes under a stringent condition that includes washing for 30 minutes at 65° C. in 0.1×SSC with a DNA consisting of the nucleotide sequence represented by the nucleotide numbers 51 to 2456 in the nucleotide sequence represented by SEQ ID NO: 5 and also having a transcription regulation ability to regulate expression of drebrin 1, and
    (e) a protein comprising an amino acid sequence encoded by a DNA which hybridizes under a stringent condition that includes washing for 30 minutes at 65° C. in 0.1×SSC with a DNA consisting of the nucleotide sequence represented by the nucleotide numbers 35 to 2440 in the nucleotide sequence represented by SEQ ID NO: 6 and also having a transcription regulation ability to regulate expression of drebrin 1, into a host cell.

12. A method for screening for a substance which binds to any of the following proteins (a) to (e) comprising:
    (1) a step for bringing said protein into contact with a test sample; and
    (2) a step for selecting a substance which binds to said protein;
    wherein said protein is selected from the group consisting of:
    (a) a protein comprising the amino acid sequence represented by any of SEQ ID NOs: 1 to 3,
    (b) a protein comprising an amino acid sequence exhibiting an amino acid identity of 90% or more to the amino acid sequence represented by any of SEQ ID NOs: 1 to 3 and also having a transcription regulation ability to regulate expression of drebrin 1,
    (c) a protein comprising an amino acid sequence encoded by a DNA which hybridizes under a stringent condition that includes washing for 30 minutes at 65° C. in 0.1×SSC with a DNA consisting of the nucleotide sequence represented by the nucleotide numbers 102 to 2507 in the nucleotide sequence represented by SEQ ID NO: 4 and also having a transcription regulation ability to regulate expression of drebrin 1,
    (d) a protein comprising an amino acid sequence encoded by a DNA which hybridizes under a stringent condition that includes washing for 30 minutes at 65° C. in 0.1×SSC with a DNA consisting of the nucleotide sequence represented by the nucleotide numbers 51 to 2456 in the nucleotide sequence represented by SEQ ID NO: 5 and also having a transcription regulation ability to regulate expression of drebrin 1, and
    (e) a protein comprising an amino acid sequence encoded by a DNA which hybridizes under a stringent condition that includes washing for 30 minutes at 65° C. in 0.1×SSC with a DNA consisting of the nucleotide sequence represented by the nucleotide numbers 35 to 2440 in the nucleotide sequence represented by SEQ ID NO: 6 and also having a transcription regulation ability to regulate expression of drebrin 1.

13. A method for measuring a transcription regulation ability of any of the following proteins (a) to (e) comprising:
    a step for measuring the expression level of a reporter gene in a first transformed cell, wherein said first transformed cell is formed by introducing a gene i) and gene ii) into a host cell and in a second transformed cell, wherein said second transformed cell is formed by introducing a gene iii) and gene ii) and then comparing the measured expression levels from said first transformed cell and said second transformed cell; wherein:
    gene i) is a chimeric gene formed by connecting, to a downstream of a promoter which is capable of functioning in a host cell, a DNA encoding a fusion protein of a DNA binding region of a transcription regulatory factor which is capable of functioning in the host cell and said protein;
gene ii) is a reporter gene formed by connecting a DNA encoding a reporter protein to a downstream of a promoter containing a DNA to which the DNA binding region described in i) can be bound and a minimum promoter which is capable of functioning in a host cell;
gene iii) is a gene formed by connecting, to the downstream of the promoter described in i), a DNA encoding the DNA binding region described in i); and wherein said protein is selected from the group consisting of:
(a) a protein comprising the amino acid sequence represented by any of SEQ ID NOs: 1 to 3,
(b) a protein comprising an amino acid sequence exhibiting an amino acid identity of 90% or more to the amino acid sequence represented by any of SEQ ID NOs: 1 to 3 and also having a transcription regulation ability to regulate expression of drebrin 1,
(c) a protein comprising an amino acid sequence encoded by a DNA which hybridizes under a stringent condition that includes washing for 30 minutes at 65° C. in 0.1×SSC with a DNA consisting of the nucleotide sequence represented by the nucleotide numbers 102 to 2507 in the nucleotide sequence represented by SEQ ID No. 4 and also having a transcription regulation ability to regulate expression of drebrin 1,
(d) a protein comprising an amino acid sequence encoded by a DNA which hybridizes under a stringent condition that includes washing for 30 minutes at 65° C. in 0.1×SSC with a DNA consisting of the nucleotide sequence represented by the nucleotide numbers 51 to 2456 in the nucleotide sequence represented by SEQ ID NO: 5 and also having a transcription regulation ability to regulate expression of drebrin 1, and
(e) a protein comprising an amino acid sequence encoded by a DNA which hybridizes under a stringent condition that includes washing for 30 minutes at 65° C. in 0.1×SSC with a DNA consisting of the nucleotide sequence represented by the nucleotide numbers 35 to 2440 the nucleotide sequence represented by SEQ ID NO: 6 and also having a transcription regulation ability to regulate expression of drebrin 1.

14. A method for screening for a substance which alters the transcription regulation ability of any of the following proteins (a) to (e) comprising:
(1) a step for bringing a transformed cell formed by introducing:
i) a chimeric gene formed by connecting, to a downstream of a promoter which is capable of functioning in a host cell, a DNA encoding a fusion protein of a DNA binding region of a transcription regulatory factor which is capable of functioning in the host cell and said protein, and
ii) a reporter gene formed by connecting a DNA encoding a reporter protein to a downstream of a promoter containing a DNA to which the DNA binding region described in i) can be bound and a minimum promoter which is capable of functioning in a host cell, into a host cell into contact with a test substance and then measuring the expression level of said reporter gene in the presence of the test substance, and
(2) a step for selecting a test substance which results in a expression level of said reporter gene, as measured in the step (a), which is different from the expression level of said reporter gene in the absence of the test substance;
wherein said protein is selected from the group consisting of:
(a) a protein comprising the amino acid sequence represented by any of SEQ ID NOs: 1 to 3,
(b) a protein comprising an amino acid sequence exhibiting an amino acid identity of 90% or more to the amino acid sequence represented by any of SEQ ID NOs: 1 to 3 and also having a transcription regulation ability to regulate expression of drebrin 1,
(c) a protein comprising an amino acid sequence encoded by a DNA which hybridizes under a stringent condition that includes washing for 30 minutes at 65° C. in 0.1×SSC with a DNA consisting of the nucleotide sequence represented by the nucleotide numbers 102 to 2507 in the nucleotide sequence represented by SEQ ID NO: 4 and also having a transcription regulation ability to regulate expression of drebrin 1,
(d) a protein comprising an amino acid sequence encoded by a DNA which hybridizes under a stringent condition that includes washing for 30 minutes at 65° C. in 0.1×SSC with a DNA consisting of the nucleotide sequence represented by the nucleotide numbers 51 to 2456 in the nucleotide sequence represented by SEQ ID NO: 5 and also having a transcription regulation ability to regulate expression of drebrin 1, and
(e) a protein comprising an amino acid sequence encoded by a DNA which hybridizes under a stringent condition that includes washing for 30 minutes at 65° C. in 0.1×SSC with a DNA consisting of the nucleotide sequence represented by the nucleotide numbers 35 to 2440 in the nucleotide sequence represented by SEQ ID NO: 6 and also having a transcription regulation ability to regulate expression of drebrin 1.

15. A method for screening for a substance which alters the intracellular expression level of any of the following proteins (a) to (e) comprising:
(1) a step for bringing a transformed cell formed by introducing into a host cell a reporter gene operably ligated to the expression regulation region of a DNA encoding said protein into contact with a test substance and then measuring the expression level of said reporter gene in the presence of the test substance, and
(2) a step for selecting a test substance which results in a expression level of said reporter gene, as measured in the step (1), which is different from the expression level of said reporter gene in the absence of the test substance;
wherein said protein is selected from the group consisting of:
(a) a protein comprising the amino acid sequence represented by any of SEQ ID NOs: 1 to 3,
(b) a protein comprising an amino acid sequence exhibiting an amino acid identity of 90% or more to the amino acid sequence represented by any of SEQ ID NOs: 1 to 3 and also having a transcription regulation ability to regulate expression of drebrin 1,
(c) a protein comprising an amino acid sequence encoded by a DNA which hybridizes under a stringent condition that includes washing for 30 minutes at 65° C. in 0.1×SSC with a DNA consisting of the nucleotide sequence represented by the nucleotide numbers 102 to 2507 in the nucleotide sequence represented by SEQ ID NO: 4 and also having a transcription regulation ability to regulate expression of drebrin 1,
(d) a protein comprising an amino acid sequence encoded by a DNA which hybridizes under a stringent condition that includes washing for 30 minutes at 65° C. in 0.1×SSC with a DNA consisting of the nucleotide sequence represented by the nucleotide numbers 51 to 2456 in the nucleotide sequence represented by SEQ ID NO: 5 and also having a transcription regulation ability to regulate expression of drebrin 1, and (e) a protein comprising an amino acid sequence encoded by a DNA which hybridizes under a stringent condition that includes washing for 30 minutes at 65° C. in 0.1×SSC with a DNA consisting of the nucleotide sequence represented by the nucleotide numbers 35 to 2440 in the nucleotide sequence represented by SEQ ID NO: 6 and also having a transcription regulation ability to regulate expression of drebrin 1.

16. A method for analyzing a genotype of a gene encoding any of the following proteins (a) to (e) comprising a step for investigating whether a nucleotide sequence encoding said protein, in a nucleic acid in a test sample, contains a nucleotide sequence encoding an amino acid sequence which is different from the amino acid sequence of a standard protein or not;

wherein said protein is selected from the group consisting of:

(a) a protein comprising the amino acid sequence represented by any of SEQ ID NOs: 1 to 3, (b) a protein comprising an amino acid sequence exhibiting an amino acid identity of 90% or more to the amino acid sequence represented by any of SEQ ID NOs: 1 to 3 and also having a transcription regulation ability to regulate expression of drebrin 1, (c) a protein comprising an amino acid sequence encoded by a DNA which hybridizes under a stringent condition that includes washing for 30 minutes at 65° C. in 0.1×SSC with a DNA consisting of the nucleotide sequence represented by the nucleotide numbers 102 to 2507 in the nucleotide sequence represented by SEQ ID NO: 4 and also having a transcription regulation ability to regulate expression of drebrin 1, (d) a protein comprising an amino acid sequence encoded by a DNA which hybridizes under a stringent condition that includes washing for 30 minutes at 65° C. in 0.1×SSC with a DNA consisting of the nucleotide sequence represented by the nucleotide numbers 51 to 2456 in the nucleotide sequence represented by SEQ ID NO: 5 and also having a transcription regulation ability to regulate expression of drebrin 1, and (e) a protein comprising an amino acid sequence encoded by a DNA which hybridizes under a stringent condition that includes washing for 30 minutes at 65° C. in 0.1×SSC with a DNA consisting of the nucleotide sequence represented by the nucleotide numbers 35 to 2440 in the nucleotide sequence represented by SEQ ID NO: 6 and also having a transcription regulation ability to regulate expression of drebrin 1.

17. A method according to claim 16 wherein the step for investigating whether a nucleotide sequence encoding the amino acid sequence which is different from the amino acid sequence of a standard protein is contained or not comprises a step for amplifying a DNA encoding any of the proteins (a) to (e) using the nucleic acid in the test sample as a template and then determining the nucleotide sequence of the amplified DNA.

18. A method according to claim 16 wherein the step for investigating whether a nucleotide sequence encoding the amino acid sequence which is different from the amino acid sequence of a standard protein is contained or not comprises a step for amplifying a DNA encoding the amino acid sequence of any of the proteins (a) to (e) using the nucleic acid in the test sample as a template and then subjecting the amplified DNA to an electrophoresis to measure the mobility.

19. A method according to claim 16 wherein the step for investigating whether a nucleotide sequence encoding the amino acid sequence which is different from the amino acid sequence of a standard protein is contained or not comprises a step for investigating the pattern of a hybridization under a stringent condition between the nucleic acid of a test sample or an amplification product of said nucleic acid and a polynucleotide consisting of 10 to 5000 nucleotides capable of hybridizing under a stringent condition with a polynucleotide consisting of the nucleotide sequence represented by SEQ ID NO: 4, 5, 6 or 54 or the nucleotide sequence complementary to said nucleotide sequence wherein said stringent condition includes washing for 30 minutes at 65° C. in 0.1×SSC.

20. A method according to any of claims 16 to 19 wherein the amino acid sequence of the standard protein is the amino acid sequence represented by SEQ ID NO: 1, 2 or 3.

21. A method for promoting the expression of a drebrin 1 in a mammalian cell comprising a step for providing the mammalian cell with the DNA according to claim 2 or 3 in a position enabling the expression of said DNA in said cell.

* * * * *